US007273721B2

(12) United States Patent
Pompejus et al.

(10) Patent No.: US 7,273,721 B2
(45) Date of Patent: Sep. 25, 2007

(54) CORYNEBACTERIUM GLUTAMICUM GENES ENCODING PROTEINS INVOLVED IN MEMBRANE SYNTHESIS AND MEMBRANE TRANSPORT

(75) Inventors: Markus Pompejus, Waldsee (DE); Burkhard Kroger, Limburgerhof (DE); Hartwig Schröder, Nussloch (DE); Oskar Zelder, Speyer (DE); Gregor Haberhauer, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 329 days.

(21) Appl. No.: 10/627,476

(22) Filed: Jul. 25, 2003

(65) Prior Publication Data

US 2004/0030116 A1 Feb. 12, 2004

Related U.S. Application Data

(63) Continuation of application No. 09/602,787, filed on Jun. 23, 2000, now Pat. No. 6,696,561.

(60) Provisional application No. 60/141,031, filed on Jun. 25, 1999.

(30) Foreign Application Priority Data

| Jul. 8, 1999 | (DE) | 199 31 454 |
|---|---|---|
| Jul. 8, 1999 | (DE) | 199 31 478 |
| Jul. 8, 1999 | (DE) | 199 31 563 |
| Jul. 9, 1999 | (DE) | 199 32 122 |
| Jul. 9, 1999 | (DE) | 199 32 124 |
| Jul. 9, 1999 | (DE) | 199 32 125 |
| Jul. 9, 1999 | (DE) | 199 32 128 |
| Jul. 9, 1999 | (DE) | 199 32 180 |
| Jul. 9, 1999 | (DE) | 199 32 182 |
| Jul. 9, 1999 | (DE) | 199 32 190 |
| Jul. 9, 1999 | (DE) | 199 32 191 |
| Jul. 9, 1999 | (DE) | 199 32 209 |
| Jul. 9, 1999 | (DE) | 199 32 212 |
| Jul. 9, 1999 | (DE) | 199 32 227 |
| Jul. 9, 1999 | (DE) | 199 32 228 |
| Jul. 9, 1999 | (DE) | 199 32 229 |
| Jul. 9, 1999 | (DE) | 199 32 230 |
| Jul. 14, 1999 | (DE) | 199 32 927 |
| Jul. 14, 1999 | (DE) | 199 33 005 |
| Jul. 14, 1999 | (DE) | 199 33 006 |
| Aug. 27, 1999 | (DE) | 199 40 764 |
| Aug. 27, 1999 | (DE) | 199 40 765 |
| Aug. 27, 1999 | (DE) | 199 40 766 |
| Aug. 27, 1999 | (DE) | 199 40 830 |
| Aug. 27, 1999 | (DE) | 199 40 831 |
| Aug. 27, 1999 | (DE) | 199 40 832 |
| Aug. 27, 1999 | (DE) | 199 40 833 |
| Aug. 31, 1999 | (DE) | 199 41 378 |
| Aug. 31, 1999 | (DE) | 199 41 379 |
| Aug. 31, 1999 | (DE) | 199 41 395 |
| Sep. 3, 1999 | (DE) | 199 42 077 |
| Sep. 3, 1999 | (DE) | 199 42 078 |
| Sep. 3, 1999 | (DE) | 199 42 079 |
| Sep. 3, 1999 | (DE) | 199 42 088 |

(51) Int. Cl.
C12N 15/67 (2006.01)
C12N 15/31 (2006.01)
C12N 15/63 (2006.01)
C12N 1/21 (2006.01)

(52) U.S. Cl. .............. 435/41; 435/69.1; 435/252.1; 435/320.1; 536/23.7

(58) Field of Classification Search .................. None
See application file for complete search history.

(56) References Cited

FOREIGN PATENT DOCUMENTS

| EP | 0204326 A2 | 12/1986 |
|---|---|---|
| EP | 0252558 A2 | 1/1988 |
| EP | 0358940 A1 | 3/1990 |
| EP | 0752472 B1 | 1/1997 |
| EP | 0786519 A2 | 7/1997 |
| JP | 62232392 | 10/1987 |
| JP | 62244382 | 10/1987 |
| JP | 04278088 | 10/1992 |
| JP | 04330284 | 11/1992 |
| JP | 05030977 | 2/1993 |
| JP | 05056782 | 3/1993 |
| JP | 05076352 | 3/1993 |
| JP | 05184366 | 7/1993 |

(Continued)

OTHER PUBLICATIONS

Ankri, Serge, et al., "Mutations in the *Corynebacterium glutamicum* Proline Biosynthetic Pathway: a Natural Bypass of the *proA* Step," *Journal of Bacteriology*, vol. 178(15):4412-4419.

(Continued)

Primary Examiner—John S Brusca
(74) Attorney, Agent, or Firm—Lahive & Cockfield, LLP; Elizabeth A. Hanley; Maria Laccotripe Zacharakis

(57) ABSTRACT

Isolated nucleic acid molecules, designated MCT nucleic acid molecules, which encode novel MCT proteins from *Corynebacterium glutamicum* are described. The invention also provides antisense nucleic acid molecules, recombinant expression vectors containing MCT nucleic acid molecules, and host cells into which the expression vectors have been introduced. The invention still further provides isolated MCT proteins, mutated MCT proteins, fusion proteins, antigenic peptides and methods for the improvement of production of a desired compound from *C. glutamicum* based on genetic engineering of MCT genes in this organism.

28 Claims, No Drawings

FOREIGN PATENT DOCUMENTS

| | | |
|---|---|---|
| JP | 05184371 | 7/1993 |
| JP | 05284970 | 11/1993 |
| JP | 05284972 | 11/1993 |
| JP | 05344881 | 12/1993 |
| JP | 05344893 | 12/1993 |
| JP | 06062866 | 3/1994 |
| JP | 06169780 | 6/1994 |
| JP | 06261766 | 9/1994 |
| JP | 06277067 | 10/1994 |
| JP | 06277073 | 10/1994 |
| JP | 07031476 | 2/1995 |
| JP | 07031478 | 2/1995 |
| JP | 07075578 | 3/1995 |
| JP | 07075579 | 3/1995 |
| JP | 09028391 | 2/1997 |
| JP | 09070291 | 3/1997 |
| JP | 09224661 | 9/1997 |
| WO | WO-9519442 A1 | 7/1995 |

OTHER PUBLICATIONS

Billman-Jacobe, H., "Nucleotide sequence of a *recA* gene from *Cornybacterium glutamicum*," *The Journal of Sequencing and Mapping*, vol. 4:403-404 (1994).

Bonamy, Celine, et al., "Identification of IS1206, a *Corynebacterium glutamicum* IS3-related insertion sequence and phylogenetic analysis," *Molecular Microbiology*, vol. 14(3):571-581 (1994).

Bonnassie, S., et al., "Nucleotide sequence of the *dapA* gene from *Corynebacterium glutamicum*," *Nucleic Acids Research*, vol. 18(21):6421 (1990).

Börmann, E.R., et al., "Molecular analysis of the *Corynebacterium glutamicum gdh* gene encoding glutamate dehydrogenase," *Molecular Microbiology*, vol. 6(3):317-326 (1992).

Chen, Chian-Chi, et al., "The cloning and nucleotide sequence of a *Corynebacterium glutamicum* 3-deoxy-D-arabinoheptulosonate-7-phosphate synthase gene," *FEMS Micrkobiology Letters*, vol. 107:223-230 (1993).

Cianciotto, Nicholas, et al., "DNA sequence homology between attB-related sites of *Corynebacterium diphtheriae*, *Corynebacterium ulcerans*, *Corynbacterium glutamicum*, and the *attP* site of γ-Corynephage," *FEMS Microbiology Letters*, vol. 66:299-302 (1990).

Correia, Antonio, et al., "Cloning and characterization of an IS-like element present in the genome of *Brevibacterium lactofermentum* ATCC 13869," *Gene*, vol. 170:91-94 (1996).

Dusch, Nicole, et al., "Expression of the *Corynebacterium glutamicum panD* Gene Encoding L-Aspartate-α-Decarboxylase Leads to Pantothenate Overproduction in *Escherichia coli*," *Applied and Environmental Microbiology*, vol. 65(4):1530-1539 (1999).

Eikmanns, Bernhard J., et al., "Nucleotide sequence, expression and transcriptional analysis of the *Corynebacterium glutamicum gltA* gene encoding citrate synthase," *Microbiology*, vol. 140:1817-1828 (1994).

Eikmanns, Bernhard J., "Identification, Sequence Analysis, and Expression of a *Corynebacterium glutamicum* Gene Cluster Encoding the three Glycolytic Enzymes Glyceraldehyde-3-Phosphate Dehydrogenase, 3-Phosphoglycerate Kinase, and Triosephosphate Isomerase," *Journal of Bacteriology*, vol. 174(19):6076-6086 (1992).

Eikmanns, Bernhard J., et al., "Cloning, Sequence Analysis, Expression, and Inactivation of the *Corynebacterium glutamicum icd* Gene Encoding Isocitrate Dehydrogenase and Biochemical Characterization of the Enzyme," *Journal of Bacteriology*, vol. 177(3):774-782 (1995).

Eikmanns, Bernhard J., et al., "The phosphoenolpyruvate carboxylase gene of *Corynebacterium glutamicum*: Molecular cloning, nucleotide sequence, and expression," *Mol. Gen. Genet.*, vol. 218:330-339 (1989).

Fitzpatrick, R., et al., "Construction and characterization of *recA* mutant strains of *Corynebacterium glutamicum* and *Brevibacterium lactofermentum*," *Appl. Microbiol. Biotechnol.*, vol. 42:575-580 (1994).

Follettie, Max T., et al., "Molecular Cloning and Nucleotide Sequence of the *Corynebacterium glutamicum pheA* Gene," *Journal of Bacteriology*, vol. 167(2):695-702 (1986).

Fouet, Agnes, et al., "*Bacillus subtilis* sucrose-specific enzyme II of the phosphotransferase system: Expression in *Escherichia coli* and homology to enzymes II from enteric bacteria," *Proc. Natl. Acad. Sci.*, vol. 84:8773-8777 (1987).

Han, K.-S., et al., "The molecular structure of the *Corynebacterium glutamicum* threonine synthase gene," *Molecular Microbiology*, vol. 4(10):1693-1702 (1990).

Heery, D.M., et al., "Nucleotide sequence of the *Corynebacterium glutamicum trpE* gene," *Nucleic Acids Research*, vol. 18(23):7138 (1990).

Heery, D.M., et al., "Cloning of the trp Gene Cluster from a Tryptophan-Hyperproducing Strain of *Corynebacterium glutamicum*: Identification of a Mutation in the trp Leader Sequence," *Applied and Environmental Microbiology*, vol. 59(3):791-799 (1993).

Heery, David M., et al., "A Sequence from a Tryptophan-Hyperproducing Strain of *Corynebacterium glutamicum* Encoding Resistance to 5-Methyltryptophan," *Biochemical and Biophysical Research Communications*, vol. 201(3):1255-1262 (1994).

Honrubia, M.P., et al., "Identification, characterization, and chromosomal organization of the *ftsZ* gene from *Brevibacterium lactofermentum*," *Mol. Gen. Genet.*, vol. 259:97-104 (1998).

Ishino, Shuichi, et al., "Nucleotide sequence of the meso-diaminopimelate D-dehydrogenase gene from *Corynebacterium glutamicum*," *Nucleic Acids Research*, vol. 15(9):3917 (1987).

Jäger, Wolfgang, et al., "A *Corynebacterium glutamicum* Gene Conferring Multidrug Resistance in the Heterologous Host *Escherichia coli*," *Journal of Bacteriology*, vol. 179(7):2449-2451 (1997).

Jäger, Wolfgang, et al., "A *Corynebacterium glutamicum* gene encoding a two-domain protein similar to biotin carboxylases and biotin-carboxyl-carrier proteins," *Arch. Microbiol*, vol. 166:76-82 (1996).

Jakoby, Marc, et al., "Isolation of the *Corynebacterium glutamicum glnA* gene encoding glutamine synthetase I," *FEMS Microbiology Letters*, vol. 154:81-88 (1997).

Jakoby, Marc, et al., "Nitrogen regulation in *Corynebacterium glutamicum*: isolation of genes involved and biochemical characterization of corresponding proteins," *FEMS Microbiology Letters*, vol. 173:303-310 (1999).

Jetten, Mike S., et al., "Structural and Functional Analysis of Pyruvate Kinase from *Corynebacterium glutamicum*," *Applied and Environmental Microbiology*, vol. 60(7):2501-2507 (1994).

Joliff, G., et al., "Cloning and nucleotide sequence of the *csp1* gene encoding PS1, one of the two major secreted proteins of *Corynebacterium glutamicum*: the deduced N-terminal region of PS1 is similar to the *Mycobacterium* antigen 85 complex," *Molecular Microbiology*, vol. 6(16):2349-2362 (1992).

Kalinowski, J., et al., "Genetic and biochemical analysis of the aspartokinase from *Corynebacterium glutamicum*," *Molecular Microbiology*, vol. 5(5):1197-1204 (1991).

Kalinowski, Jörn, et al., "Aspartokinase gene *lysCχ* and *lysCβ* overlap and are adjacent to the aspartate β-semialdehyde dehydrogenase gene a*sd* in *Corynebacterium glutamicum*," *Mol. Gen. Genet.*, vol. 224:317-324 (1990).

Keilhauer, Carmen, et al., "Isoleucine Synthesis in *Corynebacterium glutamicum*: Molecular Analysis of the *ilvB-ilvN-itvC* Operon," *Journal of Bacteriology*, vol. 175(17):5595-5603 (1993).

Kimura, Eiichiro, et al., "Molecular Cloning of a Novel Gene, *dtsR*, Which Rescues the Detergent Sensitivity of a Mutant Derived from *Brevibacterium lactofermentum*," *Biosci. Biotech. Biochem.*, vol. 60(10):1565-1570 (1996).

Kobayashi, Miki, et al., "Cloning, Sequencing, and Characterization of the *ftsZ* Gene from Coryneform Bacteria," *Biochemical and Biophysical Research Communications*, vol. 236:383-388 (1997).

Kronemeyer, Wolfgang, et al., "Structure of the *gluABCD* Cluster Encoding the Glutamate Uptake system of *Corynebacterium glutamicum*," *Journal of Bacteriology*, vol. 177(5):1152-1158 (1995).

Lee, Heung-Shick, et al., "Molecular Characterization of AceB, a Gene Encoding Malate Synthase in *Corynebacterium glutamicum*," *Journal of Microbiology and Biotechnology*, vol. 4(4):256-263 (1994).

Le Marrec, Claire, et al., "Genetic Characterization of Site-Specific Integration Functions of ϕAAU2 Infecting '*Arthrobacter aureus*' C70," *Journal of Bacteriology*, vol. 178(7):1996-2004 (1996).

Lepiniec, Loïc, et al., "*Sorghum* phosphoenolpyruvate carboxylase gene family: structure, function and molecular evolution," *Plant Molecular Biology*, vol. 21:487-502 (1993).

Lichtinger, Thomas, et al., "Biochemical and Biophysical Characterization of the Cell Wall Porin of *Corynebacterium glutamicum*: The Channel Is Formed by a Low Molecular Mass Polypeptide," *Biochemistry*, vol. 37:15024-15032 (1998).

Ludwig, W., et al., "Phylogenetic relationships of *Bacteria* based on comparative sequence analysis of elongation factor Tu and ATP-synthase β-subunit genes," *Antonie van Leeuwenhoek*, vol. 64:285-305 (1993).

Malubres, Marcos, et al., "Analysis said Expression of the *thrC* Gene of *Brevibacterium lactofermentum* and Characterization of the Encoded Threonine Synthase," *Applied and Environmental Microbiology*, vol. 60(7):2209-2219 (1994).

Marcel, T., et al., "Nucleotide sequence and organization of the upstream region of the *Corynebacterium glutamicum lysA* gene," *Molecular Microbiology*, vol. 4(11):1819-1830 (1990).

Mateos, Luis M., et al., "Nucleotide sequence of the homoserine kinase (*thr* B) gene of *Brevibacterium lactofermentum*," *Nucleic Acids Research*, vol. 15(9):3922 (1987).

Mateos, Luis M., et al., "Nucleotide sequence of the homoserine dehydrogenase (*thr* A) gene of *Brevibacterium lactofermentum*," *Nucleic Acids Research*, vol. 15(24):10598 (1987).

Matsui, Kazuhiko, et al., "Complete nucleotide and deduced amino acid sequences of the *Brevibacterium lactofermentum* tryptophan operon," *Nucleic Acids Research*, vol. 14(24):10113-10114 (1986).

Möckel, Bettina, et al., "Functional and Structural Analyses of Threonine Dehydratase from *Corynebacterium glutamicum*," *Journal of Bacteriology*, vol. 174(24):8065-8072 (1992).

Molenaar, Douwe, et al., "Biochemical and genetic characterization of the membrane-associated malate dehydrogenase (acceptor) from *Corynebacterium glutamicum*," *Eur. J. Biochem.*, vol. 254:395-403 (1998).

Moreau, Sylvia, et al., "Site-specific integration of corynephage ϕ16: construction of an integration vector," *Microbiology*, vol. 145:539-548 (1999).

Moreau, Sylvie, et al., "Analysis of the Integration Functions of ϕ304L: An Integrase Module among Corynephages," *Virology*, vol. 255:150-159 (1999).

O'Gara, James P., et al., "Mutations in the *trpD* Gene of *Corynebacterium glutamicum* Confer 5-Methyltryptophan Resistance by Encoding a Feedback-Resistant Anthranilate Phosphoribosyltransferase," *Applied and Environmental Microbiology*, vol. 61(12):4477-4479 (1995).

Oguiza, José A., et al., "A Gene Encoding Arginyl-tRNA Synthetase Is Located in the Upstream Region of the lysA Gene in *Brevibacterium lactofermentum*: Regulation of *argS-lysA* Cluster Expression by Arginine," *Journal of Bacteriology*, vol. 175(22):7356-7362 (1993).

Oguiza, José A., et al., "Molecular Cloning, DNA Sequence Analysis, and Characterization of the *Corynebacterium diphtheriae dtxR* Homolog from *Brevibacterium lactofermentum*," *Journal of Bacteriology*, vol. 177(2):465-467 (1995).

Oguiza, José A., et al., "Multiple Sigma Factor Genes in *Brevibacterium lactofermentum*: Characterization of *sigA* and *sigB*," *Journal of Bacteriology*, vol. 178(2):550-553 (1996).

Oguiza, José A., et al., "The galE gene encoding the UDP-galactose 4-epimerase of *Brevibacterium lactofermentum* is coupled transcriptionally to the *dmdR* gene," *Gene*, vol. 177:103-107 (1996).

O'Regan, Michael, et al., "Cloning and nucleotide sequence of the phosphoenolpyruvate carboxylase-coding gene of *Corynebacterium glutamicum* ATCC13032," *Gene*, vol. 77:237-251 (1989).

Park, Soo-Dong, et al., "Isolation and Analysis of *metA*, a Methionine Biosynthetic Gene Encoding Homoserine Acetyltransferase in *Corynebacterium glutamicum*," *Mol. Cells*, vol. 8(3):286-294 (1998).

Park, Yong-Ha, et al., "Phylogenetic Analysis of the Coryneform Bacteria by 5S rRNA Sequences," *Journal of Bacteriology*, vol. 169(5):1801-1806 (1987).

Pascual, Cristina, et al., "Phylogenetic Analysis of the Genus *Corynebacterium* Based on 16S rRNA Gene Sequences," *International Journal of Systematic Bacteriology*, vol. 45(4):724-728 (1995).

Pátek, M., et al., "Analysis of the *leuB* gene from *Corynebacterium glutamicum*," *Appl Microbiol Biotechnol*, vol. 50:42-47 (1998).

Pátek, Miroslav, et al., "Leucine Synthesis in *Corynebacterium glutacium*: Enzyme Activities, Structure of *leuA*, and Effect of *leuA* Inactivation on Lysine Synthesis," *Applied and Environmental Microbiology*, vol. 60(1):133-140 (1994).

Pátek, Miroslav, et al., "Promoters from *Corynebacterium glutamicum*: cloning, molecular analysis and search for a consensus motif," *Microbiology*, vol. 142:1297-1309 (1996).

Pátèk, M., et al., "Identification and transcriptional analysis of the *dapB*-ORF2-*dapA*-ORF4 operon of *Corynebacterium glutamicum*, encoding two enzymes involved in L-lysine synthesis," *Biotechnology Letters*, vol. 19(11):1113-1117 (1997).

Peoples, O.P., et al., "Nucleotide sequence and fine structural analysis of the *Corynebacterium glutamicum hom-thrB* operon," *Molecular Microbiology*, vol. 2(1):63-72 (1988).

Peter, Heidi, et al., "*Corynebacterium glutamicum* Is Equipped with Four Secondary Carriers for Compatible Solutes: Identification, Sequencing, and Characterization of the Proline/Ectoine Uptake System, ProP, and the Ectoine/Proline/Glycine Betaine Carrier, EctP," *Journal of Bacteriology*, vol. 180(22):6005-6012 (1998).

Peter, Heidi, et al., "Isolation of the *putP* gene of *Corynebacterium glutamicum* and characterization of a low-affinity uptake system for compabitle solutes," *Arch Microbiol*, vol. 168:143-151 (1997).

Peter, Heidi, et al., "Isolation, Characterization, and Expression of the *Corynebacterium glutamicum betP* Gene, Encoding the Transport System for the Compatible Solute Glycine Betaine," *Journal of Bacteriology*, vol. 178(17):5229-5234 (1996).

Peters-Wendisch, Petra G., et al., "Pyruvate carboxylase from *Corynebacterium glutamicum*: characterization, expression and inactivation of the *pyc* gene," *Microbiology*, vol. 144:915-927 (1998).

Peyret, J.L., et al., "Characterization of the *cspB* gene encoding PS2, an ordered surface-layer protein in *Corynebacterium glutamicum*," *Molecular Biology*, vol. 9(1):97-109 (1993).

Pisabarro, Agustin, et al., "A Cluster of Three Genes (*dapA, orf2, and dapB*) of *Brevibacterium lactofermentum* Encodes Dihydrodipicolinate Synthase, Dihydrodipicolinage Reductase, and a Third Polypeptide of Unknown Function," *Journal of Bacteriology*, vol. 175(9):2743-2749 (1993).

Rainey, Frederick A., et al., "Phylogenetic analysis of the genera *Rhodococcus* and *Nocardia* and evidence for the evolutionary origin of the genus *Nocardia* from within the radiation of *Rhodococcus* species," *Microbiology*, vol. 141:523-528 (1995).

Ramos, Adoración, et al., "Cloning, sequencing and expression of the gene encoding elongation factor P in the amino-acid producer *Brevibacterium lactofermentum* (*Corynebacterium glutamicum* ATCC 13869)," *Gene*, vol. 198:217-222 (1997).

Reinscheid, Dieter, J., et al., "Cloning, sequence analysis, expression and inactivation of the *Corynebacterium glutamicum pta-ack* operon encoding phosphotransacetylase and acetate kinase," *Microbiology*, vol. 145:503-515 (1999).

Reinscheid, Dieter J., et al., "Characterization of the Isocitrate Lyase Gene from *Corynebacterium glutamicum* and Biochemical Analysis of the Enzyme," *Journal of Bacteriology*, vol. 176(12):3474-3483 (1994).

Reinscheid, Dieter J., et al., "Malate synthase from *Corynebacterium glutamicum*: sequence analysis of the gene and biochemical characterization of the enzyme," *Microbiology*, vol. 140:3099-3108 (1994).

Roller, Carsten, et al., "Gram-positive bacteria with a high DNA G+C content are characterized by a common insertion within their 23S rRNA genes," *Journal of General Microbiology*, vol. 138:1167-1175 (1992).

Rossol, Ingrid, et al., "The *Corynebacterium glutamicum* aecD Gene Encodes a C-S Lyase with α,β-Elimination Activity That Degrades Aminoethylcysteine," *Journal of Bacteriology*, vol. 174(9):2968-2977 (1992).

Ruimy, Raymond, et al., "Phylogeny of the Genus Corynebacterium Deduced from Analyses of Small-Subunit Ribosomal DNA Sequences," *International Journal of Systematic Bacteriology*, vol. 45(4):740-746 (1995).

Sahm, Hermann, et al., "D-Pantothenate synthesis in *Corynebacterium glutamicum* and Use of *panBC* and Genes Encoding L-Valine synthesis for D-Pantothenate Overproduction", *Applied and Environmental Microbiology*, vol. 65(5):1973-1979 (1999).

Sakanyan, Vehary, et al., "Genes and enzymes of the acetyl cycle of arginine biosynthesis in *Corynebacterium glutamicum*: enzyme evolution in the early steps of the arginine pathway," *Microbiology*, vol. 142:99-108 (1996).

Sano, Konosuke, et al., "Structure and function of the *trp* operon control regions of *Brevibacterium lactofermentum*, a glutamic-acid-producing bacterium," *Gene*, vol. 53:191-200 (1987).

Schäfer, Andreas, et al., "Cloning and Characterization of a DNA Region Encoding a Stress-Sensitive Restriction System from *Corynebacterium glutamicum* ATCC 13032 and Analysis of Its Role in Intergeneric Conjugation with *Escherichia coli*," *Journal of Bacteriology*, vol. 176(23):7309-7319 (1994).

Seep-Feldhous, A.J., et al., "Molecular analysis of the *Corynebacterium glutamicum lysI* gene involved in lysine uptake," *Molecular Microbiology*, vol. 5(12):2995-3005 (1991).

Serebrijski, I, et al., "Multicopy Suppression by *asd* Gene and Osmotic Stress-Dependent Complementation by Heterologous *proA* in *proA* Mutants," *Journal of Bacteriology*, vol. 177(24):7255-7260 (1995).

Serebriiskii, Ilya G., et al., "Two new members of the BioB superfamily: cloning, sequencing and expression of *bioB* genes of *Methylobacillus flagellatum* and *Corynebacterium glutamicum*," *Gene*, vol. 175:15-22 (1996).

Siewe, Ruth M. et al, "Functional and Genetic Characterization of the (Methyl)ammonium Uptake Carrier of *Corynebacterium glutamicum*," *The Journal of Biological Chemistry*, vol. 271(10):5398-5403 (1996).

Usuda, Yoshihiro, et al., "Molecular cloning of the *Corynebacterium glutamicum* ('*Brevibacterium lactofermentum*' AJ12036) *odhA* gene encoding a novel type of 2-oxoglutarate dehydrogenase," *Microbiology*, vol. 142:3347-3354 (1996).

Vertès, Alain A., et al., "Isolation and characterization of IS*31831*, a transposable element from *Corynebacterium glutamicum*," *Molecular Microbiology*, vol. 11(4):739-746 (1994).

von der Osten, C.H., et al., "Molecular cloning, nucleotide sequence and fine-structural analysis of the *Corynebacterium glutamicum fda* gene: structural comparison of *C. glutamicum* fructose-1,6-biphoshpate aldolase to class I and class II aldolases," *Molecular Microbiology*, vol. 33(11):1625-1637 (1989).

Vrljic, Marina, et al., "A new type of transporter with a new type of cellular function: L-lysine export from *Corynebacterium glutamicum*," *Molecular Microbiology*, vol. 22(5):815-826 (1996).

Wachi, M., et al., "A *murC* gene from coryneform bacteria," *Appl Microbiol Biotechnol*, vol. 51:223-228 (1999).

Wehmeier, Lutz, et al., "The role of the *Corynebacterium glutamicum rel* gene in (p)ppGpp metabolism," *Microbiology*, vol. 144:1853-1862 (1998).

Wehrmann, Axel, et al., "Different Modes of Diaminopimelate Synthesis and Their Role in Cell Wall Integrity: A Study with *Corynebacterium glutamicum*," *Journal of Bacteriology*, vol. 180(12):3159-3165 (1998).

Wehrmann, Axel, et al., "Analysis of different DNA fragments of *Corynebacterium glutamicum* complementing dapE of *Escherichia coli*," *Microbiology*, vol. 140:3349-3356 (1994).

Wehrmann, Axel, et al., "Functional Analysis of Sequences Adjacent ot *dapE* of *Corynebacterium glutamicum* Reveals the Presence of *aroP*, Which Encodes the Aromatic Amino Acid Transporter," *Journal of Bacteriology*, vol. 177(20):5992-5993 (1995).

Yeh, Patrice, et al., "Nucleotide sequence of the *lysA* gene *Corynebacterium glutamicum* and possible mechanisms for modulation of its expression," *Mol Gen Genet*, vol. 212:112-119 (1988).

GenBank Accession No. A09073 for DNA fragment coding for phosphoenolpyruvat corboxylase, recombinant DNA carrying said fragment, strains carrying the recombinant DNA and method for producing L-amino acids using said strains, Bachmann, B. et al, Apr. 14, 2005.

GenBank Accession No. A45579 for Production of L-isoleucine by means of recombinant micro-organisms with deregulated threonine dehydratase, Moeckel, B. et al, Mar. 7, 1997.

GenBank Accession No. A45581, Moeckel, B. et al, "Production of L-Isoleucine by Means of Recombinant Micro-Organisms with Deregulated Threonine Dehydratase." Mar. 7, 1997.

GenBank Accession No. A45583, Moeckel, B. et al, "Production of L-Isoleucine by Means of Recombinant Micro-Organisms with Deregulated Threonine Dehydratase." Mar. 7, 1997.

GenBank Accession No. A45585, Moeckel, B. et al, "Production of L-Isoleucine by Means of Recombinant Micro-Organisms with Deregulated Threonine Dehydratase." Mar. 7, 1997.

GenBank Accession No. A45587 for Production of L-isoleucine by means of recombinant micro-organisms with deregulated threonine dehydratase, Moeckel, B. et al. Mar. 7, 1997.

GenBank Accession No. AA011641 for Generation and analysis of 280,000 human expressed sequence tags, Hillier, L. et al, May 9, 1997.

GenBank Accession No. AA655226 for The WashU-HHMI Mouse EST Project, Marra, M. et al, Nov. 4, 1997.

GenBank Accession No. AA704727 for WashU-NCI human EST Project, Hillier, L. et al, Dec. 24, 1997.

GenBank Accession No. AB003132 for Cloning, sequencing, and characterization of the ftsZ gene from coryneform bacteria, Kobayashi, M. et al, Aug. 4, 1997.

GenBank Accession No. AB015023 for A murC gene from coryneform bacteria, Wachi, M. et al, Dec. 15, 2001.

GenBank Accession No. AB015853 for Expression in *Escherichia coli* of a new multidrug efflux pump, MexXY, from *Pseudomonas aeruginosa*, Mine, T. et al, Aug. 2, 2000.

GenBank Accession No. AB018530 for Molecular cloning of a novel gene, dtsR, which rescues the detergent sensitivity of a mutant derived from *Brevibacterium lactofermentum*, Kimura, E. et al, Oct. 16, 1998.

GenBank Accession No. AB018531 for The role of DtsR2 in the glutamate-production in coryneform bacteria, Kimura, E. et al, Oct. 16, 1998.

GenBank Accession No. AB020624 for Isolation of the murl gene from *Brevibacterium lactofermentum* ATCC 13869 encoding D-glutamate racemase, Malathi, K.C. et al, Jul. 24, 1999.

GenBank Accession No. AB023377 for Nucleotide sequence of the *Corynebacterium glutamicum* transketotase gene, Ikeda, M. et al, 02/20/9.

GenBank Accession No. AB024708 for *Corynebacterium glutamicum* gltBD gene, Kanno, S. et al, Mar. 13, 1999.

GenBank Accession No. AB025424 for *Brevibacterium lactofermentum* ATCC 13869 acn gene for Aconitase, Nakamura, J. et al, Apr. 3, 1999.

GenBank Accession No. AB027714 for Cryptic plasmid pCG1 of *Corynebacterium glutamicum*, Yonetani, Y. et al, Jun. 1, 1999.

GenBank Accession No. AB027715 for Plasmid pCG11 of *Corynbacterium glutamicum*, Yonetani, Y. et al, Jun. 1, 1999.

GenBank Accession No. AC004295 for Sequencing of Drosophila chromosome 2R, region 55C1-55C4, Celniker, S.E. et al, Jul. 29, 1998.

GenBank Accession No. AC005019 for Toward a complete human genome sequence, Sulston, J.E. et al, Oct. 15, 2003.

GenBank Accession No. AC006044 for Toward a complete human genome sequence, Sulston, J.E. et al, Oct. 8, 2003.
GenBank Accession No. AC006474 for The DNA sequence of human chromosome 7, Hillier, L.W. et al, Jan. 27, 2004.
GenBank Accession No. AC007084 for Sequencing of Drosophila chromosome 2R, region 43F-44A, Celniker, S.E. et al, Mar. 21, 2001.
GenBank Accession No. AC007739 for The sequence of *Homo sapiens* BAC clone RP11-91L3, Hou, S. et al, Apr. 16, 2005.
GenBank Accession No. AC00843, DOE Joint Genome Institute and Stanford Human Genome Center, for *Homo sapiens* chromosome 19 clone CTC-273B12, complete sequence, Mar. 22, 2003.
GenBank Accession No. AC009298 for The sequence of *Homo sapiens* BAC clone RP11-1716, Nguyen, C. et al, Apr. 15, 2005.
GenBank Accession No. AC010187 for *Homo sapiens* chromosome 12 clone RP11-38909, Working Draft Sequence, 40 unordered pieces, Muzny, D.M. et al, Jan. 8, 2003.
GenBank Accession No. AC011647 for *Homo sapiens* chromosome 11, clone RP11-15D18, Birren, B. et al, Jun. 18, 2002.
GenBank Accession No. AD000016 for *Mycobacterium tuberculosis*, Du, L., Dec. 3, 1996.
GenBank Accession No. AD000002 for *Mycobacterium tuberculosis*, Du, L., Dec. 10, 1006.
GenBank Accession No. AE000654 for The complete genome sequence of the gastric pathogen *Helicobacter pylori*, Tomb, J.-F. et al, Apr. 6, 1999.
GenBank Accession No. AF001552 for Genome duplications and other features in 12 Mb of DNA sequence from human chromosome 16p ang 16q, Loftus, B.J. et al, Jan. 1, 2000.
GenBank Accession No. AF005242, Chun, J.Y. et al, "Molecular cloning and analysis of the argC gene from *Corynebacterium glutamicum*," *Biochem. Mol. Biol. Int.*, vol. 46(3):437-447 (1998), Jul. 23, 2001.
GenBank Accession No. AF005635 for *Corynebacterium glutamicum*, Reid, S.J. et al, Jun. 14, 1999.
GenBank Accession No. AF030405 for Molecular cloning of the histidine biosynthetic genes from *Corynebacterium glutamicum*, Jung, S.I. et al, Nov. 13, 1997.
GenBank Accession No. AF030520, Ko, S.Y. et al, "Molecular cloning of the argG gene from *Corynebacterium glutamicum*." Nov. 19, 1997.
GenBank Accession No. AF031518, Chun, J.Y. et al, "Cloning of the argF gene encoding the ornithine carbamoyltransferase from *Corynebacterium glutamicum*," *Mol. Cells*, vol. 9(3):333-337 (1999), Jun. 13, 2001.
GenBank Accession No. AF036932 for Molecular cloning of the aroD gene from *Corynebacterium glutamicum*, Park, K.-Y. et al, Dec. 13, 1997.
GenBank Accession No. AF038548 for Sequence of the *Corynebacterium glutamicum* pyruvate carboxylase gene, Koffas, M.A. et al, Aug. 25, 2000.
GenBank Accession No. AF038651 for The role of the *Corynebacterium glutamicum* rel gene in (p)ppGpp metabolism, Wehmeier, L. et al, Mar. 15, 2001.
GenBank Accession No. AF041436, Ko. S.-Y. et al, "The argR gene of *Corynebacterium glutamicum*." Jan. 5, 1999.
GenBank Accession No. AF045998 for Molecular cloning of the histidine biosynthetic genes from *Corynebacterium glutamicum*, Jund, S.I. et al, Feb. 19, 1998.
GenBank Accession No. AF048764, Park. M.Y. et al, "Molecular cloning of the argH gene encoding argininosuccinate lyase from *Corynebacterium glutamicum*." Jul. 1, 1998.
GenBank Accession No. AF049897, Park, M.Y. et al, "Molecular cloning of the Arginine Biosynthetic Gene from *Corynebacterium glutamicum*." Jul. 1, 1998.
GenBank Accession No. AF050109 for The function of the inhA gene in mycolic acid synthesis of *Corynebacterium glutamicum*, Sayyada-Hafeez, A. et al, Nov. 19, 2002.
GenBank Accession No. AF050166, Kwon, J.H. et al, "Cloning of the histidine biosynthetic genes from *Corynebacterium glutamicum*: organization and analysis of the hisG and hisE genes," *Can. J. Microbiol.*, vol. 46(9):848-855 (2000), Apr. 26, 2002.

GenBank Accession No. AF051846 for *Corynebacterium glutamicum*, Jung, S.I. et al, Mar. 12, 1998.
GenBank Accession No. AF052652 for Isolation and Analysis of metA, a Metionine Biosynthetic Gene Encoding Homoserine Acetyltransferase in *Corynebacterium glutamicum*, Park, S.-D. et al. Mar. 19, 1998.
GenBank Accession No. AF053071 for Cloning and analysis of the aroB gene encoding dehyddroquinate synthase from *Corynebacterium glutamicum*, Han, M.A. et al, Apr. 26, 2002.
GenBank Accession No. AF060558 for *Corynebacterium glutamicum*, Juns, S.I. et al, Apr. 29, 1998.
GenBank Accession No. AF077409, Latreille, P. et al, "The A. thaliana Genome Sequencing Project," Aug. 3, 1998.
GenBank Accession No. AF086704 for *Corynebacterium glutamicum*, Kwon, J.H. et al, Feb. 8, 1999.
GenBank Accession No. AF114233 for Cloning and molecular analysis of the *Corynebacterium glutamicum* ASO19 and aroA gene, O'Donohue, M. et al, Feb. 7, 1999.
GenBank Accession No. AF116184, Dusch, N. et al, "Expression of the *Corynebacterium glutamicum* panD gene encoding L-aspartate-alpha-decarboxylase leads to pantothenate overproduction in *Escherichia coli*," *Appl. Environ. Microbiol.*, vol. 65(4):1530-1539 (1999), May 2, 19999.
GenBank Accession No. AF124518 for The cloning and phylogenetic analysis of the 3-dehydroquinase gene from *Corynebacterium glutamicum*, Joy, J. et al, May 18, 1999.
GenBank Accession No. AF124600 for Genetic aspects of the prechorismate pathway in *Corynebacterium glutamicum*, Burke, K.G. et al, May 4, 1999.
GenBank Accession No. AF145898 for Comparison of inhA gene of *Corynebacterium glutamicum* with its mutants and other related species, Hafeez, S. A. et al, Nov. 19, 2002.
GenBank Accession No. AF145897 for Comparison of inhA gene for *Corynebacterium glutamicum* with its mutants and other related species, Hafeez, S.A. et al, Nov. 19, 2002.
GenBank Accession No. AI190741, NCI-CGAP http://www.ncbi.nlm.nih.gov/ncicqap, for National Cancer Institute, Cancer Genome Anatomy Project (CGAP), Tumor Gene Index, Oct. 28, 1998.
GenBank Accession No. AJ001436 for *Corynebacterium glutamicum* is equipped with four secondary carriers for compatible solutes: identification, sequencing, and characterization of the proline/ectoine uptake system, ProP, and the ectoine/proline/glycine betaine carrier, EctP, Peter, H. et al, Nov. 20, 1998.
GenBank Accession No. AJ004934, Wehrmann, A. et al, "Different modes of diaminopimelate synthesis and their role in cell wall integrity: a study with *Corynebacterium glutamicum*," *J. Bacteriol.*, vol. 180(12):3159-3165 (1998), Jun. 17, 1998.
GenBank Accession No. AJ007732, Jakoby, M.J. et al, "Ammonium uptake in *Corynebacterium glutamicum* is regulated on the level of expression and enzyme activity." Apr. 15, 2005.
GenBank Accession No. AJ010319 for Nitrogen regulation in *Corynebacterium glutamicum*: isolation of genes involved and biochemical characterization of corresponding proteins, Jakoby, M. et al, Apr. 15, 2005.
GenBank Accession No. AJ132968 for Construction and application of new *Corynebacterium glutamicum* vectors, Jakoby, M.J. et al, May 4, 1999.
GenBank Accession No. AJ224946 for Biochemical and genetic characterization of the membrane-associated malate dehydrogenase (acceptor) from *Corynebacterium glutamicum*, Molenaar, D. et al, Aug. 11, 1998.
GenBank Accession No. AJ238250 for Functions of the membrane-associated and cytoplasmic malate dehydrogenases in the citric acid cycle of *Corynebacterium glutamicum*, Molenaar, D. et al, Dec. 3, 2000.
GenBank Accession No. AJ238703 for Biochemical and biophysical characterization of the cell wall porin of *Corynebacterium glutamicum*: the channel is formed by a low molecular mass polypeptide, Lichtinger, T. et al, May 7, 1999.
GenBank Accession No. AL021841, Cole, S.T. et al, "Deciphering the biology of *Mycobacterium tuberculosis* from the complete genome sequence," *Nature*, vol. 393(6685):537-544 (1998), Sep. 2, 2002.

GenBank Accession No. AL022075 for Deciphering the biology of *Mycobacterium tuberculosis* from the complete genome sequence, Cole, S.T. et al, Sep. 2, 2002.

GenBank Accession No. AL022268 for A set of ordered cosmids and a detailed genetic and physical map for the 8 Mb *Streptomyces coelicolor* A3 (2) chromosome, Redenbach, M. et al, May 12, 2002.

GenBank Accession No. AL023591 for Use of an ordered cosmid library to deduce the genomic organization of *Mycobacterium leprae*, Eiglmeier, K. et al, Apr. 16, 2005.

GenBank Accession No. AL035159 for Use of an ordered cosmid library to deduce the genomic organization of *Mycobacterium leprae*, Eiglmeier, K. et al, Apr. 16, 2005.

GenBank Accession No. AL081678 for *Arabidopsis thaliana*, Salanoubat, M. et al, Jun. 28, 1999.

GenBank Accession No. AL096814 for *Homo sapiens*, Sehra, H., May 18, 2005.

GenBank Accession No. AL101527 for *Drosophila melanogaster*, Genoscope, Jul. 26, 1999.

GenBank Accession No. AP000004 for Complete sequence and gene organization of the genome of a hyper-thermophilic archaebacterium, *Pyrococcus horikoshii* OT3, Kawarabayasi, Y. et al, May 27, 2004.

GenBank Accession No. AP000140 for *Homo sapiens* 911,949bp genomic DNA of 21q21.2 (Region: LL56-APP Clone Range: B2291C14-R44F3), Hattori, M. et al, Jan. 8, 2000.

GenBank Accession No. AP000228 for *Homo sapiens* 75,698bp genomic DNA of 21q21.2, Hattori, M. et al, Nov. 20, 1999.

GenBank Accession No. AQ128685 for Sequence-tagged connectors: A sequence approach to mapping and scanning the human genome, Mahairas, G.G. et al, Sep. 23, 1998.

GenBank Accession No. AQ364540 for A BAC End Sequencing Framework to Sequence the Rice Genome, Wing, R.A. et al, Dec. 16, 1999.

GenBank Accession No. AQ463737 for Sequence-tagged connectors: A sequence approach to mapping and scanning the human genome, Mahairas, G.G. et al, Apr. 23, 1999.

GenBank Accession No. B10133 for BAC End Sequences at ATGC, Feng, J. et al, May 14, 1997.

GenBank Accession No. C97772 for Rice cDNA from callus, Sasaki, T. et al, Apr. 4, 2002.

GenBank Accession No. D17429 for Isolation and characterization of IS31831, a transposable element from *Corynebacterium glutamicum*, Vertes, A.A. et al, Feb. 4, 1999.

GenBank Accession No. D84102 for Molecular cloning of the *Corynebacterium glutamicum* ('Brevibacterium lactofermentum' AJ12036) odhA gene encoding a novel type of 2-oxoglutarate dehydrogenase, Usuda, Y. et al, Feb. 6, 1999.

GenBank Accession No. D84432 for Systematic sequencing of the 283 kb 210 degrees-232 degrees region of the *Bacillus subtilis* genome containing the skin element and many sporulation genes, Mizuno, M. et al, Feb. 6, 1999.

GenBank Accession No. D87915 for Molecular cloning and characterization of the obg gene of *Streptomyces griseus* in relation to the onset of morphological differentiation, Okamoto, S. et al, Feb. 7, 1999.

GenBank Accession No. E01358 for Production of L-Thereonine and L-Isoleucine, Katsumata, R. et al, Sep. 29, 1997.

GenBank Accession No. E01359 for Production of L-Thereonine and L-Isoleucine, Katsumata, R. et al, Sep. 29, 1997.

GenBank Accession No. E01375 for Tryptophan operon, peptide and protein coded thereby, utilization of Tryptophan operon gene expression and production of Tryptophan, Matsui, K. et al, Sep. 29, 1997.

GenBank Accession No. E01376 for Tryptophan Operon, Peptide and Protein Coded Thereby, Utilization of Tryptophan Operon Gene Expression and Production of Tryptophan, Matsui, K. et al, Sep. 29, 1997.

GenBank Accession No. E01377 for Tryptophan Operon, Peptide and Protein Coded Thereby, Utilization of Tryptophan Operon Gene Expression and Production of Tryptophan, Matsui, K. et al, Sep. 29, 1997.

GenBank Accession No. E03937 for DNA fragment containing gene capable of coding biotin synthetase and its utilization, Hatakeyama, K. et al, Sep. 29, 1997.

GenBank Accession No. E04040 for Gene Coding Diaminopelargonic Acid Aminotransferase and Desthiobiotin Synthetase and its Utilization, Kohama, K. et al, Sep. 29, 1997.

GenBank Accession No. E04041 for Gene coding Diaminopelargonic Acid Aminotransferase and Desthiobiotin Synthetase and its Utilization, Kohama, K. et al, Sep. 29, 1997.

GenBank Accession No. E04307, Kurusu, Y. et al, "Gene DNA coding aspartase and utilization there." Sep. 29, 1997.

GenBank Accession No. E04376 for Gene Manifestation Controlling DNA, K atsumata, R. et al, Sep. 29, 1997.

GenBank Accession No. E04377 for Gene Manifestation Controlling DNA, Katsumata, R. et al, Sep. 29, 1997.

GenBank Accession No. E04484 for Production of L-Phenylalanine by Fermentation, Sotouchi, N. et al, Sep. 29, 1997.

GenBank Accession No. E05108 for Gene DNA Coding Aspartokinase and its Use, Fugono, N. et al, Sep. 29, 1997.

GenBank Accession No. E05112 for Gene DNA Coding Dihydrodipicolinic Acid Synthetase and its Use, Hatakeyama, K. et al, Sep. 29, 1997.

GenBank Accession No. E05776 for Gene DNA Coding Diaminopimelic Acid Dehydrogenase and its Use, Kobayashi, M. et al, Sep. 29, 1997.

GenBank Accession No. E05779 for Gene DNA Coding Threonine Synthase and its Use, Kohama, K. et al, Sep. 29, 1997.

GenBank Accession No. E06110 for Production of L-Phenylatanine by Fermentation Method, Kikuchi, T. et al, Sep. 29, 1997.

GenBank Accession No. E06111 for Production of L-Phenylalanine by Fermentation Method, Kikuchi, T. et al, Sep. 29, 1997.

GenBank Accession No. E06146 for Gene Capable of Coding Acetohydroxy Acid Synthase and its, Inui, M. et al, Sep. 29, 1997.

GenBank Accession No. E06825 for Mutant Aspartokinase Gene, Sugimoto, M. et al, Sep. 29, 1997.

GenBank Accession No. E06826 for Mutant Aspartokinase Gene, Sugimoto, M. et al, Sep. 29, 1997.

GenBank Accession No. E06827 for Mutant Aspartokinase Gene, Sugimoto, M. et al, Sep. 29, 1997.

GenBank Accession No. E07701 for Gene DNA Participating in Integration of Membraneous Protein to, Honno, N. et al, Sep. 29, 1997.

GenBank Accession No. E08177 for Genetic DNA Capable of Coding Aspartokinase Released from Feedbank Inhibition and its Utilization, Sato, Y. et al, Sep. 29, 1997.

GenBank Accession No. E08178 for Genetic DNA Capable of Coding Aspartokinase Released from Feedback Inhibition and its Utilization, Sato, Y. et al, Sep. 29, 1997.

GenBank Accession No. E08179 for Genetic DNA Capable of Coding Aspartokinase Released from Feedback Inhibition and its Utilization, Sato, Y. et al, Sep. 29, 1997.

GenBank Accession No. E08180 for Genetic DNA Capable of Coding Aspartokinase Released from Feedback Inhibition and its Utilization, Sato, Y. et al, Sep. 29, 1997.

GenBank Accession No. E08181 for Genetic DNA Capable of Coding Aspartokinase Released from Feedback Inhibition and its Utilization, Sato, Y. et al, Sep. 29, 1997.

GenBank Accession No. E08182 for Genetic DNA Capable of Coding Aspartokinase Released from Feedback Inhibition and its Utilization, Sato, Y. et al, Sep. 29, 1997.

GenBank Accession No. E08232 for Gene DNA Coding Acetohydroxy Acid Isomeroreductase, Inui, M. et al, Sep. 29, 1997.

GenBank Accession No. E08234 for Gene DNA Coding for Translocation Machinery of Protein, Asai, Y. et al, Sep. 29, 1997.

GenBank Accession No. E08643 for DNA Fragment Having Promoter Function in Coryneform Bacterium, Hatakeyama, K. et al, Sep. 29, 1997.

GenBank Accession No. E08646 for DNA Fragment Having Promoter Function in Coryneform Bacterium, Hatakeyama, K. et al, Sep. 29, 1997.

GenBank Accession No. E08648, Kohama, K. et al, "DNA fragment having promoter function in coryneform bacterium." Sep. 29, 1997.

GenBank Accession No. E08900 for DNA Fragment Containig Gene Coding Dihyrodipicolinic Acid Reductase and Utilization Thereof, Madori, M. et al, Sep. 29, 1997.

GenBank Accession No. E08901 for DNA Fragment Containing Gene Coding Dihyrodipicolinic Acid Decarboxylase and Utilization Thereof, Madori, M. et al, Sep. 29, 1997.

GenBank Accession No. E12594 for Production of L-Tryptophan, Hatakeyama, K. et al, Sep. 29, 1997.

GenBank Accession No. E12758 for Amplification of Gene Using Artificial Transposon, Moriya, M. et al, Sep. 29, 1997.

GenBank Accession No. E12759 for Amplification of Gene Using Artificial Transposon, Moriya, M. et al, Sep. 29, 1997.

GenBank Accession No. E12760 for Amplification of Gene Using Artificial Transposon, Moriya, M. et al, Sep. 29, 1997.

GenBank Accession No. E12764 for Amplification of Gene Using Artificial Transposon, Moriya, M. et al, Sep. 29, 1997.

GenBank Accession No. E12767 for Amplification of Gene Using Artificial Transposon, Moriya, M. et al, Sep. 29, 1997.

GenBank Accession No. E12770 for Amplification of Gene Using Artificial Transposon, Moriya, M. et al, Sep. 29, 1997.

GenBank Accession No. E12773 for Amplification of Gene Using Artificial Transposon, Moriya, M. et al, Sep. 29, 1997.

GenBank Accession No. E13655 for Glucose-6-Phosphate Dehydrogenase and DNA Capable of Coding the Same, Hatakeyama, K. et al, Apr. 27, 1998.

GenBank Accession No. L01508, Mockel, B. et al, "Functional and structural analyses of threonine dehydratase from *Corynebacterium glutamicum*," *J. Bacteriol.*, vol. 174(24):8065-8072 (1992), Apr. 26, 1993.

GenBank Accession No. L07603 for The cloning and nucleotide sequence of a *Corynebacterium glutamicum* 3-deoxy-D-arabinoheptulosonate-7-phosphate synthase gene, Chen, C.C. et al, Apr. 26, 1993.

GenBank Accession No. L09232 for Isoleucine synthesis in *Corynebacterium glutamicum*: molecular analysis of the ilvB-ilvN-ilvC operon, Keilhauer, C. et al, Feb. 23, 1995.

GenBank Accession No. L18874 for *Bacillus subtilis* sucrose-specific enzyme II of the phosphotransferase system: expression in *Escherichia coli* and homology to enzymes II from enteric bacteria, Fouet, A. et al, Nov. 24, 1994.

GenBank Accession No. L27123 for Molecular characterization of aceB, a gene encoding malate synthase in *Corynebacterium glutamicum*, Lee, H.-S. et al, Jun. 8, 1995.

GenBank Accession No. L27126, Jetten, M.S., "Structural and functional analysis of pyruvate kinase from *Corynebacterium glutamicum*," *Appl. Environ. Microbiol.*, vol. 60(7):2501-2507 (1994), Dec. 7, 1994.

GenBank Accession No. L28760 for Molecular characterisation of acea, a gene encoding isocitrate lyase in *Corynebacterium glutamicum*, Lee, H.-S et al, Feb. 10, 1995.

GenBank Accession No. L35906, Oguiza, J.A., "Molecular cloning, DNA sequence analysis, and characterization of the *Corynebacterium diphtheria* dtxR homolog from *Brevibacterium lactofermentum*," *J. Bacteriol.*, vol. 177(2):465-467 (1995) Mar. 6, 1996.

GenBank Accession No. L78820, Eiglmeier, K. et al, "Use of an ordered cosmid library to deduce the genomic organization of *Mycobacterium laprae*," *Mol. Microbiol.*, vol. 7(2):197-206 (1993) Dec. 17, 2001.

GenBank Accession No. M13774, Follettie, M.T. et al, "Molecular cloning and nucleotide sequence of the *Corynebacterium glutamicum* pheA gene," *J. Bacteriol.*, vol. 167(2):695-702 (1986), Apr. 26, 1993.

GenBank Accession No. M16175 for Phylogenetic analysis of the coryneform bacteria by 5S rRNA sequences, Park, Y.H. et al, Apr. 27, 1993.

GenBank Accession No. M16663 for Structure and function of the trp operon control regions of *Brevibacterium lactofermentum*, a glutamic-acid producting bacterium, Sano, K. et al, Jun. 11, 2001.

GenBank Accession No. M16664 for Structure and function of the trp operon control regions of *Brevibacterium lactofermentum*, a glutamic-acid-productin bacterium, Sano, K. et al, Jun. 11, 2001.

GenBank Accession No. M25819 for Cloning and nucleotide sequence of the phosphoenolpyruvate carboxylase-coding gene of *Corynebacterium glutamicum* ATCC13032, O'Regan, M. et al, Dec. 15, 1995.

GenBank Accession No. M85106 for Gram-positive bacteria with a high DNA G+C content are characterized by a common insertion within their 23S rRNA genes, Roller, C. et al, Apr. 26, 1993.

GenBank Accession No. M85107 for Gram-positive bacteria with a high DNA G+C content are characterized by a common insertion within their 23S rRNA genes, Roller, C. et al, Apr. 26, 1993.

GenBank Accession No. M85108 for Gram-positive bacteria with a high DNA G+C content are characterized by a common insertion within their 23S rRNA genes, Roller, C. et al, Apr. 26, 1993.

GenBank Accession No. M89931, Rossol, I. et al, "*Corynebacterium glutamicum* aecD gene encodes a C-S lyase with alpha, beta-elimination activity that degrades aminoethylcysteine," *J. Bacteriol.*, vol. 174(9):2968-2977 (1992), Feb. 8, 2002.

GenBank Accession No. S59299 for Cloning of the trp gene cluster from a tryptophan-hyperproducing strain of *Corynebacterium glutamicum*: identification of a mutation in the trp leader sequence, Herry, D.M. et al, Apr. 13, 2001.

GenBank Accession No. S76966 for Insertion sequence typing of *Mycobacterium tuberculosis*: characterization of a widespread subtype with a single copy of IS6110, Fomukong, N.G. et al, May 11, 2005.

GenBank Accession No. U00016 for *Mycobacterium leprae*, Smith, D.R. et al, Mar. 1, 2004.

GenBank Accession No. U00018, Smith, D.R., *Mycobacterium laprae*, Smith, D.R. et al, Mar. 1, 2004.

GenBank Accession No. U11545 for Complete nucleotide sequence of the *Corynebacterium glutamicum* ATCC 21850 trpD gene, O'Gara, J.P. et al, Jul. 8, 1994.

GenBank Accession No. U13922 for Cloning and characterization of a DNA region encoding a stress-sensitive restriction system from *Corynebacterium glutamicum* ATCC 13032 and analysis of its role in intergeneric conjugation with *Escherichai coli*, Schafer, A. et al, Feb. 3, 1998.

GenBank Accession No. U14965 for Molecular cloning and characterization of the recA gene from *Corynebacterium glutamicum* ASO19, Kerins, S.M. et al, Feb. 5, 1999.

GenBank Accession No. U31224, Ankri, S. et al, "Mutations in the *Corynebacterium glutamicum* proline biosynethtic pathway: a natural bypass on the proA step," *J. Bacteriol.*, vol. 178(15):4412-4419 (1996), Aug. 2, 1996.

GenBank Accession No. U31225, Ankri, S. et al, "Mutations in the *Corynebacterium glutamicum* proline biosynethtic pathway: a natural bypass of the proA step," *J. Bacteriol.*, vol. 178(15):4412-4419 (1996), Aug. 2, 1996.

GenBank Accession No. U31230, Ankri, S. et al, "Mutations in the *Corynebacterium glutamicum* proline biosynthetic pathway: a natural bypass of th proA step," *J. Bacteriol.*, vol. 178(15):4412-4419 (1996), Aug. 2, 1996.

GenBank Accession No. U31281 for Two new members of the bio B superfamily: cloning, sequencing and expression of bio B genes of Methylobacillus flagellatum and *Corynebacterium glutamicum*, Serebriiskii, I.G. et al, Nov. 21, 1996.

GenBank Accession No. U35023 for A *Corynebacterium glutamicum* gene encoding a two-domain protein similar to biotin carboxylases and biotin-carboxyl-carrier proteins, Jager, W. et al, Jan. 16, 1997.

GenBank Accession No. U43535 for A *Corynebacterium glutamicum* gene conferring multidrug resistance in the heterologous host *Escherichia coli*, Jager, W. et al, Apr. 9, 1997.

GenBank Accession No. U43536 for *Corynebacterium glutamicum*, Jaeger, W. et al, Mar. 13, 1997.

GenBank Accession No. U53587 for Utilization of IS1207 for insertional mutagenesis in Corynebacteria, Bonamy, C. et al, May 6, 1996.

GenBank Accession No. U89648 for *Corynebacterium glutamicum*, Kim, S.Y. et al, Mar. 30, 1999.

GenBank Accession No. X04960 for complete nucleotide and deduced amino acid sequences of the *Brevibacterium lactofermentum* tryptophan operon, Matsui, K. et al, Apr. 18, 2005.

GenBank Accession No. X07563 for Nucleotide sequence of the lysA gene of *Corynebacterium glutamicum* and possible mechanisms for modulation of its expression, Yeh, P. et al, Apr. 18, 2005.
GenBank Accession No. X14234 for The phosphoenolpyruvate carboxylase gene of *Corynebacterium glutamicum*: molecular cloning, nucleotide sequence, and expression, Eikmanns, B.J. et al, Apr. 18, 2005.
GenBank Accession No. X17313 for Molecular cloning, nucleotide sequence and fine-structural analysis of teh *Corynebacterium glutamicum* fda gene: structural comparison of *C. glutamicum* fructose-1, 6-biphosphate aldolase to class I and Class II aldolases, von der Osten, C.H. et al, Apr. 18, 2005.
GenBank Accession No. X53993 for Nucleotide sequence of the dapA gene from *Corynebacterium glutamicum*, Bonnassie, S. et al, Apr. 18, 2005.
GenBank Accession No. X54223 for DNA sequence homology between att B-related sites of *Corynebacterium diphtheriae*, *Corynebacterium ulcerans*, *Corynebacterium glutamicum*, and the attP site of lambda-corynephage, Cianciotto, N. et al, Dec. 17, 1992.
GenBank Accession No. X54740 for Nucleotide sequence and organization of the upstream region of the *Corynebacterium glutamicum* lysA gene, Marcel, T. et al, Apr. 18, 2005.
GenBank Accession No. X55994 for Nucleotide sequence of the *Corynebacterium glutamicum* trpE gene, Heery, D.M. et al, Apr. 18, 2005.
GenBank Accession No. X56037 for The molecular structure of the *Corynebacterium glutamicum* threonine synthase gene, Han, K.S. et al, Apr. 18, 2005.
GenBank Accession No. X56075 for DNA sequence homology between att B-related sites of *Corynebacterium diphtheriae*, *Corynebacterium ulcerans*, *Corynebacterium glutamicum*, adn the attP site of Lambda-corynephage, Cianciotto, N. et al, Dec. 17, 1992.
GenBank Accession No. X57226 for Aspartokinase genes lysC alpha and lysC beta overlap and are adjacent to the aspartate beta-semialdehyde dehydrogenase gene asd *Corynebacterium glutamicum*, Kalinowski, J. et al, Apr. 18, 2005.
GenBank Accession No. X59403 for Identification, sequence analysis, and expression of a *Corynebacterium glutamicum* gene cluster encoding the three glycolytic enzymes glyceraldehyde-3-phosphate dehydrogenase, 3-phosphoglycerate kinase, and triosephosphate isomerase, Eikmanns, B.J. et al, Apr. 18, 2005.
GenBank Accession No. X59404, Bormann, E.R. et al, "Molecular analysis of the *Corynebacterium glutamicum* gbh gene encoding glutamate dehydrogenase," *Mol. Microbiol.*, vol. 6(3):317-326 (1992), Apr. 18, 2005.
GenBank Accession No. X60312 for Molecular analysis of the *Corynebacterium glutamicum* lysl gene involved in lysine uptake, Seep-Feldhaus, A.H. et al, Jan. 30, 1992.
GenBank Accession No. X66078 for Cloning and nucleotide sequence of the csp1 gene encoding PS1, one of the two major secreted proteins of *Corynebacterium glutamicum*: the deduced N-terminal region of PS1 is similar to the *Mycobacterium* antigen 85 complex, Joliff, G. et al, Jun. 30, 1993.
GenBank Accession No. X66112, Eikmanns, B.J. et al, "Nucleotide sequence, expression and transcriptional analysis of the *Corynebacterium glutamicum* gltA gene encoding citrate synthase," *Microbiology*, vol. 140(pt. 8):1817-1828 (1994), Apr. 18, 2005.
GenBank Accession No. X67737 for *Corynebacterium glutamicum*, Eikmanns, B.J. et al, Apr. 18, 2005.
GenBank Accession No. X69103 for Characterization of the cspB gene encoding PS2, an ordered surface-layer protein in *Corynebacterium glutamicum*, Peyret, J.L. et al, Sep. 9, 2004.
GenBank Accession No. X69104 for Identification of IS1206, a *Corynebacterium glutamicum* IS3-related insertion sequence and phylogenetic analysis, Bonamy, C. et al, Sep. 9, 2004.
GenBank Accession No. X70584 for In vivo comparison of zidovudine resistance mutations in blood and CSF of HIV-1-infected patients, Wildermann, B. et al, Aug. 6, 1995.
GenBank Accession No. X70959 for Leucine synthesis in *Corynebacterium glutamicum*: enzyme activities, structure of leuA, and effect of leuA inactivation on lysine synthesis, Patek, M. et al, Sep. 9, 2004.

GenBank Accession No. X71489 for Cloning, sequence analysis, expression, and inactivation of the *Corynebacterium glutamicum* icd gene encoding isocitrate dehydrogenase and biochemical characterization of the enzyme, Eikmanns, B.J. et al, Apr. 18, 2005.
GenBank Accession No. X72855, Guyonvarch, A. et al, "Glutamate dehydrogenase (gdhA) gene." Apr. 18, 2005.
GenBank Accession No. X75083 for A sequence from a tryptophan-hyperproducing strain of *Corynebacterium glutamicum* encoding resistance to 5-methyltryptophan, Heery, D. M. et al, Aug. 18, 1994.
GenBank Accession No. X75085 for Construction and characterization of recA mutant strains of *Corynebacterium glutamicum* and *Brevibacterium lactofermentum*, Fitzpatrick, R. et al, Apr. 18, 2005.
GenBank Accession No. X75504 for characterization of the isocitrate lyase gene from *Corynebacterium glutamicum* and biochemical analysis of the enzyme, Reinscheid, D.J. et al, Apr. 18, 2005.
GenBank Accession No. X76875 for Phylogenetic relationships of Bacteria based on comparative sequence analysis of elongation factor Tu and ATP-synthase beta-subunit genes, Ludwig, W. et al, Oct. 27, 1994.
GenBank Accession No. X77034 for Phylogenetic relationships of Bacteria based on comparative sequence analysis of elongation factor Tu and ATP-synthase beta-subunit genes, Ludwig, W. et al, Apr. 18, 2005.
GenBank Accession No. X77384 for Nucleotide sequence of a recA gene from *Corynebacterium glutamicum*, Billman-Jacobe, H. et al, Apr. 18, 2005.
GenBank Accession No. X78491 for Malate synthase from *Corynebacterium glutamicum*: sequence analysis of the gene and biochemical characterization of the enzyme, Reinscheid, D.J. et al, Apr. 18, 2005.
GenBank Accession No. X80629 for Phytogenetic analysis of the genera *Rhodococcus* and *Norcardia* and evidence for the evolutionary origin of the genus *Nocardia* from within the radiation of *Rhodococcus* species, Rainey, F.A. et al, Apr. 1, 2004.
GenBank Accession No. X81191 for Structure of the gluABCD cluster encoding the glutamate uptake system of *Corynebacterium glutamicum*, Kronemeyer, W. et al, Apr. 18, 2005.
GenBank Accession No. X81379, Wehrmann, A. et al, "Analysis of different DNA fragments of *Corynebacterium glutamicum* complementing dapE of *Escherichia coli*," *Microbiology*, vol. 140(pt. 12):3349-3356 (1994), Feb. 25, 2003.
GenBank Accession No. X82061 for Phylogeny of the genus *Corynebacterium* deduced from analysis of small-subunit ribosomal DNA sequences, Ruimy, R. et al, Nov. 10, 1995.
GenBank Accession No. X82928 for Multicopy suppression by asd gene and osmotic stress-dependent complementation by heterologous proA in proA mutants, Serebrijski, I. et al, Apr. 18, 2005.
GenBank Accession No. X82929 for Multicopy suppression by asd gene and osmotic stress-dependent complementation by heterologous proA in proA mutants, Serebrijski, I. et al, Apr. 18, 2005.
GenBank Accession No. X84257 for Phylogenetic analysis of the genus *Corynebacterium* based on 16S rRNA gene sequences, Pascual, C. et al, Jan. 9, 2004.
GenBank Accession No. X85965, Wehrmann, A. et al, "Functional analysis of sequences adjacent to dapE of *Corynebacterium glutamicum* reveals the presence of aroP, which encodes the aromatic amino acid transporter," *J. Bacteriol.*, vol. 177(20):5991-5993 (1995), Nov. 30, 1997.
GenBank Accession No. X86157, Sakanyan, V. et al, "Genes and enzymes of the acetyl cycle of arginine biosynthesis in *Corynebacterium glutamicum*: enzyme evolution in the early steps of the arginine pathway," *Microbiology*, vol. 142(Pt. 1):99-108 (1996), Apr. 18, 2005.
GenBank Accession No. X86780 for The biosynthetic gene cluster for the polyketide immunosuppresant rapamycin, Schwecke, T. et al, Apr. 18, 2005.
GenBank Accession No. X89084 for Cloning, sequence analysis, expression and inactivation of the *Corynebacterium glutamicum* pta-ack operon encoding phosphotransacetylase and acetate kinase, Reinscheid, D.J. et al, Apr. 18, 2005.

GenBank Accession No. X89850 for Genetic characterization of site-specific integration functions of phi AAU2 infecting 'Arthrobacter aureus' C70, Le Marrec, C. et al, Aug. 8, 1996.
GenBank Accession No. X90356 for Promoters from *Corynebacterium glutamicum*: cloning, molecular analysis and search for a consensus motif, Patek, M. et al, Nov. 4, 1996.
GenBank Accession No. X90357 for Promoters from *Corynebacterium glutamicum*: cloning, molecular analysis and search for a consensus motif, Patek, M. et al, Nov. 4, 1996.
GenBank Accession No. X90358 for Promoters from *Corynebacterium glutamicum*: cloning, molecular analysis and search for a consensus motif, Patek, M. et al, Nov. 4, 1996.
GenBank Accession No. X90359 for Promoters from *Corynebacterium glutamicum*: cloning, molecular analysis and search for a consensus motif, Patek, M. et al, Nov. 4, 1996.
GenBank Accession No. X90360 for Promoters from *Corynebacterium glutamicum*: cloning, molecular analysis and search for a consensus motif, Patek, M. et al, Nov. 4, 1996.
GenBank Accession No. X90361 for Promoters from *Corynebacterium glutamicum*: cloning, molecular analysis and search for a consensus motif, Patek, M. et al, Nov. 4, 1996.
GenBank Accession No. X90362 for Promoters from *Corynebacterium glutamicum*: cloning, molecular analysis and search for a consensus motif, Patek, M. et al, Nov. 4, 1996.
GenBank Accession No. X90363 for Promoters from *Corynebacterium glutamicum*: cloning, molecular analysis and search for a consensus motif, Patek, M. et al, Nov. 4, 1996.
GenBank Accession No. X90364 for Promoters from *Corynebacterium glutamicum*: cloning, molecular analysis and search for a consensus motif, Patek, M. et al, Nov. 4, 1996.
GenBank Accession No. X90365 for Promoters from *Corynebacterium glutamicum*: cloning, molecular analysis and search for a consensus motif, Patek, M. et al, Nov. 4, 1996.
GenBank Accession No. X90366 for Promoters from *Corynebacterium glutamicum*: cloning, molecular analysis and search for a consensus motif, Patek, M. et al, Nov. 4, 1996.
GenBank Accession No. X90367 for Promoters from *Corynebacterium glutamicum*: cloning, molecular analysis and search for a consensus motif, Patek, M. et al, Nov. 4, 1996.
GenBank Accession No. X90368 for Promoters from *Corynebacterium glutamicum*: cloning, molecular analysis and search for a consensus motif, Patek, M. et al, Nov. 4, 1996.
GenBank Accession No. X93513, Siewe, R.M. et al, "Functional and genetic characterization of the (methyl)ammonium uptake carrier of *Corynebacterium glutamicum*," *J. Biol. Chem.*, vol. 271(10):5398-5403 (1996), May 29, 1996.
GenBank Accession No. X93514 for Isolation, characterization, and expression of the *Corynebacterium glutamicum* betP gene, encoding the transport system for the compatible solute glycine betaine, Peter, H. et al, Sep. 8, 1997.
GenBank Accession No. X95649 for Identification and transcriptional analysis of the dapB-ORF2-dapA-ORF4 operon of *Corynebacterium glutamicum*, encoding two enzymes involved in L-lysine synthesis, Patek, M. et al, Dec. 21, 2000.
GenBank Accession No. X96471 for A new type of transporter with a new type of cellular function: L-lysine export from *Corynebacterium glutamicum*, Vrljic, M. et al, Apr. 18, 2005.
GenBank Accession No. X96580, Sahm, H. et al, "D-Pantothenate synthesis in *Corynebacterium glutamicum* and use of panBC and genes encoding L-valine synthesis for D-pantothenate overproduction," *Appl. Environ. Microbiol.*, vol. 65(5):1973-1979 (1999), Apr. 18, 2005.
GenBank Accession No. X96962 for Utilisation of IS1207 for insertional mutagenesis in *Corynbacteria*, Bonamy, C. et al, Jul. 7, 2002.
GenBank Accession No. X99289 for Cloning, sequencing and expression of the gene encoding elongation factor P in the amino-acid producer *Brevibacterium lactofermentum* (*Corynebacterium glutamicum* ATCC 13869), Ramos, A. et al, Sep. 9, 2004.
GenBank Accession No. Y00140 for Nucleotide sequence of the homoserine kinase (thr B) gene of *Brevibacterium lactofermentum*, Mateos, L.M. et al, Sep. 12, 1993.

GenBank Accession No. Y00151 for Nucleotide sequence of the meso-diaminopimelate D-dehydrogenase gene from *Corynebacterium glutamicum*, Ishino, S. et al, Sep. 12, 1993.
GenBank Accession No. Y00476 for Nucleotide sequence of the homoserine dehydrogenase (thr A) gene of *Brevibacterium lactofermentum*, Mateos, L.M. et al, May 5, 1993.
GenBank Accession No. Y00546 for Nucleotide sequence and fine structural analysis of the *Corynebacterium glutamicum* hom-thrB operon, Peoples, O.P. et al, Sep. 12, 1993.
GenBank Accession No. Y08964 for Identification, characterization, and chromosomal organization of the ftsZ gene from *Brevibacterium lactofermentum*, Honrubia, M.P. et al, Apr. 18, 2005.
GenBank Accession No. Y09163 for Isolation of the putP gene of *Corynebacterium glutamicum* and characterization of a low-affinity uptake system for compatible solutes, Peter, H. et al, Sep. 8, 1997.
GenBank Accession No. Y09548 for Pyruvate carboxylase from *Corynebacterium glutamicum*: characterization, expression and inactivation of the pyc gene, Peters-Wendisch, P.G. et al, Apr. 18, 2005.
GenBank Accession No. Y09578 for Analysis of the leuB gene from *Corynebacterium glutamicum*, Patek, M. et al, Apr. 18, 2005.
GenBank Accession No. Y12472 for Site-specific integration of corynephage phi16: the construction of an integration vector, Moreau, S. et al, Mar. 5, 1999.
GenBank Accession No. Y12537 for *Corynebacterium glutamicum* is equipped with four secondary carriers for compatible solutes: identification, sequencing, and characterization of the proline/glycine betaine carrier, EctP, Peter, H. et al, Nov. 17, 1998.
GenBank Accession No. Y13221 for Isolation of the *Corynebacterium glutamicum* glnA gene encoding glutamine synthetase I, Jakoby, M. et al, Aug. 28, 1997.
GenBank Accession No. Y13627 for Identification of novel intergenic repetitive units in a mycobacterial two-component system operon, Supply, P. et al, Apr. 18, 2005.
GenBank Accession No. Y16642 for *Corynebacterium glutamicum*, Schwinde, J. et al, Apr. 18, 2005.
GenBank Accession No. Y18059 for Analysis of the integration functions of phi304L: an integrase module among corynephages, Moreau, S. et al, Sep. 29, 1999.
GenBank Accession No. Z21501 for A gene encoding arginyl-tRNA synthetase is located in the upstream region of the lysA gene in *Brevibacterium lactofermentum*: regulation of argS-lysA cluster expression by arginine, Oguiza, J.A. et al, Apr. 18, 2005.
GenBank Accession No. Z21502 for A cluster of three genes (dapA, orf2, and dapB) *Brevibacterium lactofermentum* encodes dihydrodipicolinate synthase, dihydrodipicolinate reductase, and a third polypeptide of unknown function, Pisabarro, A. et al, Aug. 16, 1993.
GenBank Accession No. Z29563 for Analysis and expression of the thrC gene of *Brevibacterium lactofermentum* and characterization of the encoded threonine synthase, Malumbres, M. et al, Apr. 18, 2005.
GenBank Accession No. Z46753 for Phylogeny of *Corynebacterium glutamicum*, Chun, J. et al, Nov. 21, 1994.
GenBank Accession No. Z49822 for Multiple sigma factor genes in *Brevibacterium lactofermentum*: characterization of sigA and sigB, Oguiza, J.A. et al, Apr. 18, 2005.
GenBank Accession No. Z49823 for The galE gene encoding the UDP-galactose 4-epimerase of *Brevibacterium lactofermentum* is coupled transcriptionally to the dmdR gene, Oguiza, J.A. et al, Apr. 18, 2005.
GenBank Accession No. Z49824 for Multiple sigma factor genes in *Brevibacterium lactofermentum*: characterization of sigA and sigB, Oguiza, J.A. et al, Apr. 18, 2005.
GenBank Accession No. Z66534 for Cloning and characterization of an IS-like element present in the genome of *Brevibacterium lactofermentum* ATCC 13869, Correia, A. et al, Jul. 7, 2002.
GenBank Accession No. Z77162 for Deciphering the biology of Mycobacterium tuberculosis from the complete genome sequence, Cole, S.T. et al, Sep. 2, 2002.

GenBank Accession No. Z80226 for Deciphering the biology of Mycobacterium tuberculosis from the complete genome sequence, Cole, S.T. et al, Sep. 2, 2002.

GenBank Accession No. Z81368, Cole, S.T. et al, "Deciphering the biology of Mycobacterium tuberculosis from the complete genome sequence," *Nature*, vol. 393(6685):537-544 (1998), Sep. 2, 2002.

GenBank Accession No. Z98209, Cole, S.T. et al, "Deciphering the biology of Mycobacterium tuberculosis from the complete genome sequence," *Nature*, vol. 393(6685):537-544 (1998), Aug. 3, 2001.

GenBank Accession No. Z83866 for Deciphering the biology of Mycobacterium tuberculosis from the complete genome sequence, Cole, S.T. et al, Sep. 2, 2002.

GenBank Accession No. Z95388, Cole, S.T. et al, "Deciphering the biology of Mycobacterium tuberculosis from the complete genome sequence," *Nature*, vol. 396(6685):537-544 (1998) Feb. 10, 1999.

Eggleling, L. et al, "Transport Mutants and Transport Genes of *Corynebacterium glutamicum*," *Annals of the New York Academy of Sciences*, vol. 782:191-201 (1996).

GenBank Accession No. A89996, Kuroda et al, "Probable Ammonium Transporter nrgA, Protein Information Resource Database," May 2001.

Lee, J.K. et al. "Nucleotide sequence of the gene encoding the *Corynebacterium glutamicum* mannose enzyme II and analyses of the deduced protein sequence," *FEMS Microbiol. Lett.*, 119(1-2):137-145 (1994).

Schäfer, A. et al. "The *Corynebacterium glutamicum* cgllM gene encoding a 5-cytosine in an McrBC-deficient *Escherichia coli* strain," *Gene*, 203(2):95-101 (1997).

US 7,273,721 B2

CORYNEBACTERIUM GLUTAMICUM GENES ENCODING PROTEINS INVOLVED IN MEMBRANE SYNTHESIS AND MEMBRANE TRANSPORT

RELATED APPLICATIONS

This application is a continuation application of U.S. application Ser. No. 09/602,787 filed Jun. 23, 2000 now U.S. Pat. No. 6,696,561 which claims priority to prior filed U.S. Provisional Patent Application Ser. No. 60/141,031, filed Jun. 25, 1999. This application also claims priority to German Patent Application No. 19931454.3, filed Jul. 8, 1999, German Patent Application No. 19931478.0, filed Jul. 8, 1999, German Patent Application No. 19931563.9, filed Jul. 8, 1999, German Patent Application No. 19932122.1, filed Jul. 9, 1999, German Patent Application No. 19932124.8, filed Jul. 9, 1999, German Patent Application No. 19932125.6, filed Jul. 9, 1999, German Patent Application No. 19932128.0, filed Jul. 9, 1999, German Patent Application No. 19932180.9, filed Jul. 9, 1999, German Patent Application No. 19932182.5, filed Jul. 9, 1999, German Patent Application No. 19932190.6, filed Jul. 9, 1999, German Patent Application No. 19932191.4, filed Jul. 9, 1999, German Patent Application No. 19932209.0, filed Jul. 9, 1999, German Patent Application No. 19932212.0, filed Jul. 9, 1999, German Patent Application No. 19932227.9, filed Jul. 9, 1999, German Patent Application No. 19932228.7, filed Jul. 9, 1999, German Patent Application No. 19932229.5, filed Jul. 9, 1999, German Patent Application No. 19932230.9, filed Jul. 9, 1999, German Patent Application No. 19932927.3, filed Jul. 14, 1999, German Patent Application No. 19933005.0, filed Jul. 14, 1999, German Patent Application No. 19933006.9, filed Jul. 14, 1999, German Patent Application No. 19940764.9, filed Aug. 27, 1999, German Patent Application No. 19940765.7, filed Aug. 27, 1999, German Patent Application No. 19940766.5, filed Aug. 27, 1999, German Patent Application No. 19940830.0, filed Aug. 27, 1999, German Patent Application No. 19940831.9, filed Aug. 27, 1999, German Patent Application No. 19940832.7, filed Aug. 27, 1999, German Patent Application No. 19940833.5, filed Aug. 27, 1999, German Patent Application No. 19941378.9 filed Aug. 31, 1999, German Patent Application No. 19941379.7, filed Aug. 31, 1999, German Patent Application No. 19941395.9, filed Aug. 31, 1999, German Patent Application No. 19942077.7, filed Sep. 3, 1999, German Patent Application No. 19942078.5, filed Sep. 3, 1999, German Patent Application No. 19942079.3, filed Sep. 3, 1999, and German Patent Application No. 19942088.2, filed Sep. 3, 1999. The entire contents of all of the above referenced applications are hereby expressly incorporated herein by this reference.

INCORPORATION OF MATERIAL SUBMITTED ON COMPACT DISCS

This application incorporates herein by reference the material contained on the compact discs submitted herewith as part of this application. Specifically, the file "seqlist" (2.43 MB) contained on each of Copy 1, Copy 2 and the CRF copy of the Sequence Listing is hereby incorporated herein by reference. This file was created on Jul. 25, 2003.

BACKGROUND OF THE INVENTION

Certain products and by-products of naturally-occurring metabolic processes in cells have utility in a wide array of industries, including the food, feed, cosmetics, and pharmaceutical industries. These molecules, collectively termed 'fine chemicals', include organic acids, both proteinogenic and non-proteinogenic amino acids, nucleotides and nucleosides, lipids and fatty acids, diols, carbohydrates, aromatic compounds, vitamins and cofactors, and enzymes. Their production is most conveniently performed through the large-scale culture of bacteria developed to produce and secrete large quantities of one or more desired molecules. One particularly useful organism for this purpose is *Corynebacterium glutamicum*, a gram positive, nonpathogenic bacterium. Through strain selection, a number of mutant strains have been developed which produce an array of desirable compounds. However, selection of strains improved for the production of a particular molecule is a time-consuming and difficult process.

SUMMARY OF THE INVENTION

The invention provides novel bacterial nucleic acid molecules which have a variety of uses. These uses include the identification of microorganisms which can be used to produce fine chemicals, the modulation of fine chemical production in *C. glutamicum* or related bacteria, the typing or identification of *C. glutamicum* or related bacteria, as reference points for mapping the *C. glutamicum* genome, and as markers for transformation. These novel nucleic acid molecules encode proteins, referred to herein as membrane construction and membrane transport (MCT) proteins.

*C. glutamicum* is a gram positive, aerobic bacterium which is commonly used in industry for the large-scale production of a variety of fine chemicals, and also for the degradation of hydrocarbons (such as in petroleum spills) and for the oxidation of terpenoids. The MCT nucleic acid molecules of the invention, therefore, can be used to identify microorganisms which can be used to produce fine chemicals, e.g., by fermentation processes. Modulation of the expression of the MCT nucleic acids of the invention, or modification of the sequence of the MCT nucleic acid molecules of the invention, can be used to modulate the production of one or more fine chemicals from a microorganism (e.g., to improve the yield or production of one or more fine chemicals from a *Corynebacterium* or *Brevibacterium* species).

The MCT nucleic acids of the invention may also be used to identify an organism as being *Corynebacterium glutamicum* or a close relative thereof, or to identify the presence of *C. glutamicum* or a relative thereof in a mixed population of microorganisms. The invention provides the nucleic acid sequences of a number of *C. glutamicum* genes; by probing the extracted genomic DNA of a culture of a unique or mixed population of microorganisms under stringent conditions with a probe spanning a region of a *C. glutamicum* gene which is unique to this organism, one can ascertain whether this organism is present. Although *Corynebacterium glutamicum* itself is nonpathogenic, it is related to species pathogenic in humans, such as *Corynebacterium diphtheriae* (the causative agent of diphtheria); the detection of such organisms is of significant clinical relevance.

The MCT nucleic acid molecules of the invention may also serve as reference points for mapping of the *C. glutamicum* genome, or of genomes of related organisms. Similarly, these molecules, or variants or portions thereof, may serve as markers for genetically engineered *Corynebacterium* or *Brevibacterium* species. e.g.e.g. The MCT proteins encoded by the novel nucleic acid molecules of the invention are capable of, for example, performing a function involved in the metabolism (e.g., the biosynthesis or degradation) of compounds necessary for membrane biosynthesis, or of assisting in the transmembrane transport of one or more compounds either into or out of the cell. Given the availability of cloning vectors for use in *Corynebacterium glutamicum*, such as those disclosed in Sinskey et al., U.S. Pat. No. 4,649,119, and techniques for genetic manipulation of *C. glutamicum* and the related *Brevibacterium* species (e.g., *lactofermentum*) (Yoshihama et al, *J. Bacteriol.* 162: 591-597 (1985); Katsumata et al., *J. Bacteriol.* 159: 306-311 (1984); and Santamaria et al., *J. Gen. Microbiol.* 130: 2237-2246 (1984)), the nucleic acid molecules of the invention may be utilized in the genetic engineering of this organism to make it a better or more efficient producer of one or more fine chemicals. This improved production or efficiency of production of a fine chemical may be due to a direct effect of manipulation of a gene of the invention, or it may be due to an indirect effect of such manipulation.

There are a number of mechanisms by which the alteration of an MCT protein of the invention may directly affect the yield, production, and/or efficiency of production of a fine chemical from a *C. glutamicum* strain incorporating such an altered protein. Those MCT proteins involved in the export of fine chemical molecules from the cell may be increased in number or activity such that greater quantities of these compounds are secreted to the extracellular medium, from which they are more readily recovered. Similarly, those MCT proteins involved in the import of nutrients necessary for the biosynthesis of one or more fine chemicals (e.g., phosphate, sulfate, nitrogen compounds, etc.) may be increased in number or activity such that these precursors, cofactors, or intermediate compounds are increased in concentration within the cell. Further, fatty acids and lipids themselves are desirable fine chemicals; by optimizing the activity or increasing the number of one or more MCT proteins of the invention which participate in the biosynthesis of these compounds, or by impairing the activity of one or more MCT proteins which are involved in the degradation of these compounds, it may be possible to increase the yield, production, and/or efficiency of production of fatty acid and lipid molecules from *C. glutamicum*.

The mutagenesis of one or more MCT genes of the invention may also result in MCT proteins having altered activities which indirectly impact the production of one or more desired fine chemicals from *C. glutamicum*. For example, MCT proteins of the invention involved in the export of waste products may be increased in number or activity such that the normal metabolic wastes of the cell (possibly increased in quantity due to the overproduction of the desired fine chemical) are efficiently exported before they are able to damage nucleotides and proteins within the cell (which would decrease the viability of the cell) or to interfere with fine chemical biosynthetic pathways (which would decrease the yield, production, or efficiency of production of the desired fine chemical). Further, the relatively large intracellular quantities of the desired fine chemical may in itself be toxic to the cell, so by increasing the activity or number of transporters able to export this compound from the cell, one may increase the viability of the cell in culture, in turn leading to a greater number of cells in the culture producing the desired fine chemical. The MCT proteins of the invention may also be manipulated such that the relative amounts of different lipid and fatty acid molecules are produced. This may have a profound effect on the lipid composition of the membrane of the cell. Since each type of lipid has different physical properties, an alteration in the lipid composition of a membrane may significantly alter membrane fluidity. Changes in membrane fluidity can impact the transport of molecules across the membrane, as well as the integrity of the cell, both of which have a profound effect on the production of fine chemicals from *C. glutamicum* in large-scale fermentative culture.

The invention provides novel nucleic acid molecules which encode proteins, referred to herein as MCT proteins, which are capable of, for example, participating in the metabolism of compounds necessary for the construction of cellular membranes in *C. glutamicum*, or in the transport of molecules across these membranes. Nucleic acid molecules encoding an MCT protein are referred to herein as MCT nucleic acid molecules. In a preferred embodiment, the MCT protein participates in the metabolism of compounds necessary for the construction of cellular membranes in *C. glutamicum*, or in the transport of molecules across these membranes. Examples of such proteins include those encoded by the genes set forth in Table 1.

Accordingly, one aspect of the invention pertains to isolated nucleic acid molecules (e.g., cDNAs, DNAs, or RNAs) comprising a nucleotide sequence encoding an MCT protein or biologically active portions thereof, as well as nucleic acid fragments suitable as primers or hybridization probes for the detection or amplification of MCT-encoding nucleic acid (e.g., DNA or mRNA). In particularly preferred embodiments, the isolated nucleic acid molecule comprises one of the nucleotide sequences set forth in Appendix A or the coding region or a complement thereof of one of these nucleotide sequences. In other particularly preferred embodiments, the isolated nucleic acid molecule of the invention comprises a nucleotide sequence which hybridizes to or is at least about 50%, preferably at least about 60%, more preferably at least about 70%, 80% or 90%, and even more preferably at least about 95%, 96%, 97%, 98%, 99% or more homologous to a nucleotide sequence set forth in Appendix A, or a portion thereof. In other preferred embodiments, the isolated nucleic acid molecule encodes one of the amino acid sequences set forth in Appendix B. The preferred MCT proteins of the present invention also preferably possess at least one of the MCT activities described herein.

In another embodiment, the isolated nucleic acid molecule encodes a protein or portion thereof wherein the protein or portion thereof includes an amino acid sequence which is sufficiently homologous to an amino acid sequence of Appendix B, e.g., sufficiently homologous to an amino acid sequence of Appendix B such that the protein or portion thereof maintains an MCT activity. Preferably, the protein or portion thereof encoded by the nucleic acid molecule maintains the ability to participate in the metabolism of compounds necessary for the construction of cellular membranes in *C. glutamicum*, or in the transport of molecules across these membranes. In one embodiment, the protein encoded by the nucleic acid molecule is at least about 50%, preferably at least about 60%, and more preferably at least about 70%, 80%, or 90% and most preferably at least about 95%, 96%, 97%, 98%, or 99% or more homologous to an amino acid sequence of Appendix B (e.g., an entire amino acid sequence selected from those sequences set forth in Appendix B). In another preferred embodiment, the protein is a full length *C. glutamicum* protein which is substantially homologous to an entire amino acid sequence of Appendix B (encoded by an open reading frame shown in Appendix A).

In another preferred embodiment, the isolated nucleic acid molecule is derived from *C. glutamicum* and encodes a protein (e.g., an MCT fusion protein) which includes a biologically active domain which is at least about 50% or more homologous to one of the amino acid sequences of Appendix B and is able to participate in the metabolism of compounds necessary for the construction of cellular membranes in *C. glutamicum*, or in the transport of molecules across these membranes, or has one or more of the activities set forth in Table 1, and which also includes heterologous nucleic acid sequences encoding a heterologous polypeptide or regulatory regions.

In another embodiment, the isolated nucleic acid molecule is at least 15 nucleotides in length and hybridizes under stringent conditions to a nucleic acid molecule comprising a nucleotide sequence of Appendix A. Preferably, the isolated nucleic acid molecule corresponds to a naturally-occurring nucleic acid molecule. More preferably, the isolated nucleic acid encodes a naturally-occurring *C. glutamicum* MCT protein, or a biologically active portion thereof.

Another aspect of the invention pertains to vectors, e.g., recombinant expression vectors, containing the nucleic acid molecules of the invention, and host cells into which such vectors have been introduced. In one embodiment, such a host cell is used to produce an MCT protein by culturing the host cell in a suitable medium. The MCT protein can be then isolated from the medium or the host cell.

Yet another aspect of the invention pertains to a genetically altered microorganism in which an MCT gene has been introduced or altered. In one embodiment, the genome of the microorganism has been altered by introduction of a nucleic acid molecule of the invention encoding wild-type or mutated MCT sequence as a transgene. In another embodiment, an endogenous MCT gene within the genome of the microorganism has been altered, e.g., functionally disrupted, by homologous recombination with an altered MCT gene. In another embodiment, an endogenous or introduced MCT gene in a microorganism has been altered by one or more point mutations, deletions, or inversions, but still encodes a functional MCT protein. In still another embodiment, one or more of the regulatory regions (e.g., a promoter, repressor, or inducer) of an MCT gene in a microorganism has been altered (e.g., by deletion, truncation, inversion, or point mutation) such that the expression of the MCT gene is modulated. In a preferred embodiment, the microorganism belongs to the genus *Corynebacterium* or *Brevibacterium*, with *Corynebacterium glutamicum* being particularly preferred. In a preferred embodiment, the microorganism is also utilized for the production of a desired compound, such as an amino acid, with lysine being particularly preferred.

In another aspect, the invention provides a method of identifying the presence or activity of *Coryneobacterium diphtheriae* in a subject. This method includes detection of one or more of the nucleic acid or amino acid sequences of the invention (e.g., the sequences set forth in Appendix A or Appendix B) in a subject, thereby detecting the presence or activity of *Corynebacterium diphtheriae* in the subject.

Still another aspect of the invention pertains to an isolated MCT protein or a portion, e.g., a biologically active portion, thereof. In a preferred embodiment, the isolated MCT protein or portion thereof can participate in the metabolism of compounds necessary for the construction of cellular membranes in *C. glutamicum*, or in the transport of molecules across these membranes. In another preferred embodiment, the isolated MCT protein or portion thereof is sufficiently homologous to an amino acid sequence of Appendix B such that the protein or portion thereof maintains the ability to participate in the metabolism of compounds necessary for the construction of cellular membranes in *C. glutamicum*, or in the transport of molecules across these membranes.

The invention also provides an isolated preparation of an MCT protein. In preferred embodiments, the MCT protein comprises an amino acid sequence of Appendix B. In another preferred embodiment, the invention pertains to an isolated full length protein which is substantially homologous to an entire amino acid sequence of Appendix B (encoded by an open reading frame set forth in Appendix A). In yet another embodiment, the protein is at least about 50%, preferably at least about 60%, and more preferably at least about 70%, 80%, or 90%, and most preferably at least about 95%, 96%, 97%, 98%, or 99% or more homologous to an entire amino acid sequence of Appendix B. In other embodiments, the isolated MCT protein comprises an amino acid sequence which is at least about 50% or more homologous to one of the amino acid sequences of Appendix B and is able to participate in the metabolism of compounds necessary for the construction of cellular membranes in *C. glutamicum*, or in the transport of molecules across these membranes, or has one or more of the activities set forth in Table 1.

Alternatively, the isolated MCT protein can comprise an amino acid sequence which is encoded by a nucleotide sequence which hybridizes, e.g., hybridizes under stringent conditions, or is at least about 50%, preferably at least about 60%, more preferably at least about 70%, 80%, or 90%, and even more preferably at least about 95%, 96%, 97%, 98%, or 99% or more homologous, to a nucleotide sequence of Appendix B. It is also preferred that the preferred forms of MCT proteins also have one or more of the MCT bioactivities described herein.

The MCT polypeptide, or a biologically active portion thereof, can be operatively linked to a non-MCT polypeptide to form a fusion protein. In preferred embodiments, this fusion protein has an activity which differs from that of the MCT protein alone. In other preferred embodiments, this fusion protein participate in the metabolism of compounds necessary for the construction of cellular membranes in *C. glutamicum*, or in the transport of molecules across these membranes. In particularly preferred embodiments, integration of this fusion protein into a host cell modulates production of a desired compound from the cell.

In another aspect, the invention provides methods for screening molecules which modulate the activity of an MCT protein, either by interacting with the protein itself or a substrate or binding partner of the MCT protein, or by modulating the transcription or translation of an MCT nucleic acid molecule of the invention.

Another aspect of the invention pertains to a method for producing a fine chemical. This method involves the culturing of a cell containing a vector directing the expression of an MCT nucleic acid molecule of the invention, such that a fine chemical is produced. In a preferred embodiment, this method further includes the step of obtaining a cell containing such a vector, in which a cell is transfected with a vector directing the expression of an MCT nucleic acid. In another preferred embodiment, this method further includes the step of recovering the fine chemical from the culture. In a particularly preferred embodiment, the cell is from the genus *Corynebacterium* or *Brevibacterium*, or is selected from those strains set forth in Table 3.

Another aspect of the invention pertains to methods for modulating production of a molecule from a microorganism. Such methods include contacting the cell with an agent which modulates MCT protein activity or MCT nucleic acid expression such that a cell associated activity is altered relative to this same activity in the absence of the agent. In a preferred embodiment, the cell is modulated for one or more C. glutamicum metabolic pathways for cell membrane components or is modulated for the transport of compounds across such membranes, such that the yields or rate of production of a desired fine chemical by this microorganism is improved. The agent which modulates MCT protein activity can be an agent which stimulates MCT protein activity or MCT nucleic acid expression. Examples of agents which stimulate MCT protein activity or MCT nucleic acid expression include small molecules, active MCT proteins, and nucleic acids encoding MCT proteins that have been introduced into the cell. Examples of agents which inhibit MCT activity or expression include small molecules and antisense MCT nucleic acid molecules.

Another aspect of the invention pertains to methods for modulating yields of a desired compound from a cell, involving the introduction of a wild-type or mutant MCT gene into a cell, either maintained on a separate plasmid or integrated into the genome of the host cell. If integrated into the genome, such integration can be random, or it can take place by homologous recombination such that the native gene is replaced by the introduced copy, causing the production of the desired compound from the cell to be modulated. In a preferred embodiment, said yields are increased. In another preferred embodiment, said chemical is a fine chemical. In a particularly preferred embodiment, said fine chemical is an amino acid. In especially preferred embodiments, said amino acid is L-lysine.

DETAILED DESCRIPTION OF THE INVENTION

The present invention provides MCT nucleic acid and protein molecules which are involved in the metabolism of cellular membrane components in C. glutamicum or in the transport of compounds across such membranes. The molecules of the invention may be utilized in the modulation of production of fine chemicals from microorganisms, such as C. glutamicum, either directly (e.g., where overexpression or optimization of a fatty acid biosynthesis protein has a direct impact on the yield, production, and/or efficiency of production of the fatty acid from modified C. glutamicum), or may have an indirect impact which nonetheless results in an increase of yield, production, and/or efficiency of production of the desired compound (e.g., where modulation of the metabolism of cell membrane components results in alterations in the yield, production, and/or efficiency of production or the composition of the cell membrane, which in turn may impact the production of one or more fine chemicals). Aspects of the invention are further explicated below.

I. Fine Chemicals

The term 'fine chemical' is art-recognized and includes molecules produced by an organism which have applications in various industries, such as, but not limited to, the pharmaceutical, agriculture, and cosmetics industries. Such compounds include organic acids, such as tartaric acid, itaconic acid, and diaminopimelic acid, both proteinogenic and non-proteinogenic amino acids, purine and pyrimidine bases, nucleosides, and nucleotides (as described e.g. in Kuninaka, A. (1996) Nucleotides and related compounds, p. 561-612, in Biotechnology vol. 6, Rehm et al., eds. VCH: Weinheim, and references contained therein), lipids, both saturated and unsaturated fatty acids (e.g., arachidonic acid), diols (e.g., propane diol, and butane diol), carbohydrates (e.g., hyaluronic acid and trehalose), aromatic compounds (e.g., aromatic amines, vanillin, and indigo), vitamins and cofactors (as described in Ullmann's Encyclopedia of Industrial Chemistry, vol. A27, "Vitamins", p. 443-613 (1996) VCH: Weinheim and references therein; and Ong, A. S., Niki, E. & Packer, L. (1995) "Nutrition, Lipids, Health, and Disease" Proceedings of the UNESCO/Confederation of Scientific and Technological Associations in Malaysia, and the Society for Free Radical Research—Asia, held Sep. 1-3, 1994 at Penang, Malaysia, AOCS Press, (1995)), enzymes, polyketides (Cane et al. (1998) Science 282: 63-68), and all other chemicals described in Gutcho (1983) Chemicals by Fermentation, Noyes Data Corporation, ISBN: 0818805086 and references therein. The metabolism and uses of certain of these fine chemicals are further explicated below.

A. Amino Acid Metabolism and Uses

Amino acids comprise the basic structural units of all proteins, and as such are essential for normal cellular functioning in all organisms. The term "amino acid" is art-recognized. The proteinogenic amino acids, of which there are 20 species, serve as structural units for proteins, in which they are linked by peptide bonds, while the nonproteinogenic amino acids (hundreds of which are known) are not normally found in proteins (see Ulmann's Encyclopedia of Industrial Chemistry, vol. A2, p. 57-97 VCH: Weinheim (1985)). Amino acids may be in the D- or L-optical configuration, though L-amino acids are generally the only type found in naturally-occurring proteins. Biosynthetic and degradative pathways of each of the 20 proteinogenic amino acids have been well characterized in both prokaryotic and eukaryotic cells (see, for example, Stryer, L. Biochemistry, $3^{rd}$ edition, pages 578-590 (1988)). The 'essential' amino acids (histidine, isoleucine, leucine, lysine, methionine, phenylalanine, threonine, tryptophan, and valine), so named because they are generally a nutritional requirement due to the complexity of their biosyntheses, are readily converted by simple biosynthetic pathways to the remaining 11 'non-essential' amino acids (alanine, arginine, asparagine, aspartate, cysteine, glutamate, glutamine, glycine, proline, serine, and tyrosine). Higher animals do retain the ability to synthesize some of these amino acids, but the essential amino acids must be supplied from the diet in order for normal protein synthesis to occur.

Aside from their function in protein biosynthesis, these amino acids are interesting chemicals in their own right, and many have been found to have various applications in the food, feed, chemical, cosmetics, agriculture, and pharmaceutical industries. Lysine is an important amino acid in the nutrition not only of humans, but also of monogastric animals such as poultry and swine. Glutamate is most commonly used as a flavor additive (mono-sodium glutamate, MSG) and is widely used throughout the food industry, as are aspartate, phenylalanine, glycine, and cysteine. Glycine, L-methionine and tryptophan are all utilized in the pharmaceutical industry. Glutamine, valine, leucine, isoleucine, histidine, arginine, proline, serine and alanine are of use in both the pharmaceutical and cosmetics industries. Threonine, tryptophan, and D/L-methionine are common feed additives. (Leuchtenberger, W. (1996) Amino aids—technical technical production and use, p. 466-502 in Rehm et al. (eds.) Biotechnology vol. 6, chapter 14a, VCH: Weinheim). Additionally, these amino acids have been found to be useful as precursors for the synthesis of synthetic amino acids and proteins, such as N-acetylcysteine, S-carboxymethyl-L-cysteine, (S)-5-hydroxytryptophan, and others described in Ulmann's Encyclopedia of Industrial Chemistry, vol. A2, p. 57-97, VCH: Weinheim, 1985.

The biosynthesis of these natural amino acids in organisms capable of producing them, such as bacteria, has been well characterized (for review of bacterial amino acid biosynthesis and regulation thereof, see Umbarger, H. E.(1978) *Ann. Rev. Biochem.* 47: 533-606). Glutamate is synthesized by the reductive amination of α-ketoglutarate, an intermediate in the citric acid cycle. Glutamine, proline, and arginine are each subsequently produced from glutamate. The biosynthesis of serine is a three-step process beginning with 3-phosphoglycerate (an intermediate in glycolysis), and resulting in this amino acid after oxidation, transamination, and hydrolysis steps. Both cysteine and glycine are produced from serine; the former by the condensation of homocysteine with serine, and the latter by the transferal of the side-chain β-carbon atom to tetrahydrofolate, in a reaction catalyzed by serine transhydroxymethylase. Phenylalanine, and tyrosine are synthesized from the glycolytic and pentose phosphate pathway precursors erythrose 4-phosphate and phosphoenolpyruvate in a 9-step biosynthetic pathway that differ only at the final two steps after synthesis of prephenate. Tryptophan is also produced from these two initial molecules, but its synthesis is an 11-step pathway. Tyrosine may also be synthesized from phenylalanine, in a reaction catalyzed by phenylalanine hydroxylase. Alanine, valine, and leucine are all biosynthetic products of pyruvate, the final product of glycolysis. Aspartate is formed from oxaloacetate, an intermediate of the citric acid cycle. Asparagine, methionine, threonine, and lysine are each produced by the conversion of aspartate. Isoleucine is formed from threonine. A complex 9-step pathway results in the production of histidine from 5-phosphoribosyl-1-pyrophosphate, an activated sugar.

Amino acids in excess of the protein synthesis needs of the cell cannot be stored, and are instead degraded to provide intermediates for the major metabolic pathways of the cell (for review see Stryer, L. Biochemistry $3^{rd}$ ed. Ch. 21 "Amino Acid Degradation and the Urea Cycle" p. 495-516 (1988)). Although the cell is able to convert unwanted amino acids into useful metabolic intermediates, amino acid production is costly in terms of energy, precursor molecules, and the enzymes necessary to synthesize them. Thus it is not surprising that amino acid biosynthesis is regulated by feedback inhibition, in which the presence of a particular amino acid serves to slow or entirely stop its own production (for overview of feedback mechanisms in amino acid biosynthetic pathways, see Stryer, L. Biochemistry, $3^{rd}$ ed. Ch. 24: "Biosynthesis of Amino Acids and Heme" p. 575-600 (1988)). Thus, the output of any particular amino acid is limited by the amount of that amino acid present in the cell.

B. Vitamin, Cofactor, and Nutraceutical Metabolism and Uses

Vitamins, cofactors, and nutraceuticals comprise another group of molecules which the higher animals have lost the ability to synthesize and so must ingest, although they are readily synthesized by other organisms such as bacteria. These molecules are either bioactive substances themselves, or are precursors of biologically active substances which may serve as electron carriers or intermediates in a variety of metabolic pathways. Aside from their nutritive value, these compounds also have significant industrial value as coloring agents, antioxidants, and catalysts or other processing aids. (For an overview of the structure, activity, and industrial applications of these compounds, see, for example, Ullman's Encyclopedia of Industrial Chemistry, "Vitamins" vol. A27, p. 443-613, VCH: Weinheim, 1996.) The term "vitamin" is art-recognized, and includes nutrients which are required by the organism for normal functioning, but which that organism cannot synthesize by itself. The group of vitamins may encompass cofactors and nutraceutical compounds. The language "cofactor" includes nonproteinaceous compounds required for a normal enzymatic activity to occur. Such compounds may be organic or inorganic; the cofactor molecules of the invention are preferably organic. The term "nutraceutical" includes dietary supplements having health benefits in plants and animals, particularly humans. Examples of such molecules are vitamins, antioxidants, and also certain lipids (e.g., polyunsaturated fatty acids).

The biosynthesis of these molecules in organisms capable of producing them, such as bacteria, has been largely characterized (Ullman's Encyclopedia of Industrial Chemistry, "Vitamins" vol. A27, p. 443-613, VCH: Weinheim, 1996; Michal, G. (1999) Biochemical Pathways: An Atlas of Biochemistry and Molecular Biology, John Wiley & Sons; Ong, A. S., Niki, E. & Packer, L. (1995) "Nutrition, Lipids, Health, and Disease" Proceedings of the UNESCO/Confederation of Scientific and Technological Associations in Malaysia, and the Society for Free Radical Research—Asia, held Sep. 1-3, 1994 at Penang, Malaysia, AOCS Press: Champaign, IL X, 374 S).

Thiamin (vitamin $B_1$) is produced by the chemical coupling of pyrimidine and thiazole moieties. Riboflavin (vitamin $B_2$) is synthesized from guanosine-5'-triphosphate (GTP) and ribose-5'-phosphate. Riboflavin, in turn, is utilized for the synthesis of flavin mononucleotide (FMN) and flavin adenine dinucleotide (FAD). The family of compounds collectively termed 'vitamin $B_6$' (e.g., pyridoxine, pyridoxamine, pyridoxa-5'-phosphate, and the commercially used pyridoxin hydrochloride) are all derivatives of the common structural unit, 5-hydroxy-6-methylpyridine. Pantothenate (pantothenic acid, (R)-(+)-N-(2,4-dihydroxy-3,3-dimethyl-1-oxobutyl)-β-alanine) can be produced either by chemical synthesis or by fermentation. The final steps in pantothenate biosynthesis consist of the ATP-driven condensation of β-alanine and pantoic acid. The enzymes responsible for the biosynthesis steps for the conversion to pantoic acid, to β-alanine and for the condensation to panthotenic acid are known. The metabolically active form of pantothenate is Coenzyme A, for which the biosynthesis proceeds in 5 enzymatic steps. Pantothenate, pyridoxal-5'-phosphate, cysteine and ATP are the precursors of Coenzyme A. These enzymes not only catalyze the formation of panthothante, but also the production of (R)-pantoic acid, (R)-pantolacton, (R)-panthenol (provitamin $B_5$), pantetheine (and its derivatives) and coenzyme A.

Biotin biosynthesis from the precursor molecule pimeloyl-CoA in microorganisms has been studied in detail and several of the genes involved have been identified. Many of the corresponding proteins have been found to also be involved in Fe-cluster synthesis and are members of the nifS class of proteins. Lipoic acid is derived from octanoic acid, and serves as a coenzyme in energy metabolism, where it becomes part of the pyruvate dehydrogenase complex and the α-ketoglutarate dehydrogenase complex. The folates are a group of substances which are all derivatives of folic acid, which is turn is derived from L-glutamic acid, p-aminobenzoic acid and 6-methylpterin. The biosynthesis of folic acid and its derivatives, starting from the metabolism intermediates guanosine-5'-triphosphate (GTP), L-glutamic acid and p-amino-benzoic acid has been studied in detail in certain microorganisms.

Corrinoids (such as the cobalamines and particularly vitamin $B_{12}$) and porphyrines belong to a group of chemicals characterized by a tetrapyrole ring system. The biosynthesis of vitamin $B_{12}$ is sufficiently complex that it has not yet been completely characterized, but many of the enzymes and substrates involved are now known. Nicotinic acid (nicotinate), and nicotinamide are pyridine derivatives which are also termed 'niacin'. Niacin is the precursor of the important coenzymes NAD (nicotinamide adenine dinucleotide) and NADP (nicotinamide adenine dinucleotide phosphate) and their reduced forms.

The large-scale production of these compounds has largely relied on cell-free chemical syntheses, though some of these chemicals have also been produced by large-scale culture of microorganisms, such as riboflavin, Vitamin $B_6$, pantothenate, and biotin. Only Vitamin $B_{12}$ is produced solely by fermentation, due to the complexity of its synthesis. In vitro methodologies require significant inputs of materials and time, often at great cost.

C. Purine, Pyrimidine, Nucleoside and Nucleotide Metabolism and Uses

Purine and pyrimidine metabolism genes and their corresponding proteins are important targets for the therapy of tumor diseases and viral infections. The language "purine" or "pyrimidine" includes the nitrogenous bases which are constituents of nucleic acids, co-enzymes, and nucleotides. The term "nucleotide" includes the basic structural units of nucleic acid molecules, which are comprised of a nitrogenous base, a pentose sugar (in the case of RNA, the sugar is ribose; in the case of DNA, the sugar is D-deoxyribose), and phosphoric acid. The language "nucleoside" includes molecules which serve as precursors to nucleotides, but which are lacking the phosphoric acid moiety that nucleotides possess. By inhibiting the biosynthesis of these molecules, or their mobilization to form nucleic acid molecules, it is possible to inhibit RNA and DNA synthesis; by inhibiting this activity in a fashion targeted to cancerous cells, the ability of tumor cells to divide and replicate may be inhibited. Additionally, there are nucleotides which do not form nucleic acid molecules, but rather serve as energy stores (i.e., AMP) or as coenzymes (i.e., FAD and NAD).

Several publications have described the use of these chemicals for these medical indications, by influencing purine and/or pyrimidine metabolism (e.g. Christopherson, R. I. and Lyons, S. D. (1990) "Potent inhibitors of de novo pyrimidine and purine biosynthesis as chemotherapeutic agents." Med. Res. Reviews 10: 505-548). Studies of enzymes involved in purine and pyrimidine metabolism have been focused on the development of new drugs which can be used, for example, as immunosuppressants or antiproliferants (Smith, J. L., (1995) "Enzymes in nucleotide synthesis." Curr. Opin. Struct. Biol. 5: 752-757; (1995) Biochem Soc. Transact. 23: 877-902). However, purine and pyrimidine bases, nucleosides and nucleotides have other utilities: as intermediates in the biosynthesis of several fine chemicals (e.g., thiamine, S-adenosyl-methionine, folates, or riboflavin), as energy carriers for the cell (e.g., ATP or GTP), and for chemicals themselves, commonly used as flavor enhancers (e.g., IMP or GMP) or for several medicinal applications (see, for example, Kuninaka, A. (1996) Nucleotides and Related Compounds in Biotechnology vol. 6, Rehm et al., eds. VCH: Weinheim, p. 561-612). Also, enzymes involved in purine, pyrimidine, nucleoside, or nucleotide metabolism are increasingly serving as targets against which chemicals for crop protection, including fungicides, herbicides and insecticides, are developed.

The metabolism of these compounds in bacteria has been characterized (for reviews see, for example, Zalkin, H. and Dixon, J. E. (1992) "de novo purine nucleotide biosynthesis", in: Progress in Nucleic Acid Research and Molecular Biology, vol. 42, Academic Press:, p. 259-287; and Michal, G. (1999) "Nucleotides and Nucleosides", Chapter 8 in: Biochemical Pathways: An Atlas of Biochemistry and Molecular Biology, Wiley: New York). Purine metabolism has been the subject of intensive research, and is essential to the normal functioning of the cell. Impaired purine metabolism in higher animals can cause severe disease, such as gout. Purine nucleotides are synthesized from ribose-5-phosphate, in a series of steps through the intermediate compound inosine-5'-phosphate (IMP), resulting in the production of guanosine-5'-monophosphate (GMP) or adenosine-5'-monophosphate (AMP), from which the triphosphate forms utilized as nucleotides are readily formed. These compounds are also utilized as energy stores, so their degradation provides energy for many different biochemical processes in the cell. Pyrimidine biosynthesis proceeds by the formation of uridine-5'-monophosphate (UMP) from ribose-5-phosphate. UMP, in turn, is converted to cytidine-5'-triphosphate (CTP). The deoxy-forms of all of these nucleotides are produced in a one step reduction reaction from the diphosphate ribose form of the nucleotide to the diphosphate deoxyribose form of the nucleotide. Upon phosphorylation, these molecules are able to participate in DNA synthesis.

D. Trehalose Metabolism and Uses

Trehalose consists of two glucose molecules, bound in $\alpha$, $\alpha$-1,1 linkage. It is commonly used in the food industry as a sweetener, an additive for dried or frozen foods, and in beverages. However, it also has applications in the pharmaceutical, cosmetics and biotechnology industries (see, for example, Nishimoto et al., (1998) U.S. Pat. No. 5,759,610; Singer, M. A. and Lindquist, S. (1998) Trends Biotech. 16: 460-467; Paiva, C. L. A. and Panek, A. D. (1996) Biotech. Ann. Rev. 2: 293-314; and Shiosaka, M. (1997) J. Japan 172: 97-102). Trehalose is produced by enzymes from many microorganisms and is naturally released into the surrounding medium, from which it can be collected using methods known in the art.

II. Membrane Biosynthesis and Transmembrane Transport

Cellular membranes serve a variety of functions in a cell. First and foremost, a membrane differentiates the contents of a cell from the surrounding environment, thus giving integrity to the cell. Membranes may also serve as barriers to the influx of hazardous or unwanted compounds, and also to the efflux of desired compounds. Cellular membranes are by nature impervious to the unfacilitated diffusion of hydrophilic compounds such as proteins, water molecules and ions due to their structure: a bilayer of lipid molecules in which the polar head groups face outwards (towards the exterior and interior of the cell, respectively) and the non-polar tails face inwards at the center of the bilayer, forming a hydrophobic core (for a general review of membrane structure and function, see Gennis, R. B. (1989) Biomembranes, Molecular Structure and Function, Springer: Heidelberg). This barrier enables cells to maintain a relatively higher concentration of desired compounds and a relatively lower concentration of undesired compounds than are contained within the surrounding medium, since the diffusion of these compounds is effectively blocked by the membrane. However, the membrane also presents an effective barrier to the import of desired compounds and the export of waste molecules. To overcome this difficulty, cellular membranes incorporate many kinds of transporter proteins which are able to facilitate the transmembrane transport of different kinds of compounds. There are two general classes of these transport proteins: pores or channels and transporters. The former are integral membrane proteins, sometimes complexes of proteins, which form a regulated hole through the membrane. This regulation, or 'gating' is generally specific to the molecules to be transported by the pore or channel, rendering these transmembrane constructs selectively permeable to a specific class of substrates; for example, a potassium channel is constructed such that only ions having a like charge and size to that of potassium may pass through. Channel and pore proteins tend to have discrete hydrophobic and hydrophilic domains, such that the hydrophobic face of the protein may associate with the interior of the membrane while the hydrophilic face lines the interior of the channel, thus providing a sheltered hydrophilic environment through which the selected hydrophilic molecule may pass. Many such pores/channels are known in the art, including those for potassium, calcium, sodium, and chloride ions.

This pore and channel-mediated system of facilitated diffusion is limited to very small molecules, such as ions, because pores or channels large enough to permit the passage of whole proteins by facilitated diffusion would be unable to prevent the passage of smaller hydrophilic molecules as well. Transport of molecules by this process is sometimes termed 'facilitated diffusion' since the driving force of a concentration gradient is required for the transport to occur. Permeases also permit facilitated diffusion of larger molecules, such as glucose or other sugars, into the cell when the concentration of these molecules on one side of the membrane is greater than that on the other (also called 'uniport'). In contrast to pores or channels, these integral membrane proteins (often having between 6-14 membrane-spanning α-helices) do not form open channels through the membrane, but rather bind to the target molecule at the surface of the membrane and then undergo a conformational shift such that the target molecule is released on the opposite side of the membrane.

However, cells frequently require the import or export of molecules against the existing concentration gradient ('active transport'), a situation in which facilitated diffusion cannot occur. There are two general mechanisms used by cells for such membrane transport: symport or antiport, and energy-coupled transport such as that mediated by the ABC transporters. Symport and antiport systems couple the movement of two different molecules across the membrane (via permeases having two separate binding sites for the two different molecules); in symport, both molecules are transported in the same direction, while in antiport, one molecule is imported while the other is exported. This is possible energetically because one of the two molecules moves in accordance with a concentration gradient, and this energetically favorable event is permitted only upon concomitant movement of a desired compound against the prevailing concentration gradient. Single molecules may be transported across the membrane against the concentration gradient in an energy-driven process, such as that utilized by the ABC transporters. In this system, the transport protein located in the membrane has an ATP-binding cassette; upon binding of the target molecule, the ATP is converted to ADP+Pi, and the resulting release of energy is used to drive the movement of the target molecule to the opposite face of the membrane, facilitated by the transporter. For more detailed descriptions of all of these transport systems, see: Bamberg, E. et al., (1993) "Charge transport of ion pumps on lipid bilayer membranes", *Q. Rev. Biophys.* 26: 1-25; Findlay, J. B. C. (1991) "Structure and function in membrane transport systems", *Curr. Opin. Struct. Biol.* 1:804-810; Higgins, C. F. (1992) "ABC transporters from microorganisms to man", *Ann. Rev. Cell Biol.* 8: 67-113; Gennis, R. B. (1989) "Pores, Channels and Transporters", in: Biomembranes, Molecular Structure and Function, Springer: Heidelberg, p. 270-322; and Nikaido, H. and Saier, H. (1992) "Transport proteins in bacteria: common themes in their design", *Science* 258: 936-942, and references contained within each of these references.

The synthesis of membranes is a well-characterized process involving a number of components, the most important of which are lipid molecules. Lipid synthesis may be divided into two parts: the synthesis of fatty acids and their attachment to sn-glycerol-3-phosphate, and the addition or modification of a polar head group. Typical lipids utilized in bacterial membranes include phospholipids, glycolipids, sphingolipids, and phosphoglycerides. Fatty acid synthesis begins with the conversion of acetyl CoA either to malonyl CoA by acetyl CoA carboxylase, or to acetyl-ACP by acetyltransacylase. Following a condensation reaction, these two product molecules together form acetoacetyl-ACP, which is converted by a series of condensation, reduction and dehydration reactions to yield a saturated fatty acid molecule having a desired chain length. The production of unsaturated fatty acids from such molecules is catalyzed by specific desaturases either aerobically, with the help of molecular oxygen, or anaerobically (for reference on fatty acid synthesis, see F. C. Neidhardt et al. (1996) *E. coli* and Salmonella. ASM Press: Washington, D.C., p. 612-636 and references contained therein; Lengeler et al. (eds) (1999) Biology of Procaryotes. Thieme: Stuttgart, N.Y., and references contained therein; and Magnuson, K. et al., (1993) *Microbiological Reviews* 57: 522-542, and references contained therein). The cyclopropane fatty acids (CFA) are synthesized by a specific CFA-synthase using SAM as a cosubstrate. Branched chain fatty acids are synthesized from branched chain amino acids that are deaminated to yield branched chain 2-oxo-acids (see Lengeler et al., eds. (1999) Biology of Procaryotes. Thieme: Stuttgart, N.Y., and references contained therein). Another essential step in lipid synthesis is the transfer of fatty acids onto the polar head groups by, for example, glycerol-phosphate-acyltransferases. The combination of various precursor molecules and biosynthetic enzymes results in the production of different fatty acid molecules, which has a profound effect on the composition of the membrane.

III. Elements and Methods of the Invention

The present invention is based, at least in part, on the discovery of novel molecules, referred to herein as MCT nucleic acid and protein molecules, which control the production of cellular membranes in *C. glutamicum* and govern the movement of molecules across such membranes. In one embodiment, the MCT molecules participate in the metabolism of compounds necessary for the construction of cellular membranes in *C. glutamicum*, or in the transport of molecules across these membranes. In a preferred embodiment, the activity of the MCT molecules of the present invention to regulate membrane component production and membrane transport has an impact on the production of a desired fine chemical by this organism. In a particularly preferred embodiment, the MCT molecules of the invention are modulated in activity, such that the *C. glutamicum* metabolic pathways which the MCT proteins of the invention regulate are modulated in yield, production, and/or efficiency of production and the transport of compounds through the membranes is altered in efficiency, which either directly or indirectly modulates the yield, production, and/or efficiency of production of a desired fine chemical by *C. glutamicum*.

The language, "MCT protein" or "MCT polypeptide" includes proteins which participate in the metabolism of compounds necessary for the construction of cellular membranes in *C. glutamicum*, or in the transport of molecules across these membranes. Examples of MCT proteins include those encoded by the MCT genes set forth in Table 1 and Appendix A. The terms "MCT gene" or "MCT nucleic acid sequence" include nucleic acid sequences encoding an MCT protein, which consist of a coding region and also corresponding untranslated 5' and 3' sequence regions. Examples of MCT genes include those set forth in Table 1. The terms "production" or "productivity" are art-recognized and include the concentration of the fermentation product (for example, the desired fine chemical) formed within a given time and a given fermentation volume (e.g., kg product per hour per liter). The term "efficiency of production" includes the time required for a particular level of production to be achieved (for example, how long it takes for the cell to attain a particular rate of output of a fine chemical). The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules, or of useful recovered molecules of that compound in a given amount of culture over a given amount of time is increased. The terms "biosynthesis" or a "biosynthetic pathway" are art-recognized and include the synthesis of a compound, preferably an organic compound, by a cell from intermediate compounds in what may be a multistep and highly regulated process. The terms "degradation" or a "degradation pathway" are art-recognized and include the breakdown of a compound, preferably an organic compound, by a cell to degradation products (generally speaking, smaller or less complex molecules) in what may be a multistep and highly regulated process. The language "metabolism" is art-recognized and includes the totality of the biochemical reactions that take place in an organism. The metabolism of a particular compound, then, (e.g., the metabolism of an amino acid such as glycine) comprises the overall biosynthetic, modification, and degradation pathways in the cell related to this compound.

In another embodiment, the MCT molecules of the invention are capable of modulating the production of a desired molecule, such as a fine chemical, in a microorganism such as *C. glutamicum*. There are a number of mechanisms by which the alteration of an MCT protein of the invention may directly affect the yield, production, and/or efficiency of production of a fine chemical from a *C. glutamicum* strain incorporating such an altered protein. Those MCT proteins involved in the export of fine chemical molecules from the cell may be increased in number or activity such that greater quantities of these compounds are secreted to the extracellular medium, from which they are more readily recovered. Similarly, those MCT proteins involved in the import of nutrients necessary for the biosynthesis of one or more fine chemicals (e.g., phosphate, sulfate, nitrogen compounds, etc.) may be increased in number or activity such that these precursor, cofactor, or intermediate compounds are increased in concentration within the cell. Further, fatty acids and lipids themselves are desirable fine chemicals; by optimizing the activity or increasing the number of one or more MCT proteins of the invention which participate in the biosynthesis of these compounds, or by impairing the activity of one or more MCT proteins which are involved in the degradation of these compounds, it may be possible to increase the yield, production, and/or efficiency of production of fatty acid and lipid molecules from *C. glutamicum*.

The mutagenesis of one or more MCT genes of the invention may also result in MCT proteins having altered activities which indirectly impact the production of one or more desired fine chemicals from *C. glutamicum*. For example, MCT proteins of the invention involved in the export of waste products may be increased in number or activity such that the normal metabolic wastes of the cell (possibly increased in quantity due to the overproduction of the desired fine chemical) are efficiently exported before they are able to damage nucleotides and proteins within the cell (which would decrease the viability of the cell) or to interfere with fine chemical biosynthetic pathways (which would decrease the yield, production, or efficiency of production of the desired fine chemical). Further, the relatively large intracellular quantities of the desired fine chemical may in itself be toxic to the cell, so by increasing the activity or number of transporters able to export this compound from the cell, one may increase the viability of the cell in culture, in turn leading to a greater number of cells in the culture producing the desired fine chemical. The MCT proteins of the invention may also be manipulated such that the relative amounts of different lipid and fatty acid molecules are produced. This may have a profound effect on the lipid composition of the membrane of the cell. Since each type of lipid has different physical properties, an alteration in the lipid composition of a membrane may significantly alter membrane fluidity. Changes in membrane fluidity can impact the transport of molecules across the membrane, as well as the integrity of the cell, both of which have a profound effect on the production of fine chemicals from *C. glutamicum* in large-scale fermentative culture.

The isolated nucleic acid sequences of the invention are contained within the genome of a *Corynebacterium glutamicum* strain available through the American Type Culture Collection, given designation ATCC 13032. The nucleotide sequence of the isolated *C. glutamicum* MCT DNAs and the predicted amino acid sequences of the *C. glutamicum* MCT proteins are shown in Appendices A and B, respectively. Computational analyses were performed which classified and/or identified these nucleotide sequences as sequences which encode proteins involved in the metabolism of cellular membrane components or proteins involved in the transport of compounds across such membranes.

The present invention also pertains to proteins which have an amino acid sequence which is substantially homologous to an amino acid sequence of Appendix B. As used herein, a protein which has an amino acid sequence which is substantially homologous to a selected amino acid sequence is least about 50% homologous to the selected amino acid sequence, e.g., the entire selected amino acid sequence. A protein which has an amino acid sequence which is substantially homologous to a selected amino acid sequence can also be least about 50-60%, preferably at least about 60-70%, and more preferably at least about 70-80%, 80-90%, or 90-95%, and most preferably at least about 96%, 97%, 98%, 99% or more homologous to the selected amino acid sequence.

The MCT protein or a biologically active portion or fragment thereof of the invention can participate in the metabolism of compounds necessary for the construction of cellular membranes in *C. glutamicum*, or in the transport of molecules across these membranes, or have one or more of the activities set forth in Table 1.

Various aspects of the invention are described in further detail in the following subsections:

A. Isolated Nucleic Acid Molecules

One aspect of the invention pertains to isolated nucleic acid molecules that encode MCT polypeptides or biologically active portions thereof, as well as nucleic acid fragments sufficient for use as hybridization probes or primers for the identification or amplification of MCT-encoding nucleic acid (e.g., MCT DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 100 nucleotides of sequence upstream from the 5' end of the coding region and at least about 20 nucleotides of sequence downstream from the 3'end of the coding region of the gene. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated MCT nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g, a *C. glutamicum* cell). Moreover, an "isolated" nucleic acid molecule, such as a DNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having a nucleotide sequence of Appendix A, or a portion thereof, can be isolated using standard molecular biology techniques and the sequence information provided herein. For example, a *C. glutamicum* MCT DNA can be isolated from a *C. glutamicum* library using all or portion of one of the sequences of Appendix A as a hybridization probe and standard hybridization techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989). Moreover, a nucleic acid molecule encompassing all or a portion of one of the sequences of Appendix A can be isolated by the polymerase chain reaction using oligonucleotide primers designed based upon this sequence (e.g., a nucleic acid molecule encompassing all or a portion of one of the sequences of Appendix A can be isolated by the polymerase chain reaction using oligonucleotide primers designed based upon this same sequence of Appendix A). For example, mRNA can be isolated from normal endothelial cells (e.g., by the guanidinium-thiocyanate extraction procedure of Chirgwin et al. (1979) *Biochemistry* 18: 5294-5299) and DNA can be prepared using reverse transcriptase (e.g., Moloney MLV reverse transcriptase, available from Gibco/ BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in Appendix A. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an MCT nucleotide sequence can be prepared by standard synthetic techniques, e.g., using an automated DNA synthesizer.

In a preferred embodiment, an isolated nucleic acid molecule of the invention comprises one of the nucleotide sequences shown in Appendix A. The sequences of Appendix A correspond to the *Corynebacterium glutamicum* MCT DNAs of the invention. This DNA comprises sequences encoding MCT proteins (i.e., the "coding region", indicated in each sequence in Appendix A), as well as 5' untranslated sequences and 3' untranslated sequences, also indicated in Appendix A. Alternatively, the nucleic acid molecule can comprise only the coding region of any of the sequences in Appendix A.

For the purposes of this application, it will be understood that each of the sequences set forth in Appendix A has an identifying RXA, RXN, RXS, or RXC number having the designation "RXA", "RXN", "RXS" or "RXC" followed by 5 digits (i.e., RXA02099, RXN03097, RXS00148, or RXC01748). Each of these sequences comprises up to three parts: a 5' upstream region, a coding region, and a downstream region. Each of these three regions is identified by the same RXA, RXN, RXS, or RXC designation to eliminate confusion. The recitation "one of the sequences in Appendix A", then, refers to any of the sequences in Appendix A, which may be distinguished by their differing RXA, RXN, RXS, or RXC designations. The coding region of each of these sequences is translated into a corresponding amino acid sequence, which is set forth in Appendix B. The sequences of Appendix B are identified by the same RXA, RXN, RXS, or RXC designations as Appendix A, such that they can be readily correlated. For example, the amino acid sequences in Appendix B designated RXA02099, RXN03097, RXS00148, and RXC01748 are translations of the coding region of the nucleotide sequences of nucleic acid molecules RXA02099, RXN03097, RXS00148, and RXC01748, respectively, in Appendix A. Each of the RXA, RXN, RXS, and RXC nucleotide and amino acid sequences of the invention has also been assigned a SEQ ID NO, as indicated in Table 1. For example, as set forth in Table 1, the nucleotide sequence of RXA00104 is SEQ ID NO:5, and the amino acid sequence of RXA00104 is SEQ ID NO:6.

Several of the genes of the invention are "F-designated genes". An F-designated gene includes those genes set forth in Table 1 which have an 'F' in front of the RXA, RXN, RXS, or RXC designation. For example, SEQ ID NO:11, designated, as indicated on Table 1, as "F RXA02581", is an F-designated gene, as are SEQ ID NOs: 31, 33, and 43 (designated on Table 1 as "F RXA02487", "F RXA02490", and "F RXA02809", respectively).

In one embodiment, the nucleic acid molecules of the present invention are not intended to include those compiled in Table 2. In the case of the dapD gene, a sequence for this gene was published in Wehrmann, A., et al. (1998) *J. Bacteriol.* 180(12): 3159-3165. However, the sequence obtained by the inventors of the present application is significantly longer than the published version. It is believed that the published version relied on an incorrect start codon, and thus represents only a fragment of the actual coding region.

In another preferred embodiment, an isolated nucleic acid molecule of the invention comprises a nucleic acid molecule which is a complement of one of the nucleotide sequences shown in Appendix A, or a portion thereof. A nucleic acid molecule which is complementary to one of the nucleotide sequences shown in Appendix A is one which is sufficiently complementary to one of the nucleotide sequences shown in Appendix A such that it can hybridize to one of the nucleotide sequences shown in Appendix A, thereby forming a stable duplex.

In still another preferred embodiment, an isolated nucleic acid molecule of the invention comprises a nucleotide sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more homologous to a nucleotide sequence shown in Appendix A, or a portion thereof. Ranges and identity values intermediate to the above-recited ranges, (e.g., 70-90% identical or 80-95% identical) are also intended to be encompassed by the present invention. For example, ranges of identity values using a combination of any of the above values recited as upper and/or lower limits are intended to be included. In an additional preferred embodiment, an isolated nucleic acid molecule of the invention comprises a nucleotide sequence which hybridizes, e.g., hybridizes under stringent conditions, to one of the nucleotide sequences shown in Appendix A, or a portion thereof.

Moreover, the nucleic acid molecule of the invention can comprise only a portion of the coding region of one of the sequences in Appendix A, for example a fragment which can be used as a probe or primer or a fragment encoding a biologically active portion of an MCT protein. The nucleotide sequences determined from the cloning of the MCT genes from *C. glutamicum* allows for the generation of probes and primers designed for use in identifying and/or cloning MCT homologues in other cell types and organisms, as well as MCT homologues from other *Corynebacteria* or related species. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in Appendix A, an anti-sense sequence of one of the sequences set forth in Appendix A, or naturally occurring mutants thereof. Primers based on a nucleotide sequence of Appendix A can be used in PCR reactions to clone MCT homologues. Probes based on the MCT nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells which misexpress an MCT protein, such as by measuring a level of an MCT-encoding nucleic acid in a sample of cells, e.g., detecting MCT mRNA levels or determining whether a genomic MCT gene has been mutated or deleted.

In one embodiment, the nucleic acid molecule of the invention encodes a protein or portion thereof which includes an amino acid sequence which is sufficiently homologous to an amino acid sequence of Appendix B such that the protein or portion thereof maintains the ability to participate in the metabolism of compounds necessary for the construction of cellular membranes in *C. glutamicum*, or in the transport of molecules across these membranes. As used herein, the language "sufficiently homologous" refers to proteins or portions thereof which have amino acid sequences which include a minimum number of identical or equivalent (e.g., an amino acid residue which has a similar side chain as an amino acid residue in one of the sequences of Appendix B) amino acid residues to an amino acid sequence of Appendix B such that the protein or portion thereof is able to participate in the metabolism of compounds necessary for the construction of cellular membranes in *C. glutamicum*, or in the transport of molecules across these membranes. Protein members of such membrane component metabolic pathways or membrane transport systems, as described herein, may play a role in the production and secretion of one or more fine chemicals. Examples of such activities are also described herein. Thus, "the function of an MCT protein" contributes either directly or indirectly to the yield, production, and/or efficiency of production of one or more fine chemicals. Examples of MCT protein activities are set forth in Table 1.

In another embodiment, the protein is at least about 50-60%, preferably at least about 60-70%, and more preferably at least about 70-80%, 80-90%, 90-95%, and most preferably at least about 96%, 97%, 98%, 99% or more homologous to an entire amino acid sequence of Appendix B.

Portions of proteins encoded by the MCT nucleic acid molecules of the invention are preferably biologically active portions of one of the MCT proteins. As used herein, the term "biologically active portion of an MCT protein" is intended to include a portion, e.g., a domain/motif, of an MCT protein that participates in the metabolism of compounds necessary for the construction of cellular membranes in *C. glutamicum*, or in the transport of molecules across these membranes, or has an activity as set forth in Table 1. To determine whether an MCT protein or a biologically active portion thereof can participate in the metabolism of compounds necessary for the construction of cellular membranes in *C. glutamicum*, or in the transport of molecules across these membranes, an assay of enzymatic activity may be performed. Such assay methods are well known to those of ordinary skill in the art, as detailed in Example 8 of the Exemplification.

Additional nucleic acid fragments encoding biologically active portions of an MCT protein can be prepared by isolating a portion of one of the sequences in Appendix B, expressing the encoded portion of the MCT protein or peptide (e.g., by recombinant expression in vitro) and assessing the activity of the encoded portion of the MCT protein or peptide.

The invention further encompasses nucleic acid molecules that differ from one of the nucleotide sequences shown in Appendix A (and portions thereof) due to degeneracy of the genetic code and thus encode the same MCT protein as that encoded by the nucleotide sequences shown in Appendix A. In another embodiment, an isolated nucleic acid molecule of the invention has a nucleotide sequence encoding a protein having an amino acid sequence shown in Appendix B. In a still further embodiment, the nucleic acid molecule of the invention encodes a full length *C. glutamicum* protein which is substantially homologous to an amino acid sequence of Appendix B (encoded by an open reading frame shown in Appendix A).

It will be understood by one of ordinary skill in the art that in one embodiment the sequences of the invention are not meant to include the sequences of the prior art, such as those Genbank sequences set forth in Tables 2 or 4 which were available prior to the present invention. In one embodiment, the invention includes nucleotide and amino acid sequences having a percent identity to a nucleotide or amino acid sequence of the invention which is greater than that of a sequence of the prior art (e.g., a Genbank sequence (or the protein encoded by such a sequence) set forth in Tables 2 or 4). For example, the invention includes a nucleotide sequence which is greater than and/or at least 38% identical to the nucleotide sequence designated RXA01420 (SEQ ID NO:7), a nucleotide sequence which is greater than and/or at least 43% identical to the nucleotide sequence designated RXA00104 (SEQ ID NO:5), and a nucleotide sequence which is greater than and/or at least 45% identical to the nucleotide sequence designated RXA02173 (SEQ ID NO:25). One of ordinary skill in the art would be able to calculate the lower threshold of percent identity for any given sequence of the invention by examining the GAP-calculated percent identity scores set forth in Table 4 for each of the three top hits for the given sequence, and by subtracting the highest GAP-calculated percent identity from 100 percent. One of ordinary skill in the art will also appreciate that nucleic acid and amino acid sequences having percent identities greater than the lower threshold so calculated (e.g., at least 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more identical) are also encompassed by the invention.

In addition to the C. glutamicum MCT nucleotide sequences shown in Appendix A, it will be appreciated by one of ordinary skill in the art that DNA sequence polymorphisms that lead to changes in the amino acid sequences of MCT proteins may exist within a population (e.g., the C. glutamicum population). Such genetic polymorphism in the MCT gene may exist among individuals within a population due to natural variation. As used herein, the terms "gene" and "recombinant gene" refer to nucleic acid molecules comprising an open reading frame encoding an MCT protein, preferably a C. glutamicum MCT protein. Such natural variations can typically result in 1-5% variance in the nucleotide sequence of the MCT gene. Any and all such nucleotide variations and resulting amino acid polymorphisms in MCT that are the result of natural variation and that do not alter the functional activity of MCT proteins are intended to be within the scope of the invention.

Nucleic acid molecules corresponding to natural variants and non-C. glutamicum homologues of the C. glutamicum MCT DNA of the invention can be isolated based on their homology to the C. glutamicum MCT nucleic acid disclosed herein using the C. glutamicum DNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising a nucleotide sequence of Appendix A. In other embodiments, the nucleic acid is at least 30, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those of ordinary skill in the art and can be found in Current Protocols in Molecular Biology, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a sequence of Appendix A corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural C. glutamicum MCT protein.

In addition to naturally-occurring variants of the MCT sequence that may exist in the population, one of ordinary skill in the art will further appreciate that changes can be introduced by mutation into a nucleotide sequence of Appendix A, thereby leading to changes in the amino acid sequence of the encoded MCT protein, without altering the functional ability of the MCT protein. For example, nucleotide substitutions leading to amino acid substitutions at "non-essential" amino acid residues can be made in a sequence of Appendix A. A "non-essential" amino acid residue is a residue that can be altered from the wild-type sequence of one of the MCT proteins (Appendix B) without altering the activity of said MCT protein, whereas an "essential" amino acid residue is required for MCT protein activity. Other amino acid residues, however, (e.g., those that are not conserved or only semi-conserved in the domain having MCT activity) may not be essential for activity and thus are likely to be amenable to alteration without altering MCT activity.

Accordingly, another aspect of the invention pertains to nucleic acid molecules encoding MCT proteins that contain changes in amino acid residues that are not essential for MCT activity. Such MCT proteins differ in amino acid sequence from a sequence contained in Appendix B yet retain at least one of the MCT activities described herein. In one embodiment, the isolated nucleic acid molecule comprises a nucleotide sequence encoding a protein, wherein the protein comprises an amino acid sequence at least about 50% homologous to an amino acid sequence of Appendix B and is capable of participate in the metabolism of compounds necessary for the construction of cellular membranes in C. glutamicum, or in the transport of molecules across these membranes, or has one or more activities set forth in Table 1. Preferably, the protein encoded by the nucleic acid molecule is at least about 50-60% homologous to one of the sequences in Appendix B, more preferably at least about 60-70% homologous to one of the sequences in Appendix B, even more preferably at least about 70-80%, 80-90%, 90-95% homologous to one of the sequences in Appendix B, and most preferably at least about 96%, 97%, 98%, or 99% homologous to one of the sequences in Appendix B.

To determine the percent homology of two amino acid sequences (e.g., one of the sequences of Appendix B and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences of Appendix B) is occupied by the same amino acid residue or nucleotide as the corresponding position in the other sequence (e.g., a mutant form of the sequence selected from Appendix B), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

An isolated nucleic acid molecule encoding an MCT protein homologous to a protein sequence of Appendix B can be created by introducing one or more nucleotide substitutions, additions or deletions into a nucleotide sequence of Appendix A such that one or more amino acid substitutions, additions or deletions are introduced into the encoded protein. Mutations can be introduced into one of the sequences of Appendix A by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an MCT protein is preferably replaced with another amino acid residue from the same side chain family. Alternatively, in another embodiment, mutations can be introduced randomly along all or part of an MCT coding sequence, such as by saturation mutagenesis, and the resultant mutants can be screened for an MCT activity described herein to identify mutants that retain MCT activity. Following mutagenesis of one of the sequences of Appendix A, the encoded protein can be expressed recombinantly and the activity of the protein can be determined using, for example, assays described herein (see Example 8 of the Exemplification).

In addition to the nucleic acid molecules encoding MCT proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire MCT coding strand, or to only a portion thereof. In one embodiment, an antisense nucleic acid molecule is antisense to a "coding region" of the coding strand of a nucleotide sequence encoding an MCT protein. The term "coding region" refers to the region of the nucleotide sequence comprising codons which are translated into amino acid residues (e.g., the entire coding region of SEQ ID NO:5 (RXA00104 in Appendix A) comprises nucleotides 1 to 756). In another embodiment, the antisense nucleic acid molecule is antisense to a "noncoding region" of the coding strand of a nucleotide sequence encoding MCT. The term "noncoding region" refers to 5' and 3' sequences which flank the coding region that are not translated into amino acids (i.e., also referred to as 5' and 3' untranslated regions).

Given the coding strand sequences encoding MCT disclosed herein (e.g., the sequences set forth in Appendix A), antisense nucleic acids of the invention can be designed according to the rules of Watson and Crick base pairing. The antisense nucleic acid molecule can be complementary to the entire coding region of MCT mRNA, but more preferably is an oligonucleotide which is antisense to only a portion of the coding or noncoding region of MCT mRNA. For example, the antisense oligonucleotide can be complementary to the region surrounding the translation start site of MCT mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding an MCT protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave MCT mRNA transcripts to thereby inhibit translation of MCT mRNA. A ribozyme having specificity for an MCT-encoding nucleic acid can be designed based upon the nucleotide sequence of an MCT DNA disclosed herein (i.e., SEQ ID NO. 5 (RXA00104) in Appendix A)). For example, a derivative of a *Tetrahymena* L-19 IVS RNA can be constructed in which the nucleotide sequence of the active site is complementary to the nucleotide sequence to be cleaved in an MCT-encoding mRNA. See, e.g., Cech et al. U.S. Pat. No. 4,987,071 and Cech et al. U.S. Pat. No. 5,116,742. Alternatively, MCT mRNA can be used to select a catalytic RNA having a specific ribonuclease activity from a pool of RNA molecules. See, e.g., Bartel, D. and Szostak, J. W. (1993) *Science* 261:1411-1418.

Alternatively, MCT gene expression can be inhibited by targeting nucleotide sequences complementary to the regulatory region of an MCT nucleotide sequence (e.g., an MCT promoter and/or enhancers) to form triple helical structures that prevent transcription of an MCT gene in target cells. See generally, Helene, C. (1991) *Anticancer Drug Des.* 6(6): 569-84; Helene, C. et al. (1992) *Ann. N.Y Acad. Sci.* 660: 27-36; and Maher, L. J. (1992) *Bioassays* 14(12):807-15.

B. Recombinant Expression Vectors and Host Cells

Another aspect of the invention pertains to vectors, preferably expression vectors, containing a nucleic acid encoding an MCT protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells. Preferred regulatory sequences are, for example, promoters such as cos-, tac-, trp-, tet-, trp-tet-, lpp-, lac-, lpp-lac-, lacI$^q$-, T7-, T5-, T3-, gal-, trc-, ara-, SP6-, arny, SPO2, λ-$P_R$- or λ $P_L$, which are used preferably in bacteria. Additional regulatory sequences are, for example, promoters from yeasts and fungi, such as ADC1, MFα, AC, P-60, CYC1, GAPDH, TEF, rp28, ADH, promoters from plants such as CaMV/35S, SSU, OCS, lib4, usp, STLS1, B33, nos or ubiquitin- or phaseolin-promoters. It is also possible to use artificial promoters. It will be appreciated by one of ordinary skill in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., MCT proteins, mutant forms of MCT proteins, fusion proteins, etc.).

The recombinant expression vectors of the invention can be designed for expression of MCT proteins in prokaryotic or eukaryotic cells. For example, MCT genes can be expressed in bacterial cells such as *C. glutamicum*, insect cells (using baculovirus expression vectors), yeast and other fungal cells (see Romanos, M. A. et al. (1992) "Foreign gene expression in yeast: a review", *Yeast* 8: 423-488; van den Hondel, C. A. M. J. J. et al (1991) "Heterologous gene expression in filamentous fungi" in: More Gene Manipulations in Fungi, J. W. Bennet & L. L. Lasure, eds., p. 396-428: Academic Press: San Diego; and van den Hondel, C. A. M. J. J. & Punt, P. J. (1991) "Gene transfer systems and vector development for filamentous fungi, in: Applied Molecular Genetics of Fungi, Peberdy, J. F. et al., eds., p. 1-28, Cambridge University Press: Cambridge), algae and multi-cellular plant cells (see Schmidt, R. and Willmitzer, L. (1988) High efficiency *Agrobacterium tumefaciens*—mediated transformation of *Arabidopsis thaliana* leaf and cotyledon explants" *Plant Cell Rep.:* 583-586), or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the MCT protein is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant MCT protein unfused to GST can be recovered by cleavage of the fusion protein with thrombin.

Examples of suitable inducible non-fusion *E. coli* expression vectors include pTrc (Amann et al., (1988) *Gene* 69:301-315) pLG338, pACYC184, pBR322, pUC18, pUC19, pKC30, pRep4, pHS1, pHS2, pPLc236, pMBL24, pLG200, pUR290, pIN-III113-B1, λgt11, pBdCl, and pET 11d (Studier et al., *Gene Expression Technology: Methods in Enzymology* 185, Academic Press, San Diego, Calif. (1990) 60-89; and Pouwels et al., eds. (1985) Cloning Vectors. Elsevier: New York IBSN 0 444 904018). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter. For transformation of other varieties of bacteria, appropriate vectors may be selected. For example, the plasmids pIJ101, pIJ364, pIJ702 and pIJ361 are known to be useful in transforming *Streptomyces*, while plasmids pUB110, pC194, or pBD214 are suited for transformation of Bacillus species. Several plasmids of use in the transfer of genetic information into *Corynebacterium* include pHM1519, pBL1, pSA77, or pAJ667 (Pouwels et al., eds. (1985) Cloning Vectors. Elsevier: New York IBSN 0 444 904018).

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al. (1992) *Nucleic Acids Res.* 20:2111-2118). Such alteration of nucleic acid sequences of the invention can be carried out by standard DNA synthesis techniques.

In another embodiment, the MCT protein expression vector is a yeast expression vector. Examples of vectors for expression in yeast *S. cerevisiae* include pYepSec1 (Baldari, et al., (1987) *Embo J.* 6:229-234), 2 μ, pAG-1, Yep6, Yep13, pEMBLYe23, pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge, and Pouwels et al., eds. (1985) Cloning Vectors. Elsevier: New York (IBSN 0 444 904018).

Alternatively, the MCT proteins of the invention can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156-2165) and the pVL series (Lucklow and Summers (1989) *Virology* 170:31-39).

In another embodiment, the MCT proteins of the invention may be expressed in unicellular plant cells (such as algae) or in plant cells from higher plants (e.g., the spermatophytes, such as crop plants). Examples of plant expression vectors include those detailed in: Becker, D., Kemper, E., Schell, J. and Masterson, R. (1992) "New plant binary vectors with selectable markers located proximal to the left border", *Plant Mol. Biol.* 20: 1195-1197; and Bevan, M. W. (1984) "Binary *Agrobacterium* vectors for plant transformation", *Nucl. Acid. Res.* 12: 8711-8721, and include pLGV23, pGHlac+, pBIN19, pAK2004, and pDH51 (Pouwels et al., eds. (1985) Cloning Vectors. Elsevier: New York IBSN 0 444 904018).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific;

Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *PNAS* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to MCT mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an MCT protein can be expressed in bacterial cells such as *C. glutamicum*, insect cells, yeast or mammalian cells (such as Chinese hamster ovary cells (CHO) or COS cells). Other suitable host cells are known to one of ordinary skill in the art. Microorganisms related to *Corynebacterium glutamicum* which may be conveniently used as host cells for the nucleic acid and protein molecules of the invention are set forth in Table 3.

Vector DNA can be introduced into prokaryotic or eukaryotic cells via conventional transformation or transfection techniques. As used herein, the terms "transformation" and "transfection", "conjugation" and "transduction" are intended to refer to a variety of art-recognized techniques for introducing foreign nucleic acid (e.g., linear DNA or RNA (e.g., a linearized vector or a gene construct alone without a vector) or nucleic acid in the form of a vector (e.g., a plasmid, phage, phasmid, phagemid, transposon or other DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells can be found in Sambrook, et al. (*Molecular Cloning: A Laboratory Manual. 2nd, ed.*, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an MCT protein or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared which contains at least a portion of an MCT gene into which a deletion, addition or substitution has been introduced to thereby alter, e.g., functionally disrupt, the MCT gene. Preferably, this MCT gene is a *Corynebacterium glutamicum* MCT gene, but it can be a homologue from a related bacterium or even from a mammalian, yeast, or insect source. In a preferred embodiment, the vector is designed such that, upon homologous recombination, the endogenous MCT gene is functionally disrupted (i.e., no longer encodes a functional protein; also referred to as a "knock out" vector). Alternatively, the vector can be designed such that, upon homologous recombination, the endogenous MCT gene is mutated or otherwise altered but still encodes functional protein (e.g., the upstream regulatory region can be altered to thereby alter the expression of the endogenous MCT protein). In the homologous recombination vector, the altered portion of the MCT gene is flanked at its 5' and 3' ends by additional nucleic acid of the MCT gene to allow for homologous recombination to occur between the exogenous MCT gene carried by the vector and an endogenous MCT gene in a microorganism. The additional flanking MCT nucleic acid is of sufficient length for successful homologous recombination with the endogenous gene. Typically, several kilobases of flanking DNA (both at the 5' and 3' ends) are included in the vector (see e.g., Thomas, K. R., and Capecchi, M. R. (1987) *Cell* 51: 503 for a description of homologous recombination vectors). The vector is introduced into a microorganism (e.g., by electroporation) and cells in which the introduced MCT gene has homologously recombined with the endogenous MCT gene are selected, using art-known techniques.

In another embodiment, recombinant microorganisms can be produced which contain selected systems which allow for regulated expression of the introduced gene. For example, inclusion of an MCT gene on a vector placing it under control of the lac operon permits expression of the MCT gene only in the presence of IPTG. Such regulatory systems are well known in the art.

In another embodiment, an endogenous MCT gene in a host cell is disrupted (e.g., by homologous recombination or other genetic means known in the art) such that expression of its protein product does not occur. In another embodiment, an endogenous or introduced MCT gene in a host cell has been altered by one or more point mutations, deletions, or inversions, but still encodes a functional MCT protein. In still another embodiment, one or more of the regulatory regions (e.g., a promoter, repressor, or inducer) of an MCT gene in a microorganism has been altered (e.g., by deletion, truncation, inversion, or point mutation) such that the expression of the MCT gene is modulated. One of ordinary skill in the art will appreciate that host cells containing more than one of the described MCT gene and protein modifications may be readily produced using the methods of the invention, and are meant to be included in the present invention.

A host cell of the invention, such as a prokaryotic or eukaryotic host cell in culture, can be used to produce (i.e., express) an MCT protein. Accordingly, the invention further provides methods for producing MCT proteins using the host cells of the invention. In one embodiment, the method comprises culturing the host cell of invention (into which a recombinant expression vector encoding an MCT protein has been introduced, or into which genome has been introduced a gene encoding a wild-type or altered MCT protein) in a suitable medium until MCT protein is produced. In another embodiment, the method further comprises isolating MCT proteins from the medium or the host cell.

C. Isolated MCT Proteins

Another aspect of the invention pertains to isolated MCT proteins, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of MCT protein in which the protein is separated from cellular components of the cells in which it is naturally or recombinantly produced. In one embodiment, the language "substantially free of cellular material" includes preparations of MCT protein having less than about 30% (by dry weight) of non-MCT protein (also referred to herein as a "contaminating protein"), more preferably less than about 20% of non-MCT protein, still more preferably less than about 10% of non-MCT protein, and most preferably less than about 5% non-MCT protein. When the MCT protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of MCT protein in which the protein is separated from chemical precursors or other chemicals which are involved in the synthesis of the protein. In one embodiment, the language "substantially free of chemical precursors or other chemicals" includes preparations of MCT protein having less than about 30% (by dry weight) of chemical precursors or non-MCT chemicals, more preferably less than about 20% chemical precursors or non-MCT chemicals, still more preferably less than about 10% chemical precursors or non-MCT chemicals, and most preferably less than about 5% chemical precursors or non-MCT chemicals. In preferred embodiments, isolated proteins or biologically active portions thereof lack contaminating proteins from the same organism from which the MCT protein is derived. Typically, such proteins are produced by recombinant expression of, for example, a *C. glutamicum* MCT protein in a microorganism such as *C. glutamicum*.

An isolated MCT protein or a portion thereof of the invention can participate in the metabolism of compounds necessary for the construction of cellular membranes in *C. glutamicum*, or in the transport of molecules across these membranes, or has one or more of the activities set forth in Table 1. In preferred embodiments, the protein or portion thereof comprises an amino acid sequence which is sufficiently homologous to an amino acid sequence of Appendix B such that the protein or portion thereof maintains the ability participate in the metabolism of compounds necessary for the construction of cellular membranes in *C. glutamicum*, or in the transport of molecules across these membranes. The portion of the protein is preferably a biologically active portion as described herein. In another preferred embodiment, an MCT protein of the invention has an amino acid sequence shown in Appendix B. In yet another preferred embodiment, the MCT protein has an amino acid sequence which is encoded by a nucleotide sequence which hybridizes, e.g., hybridizes under stringent conditions, to a nucleotide sequence of Appendix A. In still another preferred embodiment, the MCT protein has an amino acid sequence which is encoded by a nucleotide sequence that is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more homologous to one of the nucleic acid sequences of Appendix A, or a portion thereof. Ranges and identity values intermediate to the above-recited values, (e.g., 70-90% identical or 80-95% identical) are also intended to be encompassed by the present invention. For example, ranges of identity values using a combination of any of the above values recited as upper and/or lower limits are intended to be included. The preferred MCT proteins of the present invention also preferably possess at least one of the MCT activities described herein. For example, a preferred MCT protein of the present invention includes an amino acid sequence encoded by a nucleotide sequence which hybridizes, e.g., hybridizes under stringent conditions, to a nucleotide sequence of Appendix A, and which can participate in the metabolism of compounds necessary for the construction of cellular membranes in *C. glutamicum*, or in the transport of molecules across these membranes, or which has one or more of the activities set forth in Table 1.

In other embodiments, the MCT protein is substantially homologous to an amino acid sequence of Appendix B and retains the functional activity of the protein of one of the sequences of Appendix B yet differs in amino acid sequence due to natural variation or mutagenesis, as described in detail in subsection I above. Accordingly, in another embodiment, the MCT protein is a protein which comprises an amino acid sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more homologous to an entire amino acid sequence of Appendix B and which has at least one of the MCT activities described herein. Ranges and identity values intermediate to the above-recited values, (e.g., 70-90% identical or 80-95% identical) are also intended to be encompassed by the present invention. For example, ranges of identity values using a combination of any of the above values recited as upper and/or lower limits are intended to be included. In another embodiment, the invention pertains to a full length *C. glutamicum* protein which is substantially homologous to an entire amino acid sequence of Appendix B.

Biologically active portions of an MCT protein include peptides comprising amino acid sequences derived from the amino acid sequence of an MCT protein, e.g., the an amino acid sequence shown in Appendix B or the amino acid sequence of a protein homologous to an MCT protein, which include fewer amino acids than a full length MCT protein or the full length protein which is homologous to an MCT protein, and exhibit at least one activity of an MCT protein. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of an MCT protein. Moreover, other biologically active portions, in which other regions of the protein are deleted, can be prepared by recombinant techniques and evaluated for one or more of the activities described herein. Preferably, the biologically active portions of an MCT protein include one or more selected domains/motifs or portions thereof having biological activity.

MCT proteins are preferably produced by recombinant DNA techniques. For example, a nucleic acid molecule encoding the protein is cloned into an expression vector (as described above), the expression vector is introduced into a host cell (as described above) and the MCT protein is expressed in the host cell. The MCT protein can then be isolated from the cells by an appropriate purification scheme using standard protein purification techniques. Alternative to recombinant expression, an MCT protein, polypeptide, or peptide can be synthesized chemically using standard peptide synthesis techniques. Moreover, native MCT protein can be isolated from cells (e.g., endothelial cells), for example using an anti-MCT antibody, which can be produced by standard techniques utilizing an MCT protein or fragment thereof of this invention.

The invention also provides MCT chimeric or fusion proteins. As used herein, an MCT "chimeric protein" or "fusion protein" comprises an MCT polypeptide operatively linked to a non-MCT polypeptide. An "MCT polypeptide" refers to a polypeptide having an amino acid sequence corresponding to an MCT protein, whereas a "non-MCT polypeptide" refers to a polypeptide having an amino acid sequence corresponding to a protein which is not substantially homologous to the MCT protein, e.g., a protein which is different from the MCT protein and which is derived from the same or a different organism. Within the fusion protein, the term "operatively linked" is intended to indicate that the MCT polypeptide and the non-MCT polypeptide are fused in-frame to each other. The non-MCT polypeptide can be fused to the N-terminus or C-terminus of the MCT polypeptide. For example, in one embodiment the fusion protein is a GST-MCT fusion protein in which the MCT sequences are fused to the C-terminus of the GST sequences. Such fusion proteins can facilitate the purification of recombinant MCT proteins. In another embodiment, the fusion protein is an MCT protein containing a heterologous signal sequence at its N-terminus. In certain host cells (e.g., mammalian host cells), expression and/or secretion of an MCT protein can be increased through use of a heterologous signal sequence.

Preferably, an MCT chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An MCT-encoding nucleic acid can be cloned into such an expression vector such that the fusion moiety is linked in-frame to the MCT protein.

Homologues of the MCT protein can be generated by mutagenesis, e.g., discrete point mutation or truncation of the MCT protein. As used herein, the term "homologue" refers to a variant form of the MCT protein which acts as an agonist or antagonist of the activity of the MCT protein. An agonist of the MCT protein can retain substantially the same, or a subset, of the biological activities of the MCT protein. An antagonist of the MCT protein can inhibit one or more of the activities of the naturally occurring form of the MCT protein, by, for example, competitively binding to a downstream or upstream member of the cell membrane component metabolic cascade which includes the MCT protein, or by binding to an MCT protein which mediates transport of compounds across such membranes, thereby preventing translocation from taking place.

In an alternative embodiment, homologues of the MCT protein can be identified by screening combinatorial libraries of mutants, e.g., truncation mutants, of the MCT protein for MCT protein agonist or antagonist activity. In one embodiment, a variegated library of MCT variants is generated by combinatorial mutagenesis at the nucleic acid level and is encoded by a variegated gene library. A variegated library of MCT variants can be produced by, for example, enzymatically ligating a mixture of synthetic oligonucleotides into gene sequences such that a degenerate set of potential MCT sequences is expressible as individual polypeptides, or alternatively, as a set of larger fusion proteins (e.g., for phage display) containing the set of MCT sequences therein. There are a variety of methods which can be used to produce libraries of potential MCT homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential MCT sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the MCT protein coding can be used to generate a variegated population of MCT fragments for screening and subsequent selection of homologues of an MCT protein. In one embodiment, a library of coding sequence fragments can be generated by treating a double stranded PCR fragment of an MCT coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the MCT protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of MCT homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify MCT homologues (Arkin and Yourvan (1992) *PNAS* 89:7811-7815; Delgrave et al. (1993) *Protein Engineering* 6(3):327-331).

In another embodiment, cell based assays can be exploited to analyze a variegated MCT library, using methods well known in the art.

D. Uses and Methods of the Invention

The nucleic acid molecules, proteins, protein homologues, fusion proteins, primers, vectors, and host cells described herein can be used in one or more of the following methods: identification of *C. glutamicum* and related organisms; mapping of genomes of organisms related to *C. glutamicum*; identification and localization of *C. glutamicum* sequences of interest; evolutionary studies; determination of MCT protein regions required for function; modulation of an MCT protein activity; modulation of the metabolism of one or more cell membrane components; modulation of the transmembrane transport of one or more compounds; and modulation of cellular production of a desired compound, such as a fine chemical.

The MCT nucleic acid molecules of the invention have a variety of uses. First, they may be used to identify an organism as being *Corynebacterium glutamicum* or a close relative thereof. Also, they may be used to identify the presence of *C. glutamicum* or a relative thereof in a mixed population of microorganisms. The invention provides the nucleic acid sequences of a number of *C. glutamicum* genes; by probing the extracted genomic DNA of a culture of a unique or mixed population of microorganisms under stringent conditions with a probe spanning a region of a *C. glutamicum* gene which is unique to this organism, one can ascertain whether this organism is present.

Although *Corynebacterium glutamicum* itself is non-pathogenic, it is related to pathogenic species, such as *Corynebacterium diphtheriae*. *Corynebacterium diphtheriae* is the causative agent of diphtheria, a rapidly developing, acute, febrile infection which involves both local and systemic pathology. In this disease, a local lesion develops in the upper respiratory tract and involves necrotic injury to epithelial cells; the bacilli secrete toxin which is disseminated through this lesion to distal susceptible tissues of the body. Degenerative changes brought about by the inhibition of protein synthesis in these tissues, which include heart, muscle, peripheral nerves, adrenals, kidneys, liver and spleen, result in the systemic pathology of the disease. Diphtheria continues to have high incidence in many parts of the world, including Africa, Asia, Eastern Europe and the independent states of the former Soviet Union. An ongoing epidemic of diphtheria in the latter two regions has resulted in at least 5,000 deaths since 1990. In one embodiment, the invention provides a method of identifying the presence or activity of *Cornyebacterium diphtheriae* in a subject. This method includes detection of one or more of the nucleic acid or amino acid sequences of the invention (e.g., the sequences set forth in Appendix A or Appendix B) in a subject, thereby detecting the presence or activity of *Corynebacterium diphtheriae* in the subject. *C. glutamicum* and *C. diphtheriae* are related bacteria, and many of the nucleic acid and protein molecules in *C. glutamicum* are homologous to *C. diphtheriae* nucleic acid and protein molecules, and can therefore be used to detect *C. diphtheriae* in a subject.

The nucleic acid and protein molecules of the invention may also serve as markers for specific regions of the genome. This has utility not only in the mapping of the genome, but also for functional studies of *C. glutamicum* proteins. For example, to identify the region of the genome to which a particular *C. glutamicum* DNA-binding protein binds, the *C. glutamicum* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *C. glutamicum*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related bacteria, such as *Brevibacterium lactofermentum*.

The MCT nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the MCT nucleic acid molecules of the invention may result in the production of MCT proteins having functional differences from the wild-type MCT proteins. These proteins may be improved in efficiency or activity, may be present in greater numbers in the cell than is usual, or may be decreased in efficiency or activity.

The invention provides methods for screening molecules which modulate the activity of an MCT protein, either by interacting with the protein itself or a substrate or binding partner of the MCT protein, or by modulating the transcription or translation of an MCT nucleic acid molecule of the invention. In such methods, a microorganism expressing one or more MCT proteins of the invention is contacted with one or more test compounds, and the effect of each test compound on the activity or level of expression of the MCT protein is assessed.

There are a number of mechanisms by which the alteration of an MCT protein of the invention may directly affect the yield, production, and/or efficiency of production of a fine chemical from a C. glutamicum strain incorporating such an altered protein. Recovery of fine chemical compounds from large-scale cultures of C. glutamicum is significantly improved if C. glutamicum secretes the desired compounds, since such compounds may be readily purified from the culture medium (as opposed to extracted from the mass of C. glutamicum cells). By either increasing the number or the activity of transporter molecules which export fine chemicals from the cell, it may be possible to increase the amount of the produced fine chemical which is present in the extracellular medium, thus permitting greater ease of harvesting and purification. Conversely, in order to efficiently overproduce one or more fine chemicals, increased amounts of the cofactors, precursor molecules, and intermediate compounds for the appropriate biosynthetic pathways are required. Therefore, by increasing the number and/or activity of transporter proteins involved in the import of nutrients, such as carbon sources (i.e., sugars), nitrogen sources (i.e., amino acids, ammonium salts), phosphate, and sulfur, it may be possible to improve the production of a fine chemical, due to the removal of any nutrient supply limitations on the biosynthetic process. Further, fatty acids and lipids are themselves desirable fine chemicals, so by optimizing the activity or increasing the number of one or more MCT proteins of the invention which participate in the biosynthesis of these compounds, or by impairing the activity of one or more MCT proteins which are involved in the degradation of these compounds, it may be possible to increase the yield, production, and/or efficiency of production of fatty acid and lipid molecules from C. glutamicum.

The engineering of one or more MCT genes of the invention may also result in MCT proteins having altered activities which indirectly impact the production of one or more desired fine chemicals from C. glutamicum. For example, the normal biochemical processes of metabolism result in the production of a variety of waste products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T. (1999) Curr. Opin. Chem. Biol. 3(2): 226-235). While these waste products are typically excreted, the C. glutamicum strains utilized for large-scale fermentative production are optimized for the overproduction of one or more fine chemicals, and thus may produce more waste products than is typical for a wild-type C. glutamicum. By optimizing the activity of one or more MCT proteins of the invention which are involved in the export of waste molecules, it may be possible to improve the viability of the cell and to maintain efficient metabolic activity. Also, the presence of high intracellular levels of the desired fine chemical may actually be toxic to the cell, so by increasing the ability of the cell to secrete these compounds, one may improve the viability of the cell.

Further, the MCT proteins of the invention may be manipulated such that the relative amounts of various lipid and fatty acid molecules produced are altered. This may have a profound effect on the lipid composition of the membrane of the cell. Since each type of lipid has different physical properties, an alteration in the lipid composition of a membrane may significantly alter membrane fluidity. Changes in membrane fluidity can impact the transport of molecules across the membrane, which, as previously explicated, may modify the export of waste products or the produced fine chemical or the import of necessary nutrients. Such membrane fluidity changes may also profoundly affect the integrity of the cell; cells with relatively weaker membranes are more vulnerable in the large-scale fermentor environment to mechanical stresses which may damage or kill the cell. By manipulating MCT proteins involved in the production of fatty acids and lipids for membrane construction such that the resulting membrane has a membrane composition more amenable to the environmental conditions extant in the cultures utilized to produce fine chemicals, a greater proportion of the C. glutamicum cells should survive and multiply. Greater numbers of C. glutamicum cells in a culture should translate into greater yields, production, or efficiency of production of the fine chemical from the culture.

The aforementioned mutagenesis strategies for MCT proteins to result in increased yields of a fine chemical from C. glutamicum are not meant to be limiting; variations on these strategies will be readily apparent to one of ordinary skill in the art. Using such strategies, and incorporating the mechanisms disclosed herein, the nucleic acid and protein molecules of the invention may be utilized to generate C. glutamicum or related strains of bacteria expressing mutated MCT nucleic acid and protein molecules such that the yield, production, and/or efficiency of production of a desired compound is improved. This desired compound may be any natural product of C. glutamicum, which includes the final products of biosynthesis pathways and intermediates of naturally-occurring metabolic pathways, as well as molecules which do not naturally occur in the metabolism of C. glutamicum, but which are produced by a C. glutamicum strain of the invention.

This invention is further illustrated by the following examples which should not be construed as limiting. The contents of all references, patent applications, patents, published patent applications, Tables, Appendices, and the sequence listing cited throughout this application are hereby incorporated by reference.

Exemplification

EXAMPLE 1

Preparation of Total Genomic DNA of Corynebacterium Glutamicum ATCC 13032

A culture of Corynebacterium glutamicum (ATCC 13032) was grown overnight at 30° C. with vigorous shaking in BHI medium (Difco). The cells were harvested by centrifugation, the supernatant was discarded and the cells were resuspended in 5 ml buffer-I (5% of the original volume of the culture—all indicated volumes have been calculated for 100 ml of culture volume). Composition of buffer-I: 140.34 g/l sucrose, 2.46 g/l $MgSO_4 \times 7H_2O$, 10 ml/l $KH_2PO_4$ solution (100 g/l, adjusted to pH 6.7 with KOH), 50 ml/l M12 concentrate (10 g/l (NH$_4$)$_2$SO$_4$, 1 g/l NaCl, 2 g/l MgSO$_4$× 7H$_2$O, 0.2 g/l CaCl$_2$, 0.5 g/l yeast extract (Difco), 10 ml/l trace-elements-mix (200 mg/l FeSO$_4$×H$_2$O, 10 mg/l ZnSO$_4$×7 H$_2$O, 3 mg/l MnCl$_2$×4 H$_2$O, 30 mg/l H$_3$BO$_3$, 20 mg/l CoCl$_2$×6 H$_2$O, 1 mg/l NiCl$_2$×6 H$_2$O, 3 mg/l Na$_2$MoO$_4$×2 H$_2$O, 500 mg/l complexing agent (EDTA or critic acid), 100 ml/l vitamins-mix (0.2 mg/l biotin, 0.2 mg/l folic acid, 20 mg/l p-amino benzoic acid, 20 mg/l riboflavin, 40 mg/l ca-panthothenate, 140 mg/l nicotinic acid, 40 mg/l pyridoxole hydrochloride, 200 mg/l myo-inositol). Lysozyme was added to the suspension to a final concentration of 2.5 mg/ml. After an approximately 4 h incubation at 37° C., the cell wall was degraded and the resulting protoplasts are harvested by centrifugation. The pellet was washed once with 5 ml buffer-I and once with 5 ml TE-buffer (10 mM Tris-HCl, 1 mM EDTA, pH 8). The pellet was resuspended in 4 ml TE-buffer and 0.5 ml SDS solution (10%) and 0.5 ml NaCl solution (5 M) are added. After adding of proteinase K to a final concentration of 200 µg/ml, the suspension is incubated for ca.18 h at 37° C. The DNA was purified by extraction with phenol, phenol-chloroform-isoamylalcohol and chloroform-isoamylalcohol using standard procedures. Then, the DNA was precipitated by adding 1/50 volume of 3 M sodium acetate and 2 volumes of ethanol, followed by a 30 min incubation at −20° C. and a 30 min centrifugation at 12,000 rpm in a high speed centrifuge using a SS34 rotor (Sorvall). The DNA was dissolved in 1 ml TE-buffer containing 20 µg/ml RNaseA and dialysed at 4° C. against 1000 ml TE-buffer for at least 3 hours. During this time, the buffer was exchanged 3 times. To aliquots of 0.4 ml of the dialysed DNA solution, 0.4 ml of 2 M LiCl and 0.8 ml of ethanol are added. After a 30 min incubation at −20° C., the DNA was collected by centrifugation (13,000 rpm, Biofuge Fresco, Heraeus, Hanau, Germany). The DNA pellet was dissolved in TE-buffer. DNA prepared by this procedure could be used for all purposes, including southern blotting or construction of genomic libraries.

EXAMPLE 2

Construction of Genomic Libraries in *Escherichia coli* of *Corynebacterium glutamicum* ATCC13032

Using DNA prepared as described in Example 1, cosmid and plasmid libraries were constructed according to known and well established methods (see e.g., Sambrook, J. et al. (1989) "Molecular Cloning: A Laboratory Manual", Cold Spring Harbor Laboratory Press, or Ausubel, F. M. et al. (1994) "Current Protocols in Molecular Biology", John Wiley & Sons.)

Any plasmid or cosmid could be used. Of particular use were the plasmids pBR322 (Sutcliffe, J. G. (1979) *Proc. Natl. Acad. Sci. USA,* 75:3737-3741); pACYC177 (Change & Cohen (1978) *J. Bacteriol* 134:1141-1156), plasmids of the pBS series (pBSSK+, pBSSK− and others; Stratagene, LaJolla, USA), or cosmids as SuperCos1 (Stratagene, LaJolla, USA) or Lorist6 (Gibson, T. J., Rosenthal A. and Waterson, R. H. (1987) *Gene* 53:283-286. Gene libraries specifically for use in *C. glutamicum* may be constructed using plasmid pSL109 (Lee, H.-S. and A. J. Sinskey (1994) *J. Microbiol. Biotechnol.* 4: 256-263).

EXAMPLE 3

DNA Sequencing and Computational Functional Analysis

Genomic libraries as described in Example 2 were used for DNA sequencing according to standard methods, in particular by the chain termination method using ABI377 sequencing machines (see e.g., Fleischman, R.D. et al. (1995) "Whole-genome Random Sequencing and Assembly of Haemophilus Jnfluenzae Rd., Science, 269:496-512). Sequencing primers with the following nucleotide sequences were used: 5'-GGAAACAGTATGACCATG-3' (SEQ ID NO: 677 or 5'-GTAAAACGACGGCCAGT-3' (SEQ ID NO: 678).

EXAMPLE 4

In vivo Mutagenesis

In vivo mutagenesis of *Corynebacterium glutamicum* can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella*, p. 2277-2294, ASM: Washington.) Such strains are well known to those of ordinary skill in the art. The use of such strains is illustrated, for example, in Greener, A. and Callahan, M. (1994) *Strategies* 7: 32-34.

EXAMPLE 5

DNA Transfer Between *Escherichia coli* and *Corynebacterium glutamicum*

Several *Corynebacterium* and *Brevibacterium* species contain endogenous plasmids (as e.g., pHM1519 or PBL1) which replicate autonomously (for review see, e.g., Martin, J. F. et al. (1987) *Biotechnology,* 5:137-146). Shuttle vectors for *Escherichia coli* and *Corynebacterium glutamicum* can be readily constructed by using standard vectors for *E. coli* (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons) to which a origin or replication for and a suitable marker from *Corynebacterium glutamicum* is added. Such origins of replication are preferably taken from endogenous plasmids isolated from *Corynebacterium* and *Brevibacterium* species. Of particular use as transformation markers for these species are genes for kanamycin resistance (such as those derived from the Tn5 or Tn903 transposons) or chloramphenicol (Winnacker, E. L. (1987) "From Genes to Clones—Introduction to Gene Technology, VCH, Weinheim). There are numerous examples in the literature of the construction of a wide variety of shuttle vectors which replicate in both *E. coli* and *C. glutamicum,* and which can be used for several purposes, including gene over-expression (for reference, see e.g., Yoshihama, M. et al. (1985) *J. Bacteriol.* 162:591-597, Martin J. F. et al. (1987) *Biotechnology,* 5:137-146 and Eikmanns, B. J. et al. (1991) *Gene,* 102:93-98).

Using standard methods, it is possible to clone a gene of interest into one of the shuttle vectors described above and to introduce such a hybrid vectors into strains of *Corynebacterium glutamicum*. Transformation of *C. glutamicum* can be achieved by protoplast transformation (Kastsumata, R. et al. (1984) *J. Bacteriol.* 159306-311), electroporation (Liebl, E. et al. (1989) *FEMS Microbiol. Letters,* 53:399-303) and in cases where special vectors are used, also by conjugation (as described e.g. in Schäfer, A et al. (1990) *J. Bacteriol.* 172:1663-1666). It is also possible to transfer the shuttle vectors for *C. glutamicum* to *E. coli* by preparing plasmid DNA from *C. glutamicum* (using standard methods well-known in the art) and transforming it into *E. coli*. This transformation step can be performed using standard methods, but it is advantageous to use an Mcr-deficient *E. coli* strain, such as NM522 (Gough & Murray (1983) *J. Mol. Biol.* 166:1-19).

Genes may be overexpressed in *C. glutamicum* strains using plasmids which comprise pCG1 (U.S. Pat. No. 4,617, 267) or fragments thereof, and optionally the gene for kanamycin resistance from TN903 (Grindley, N. D. and Joyce, C. M. (1980) *Proc. Natl. Acad. Sci. USA* 77(12): 7176-7180). In addition, genes may be overexpressed in *C. glutamicum* strains using plasmid pSL109 (Lee, H.-S. and A. J. Sinskey (1994) *J. Microbiol. Biotechnol.* 4: 256-263).

Aside from the use of replicative plasmids, gene overexpression can also be achieved by integration into the genome. Genomic integration in *C. glutamicum* or other *Corynebacterium* or *Brevibacterium* species may be accomplished by well-known methods, such as homologous recombination with genomic region(s), restriction endonuclease mediated integration (REMI) (see, e.g., DE Patent 19823834), or through the use of transposons. It is also possible to modulate the activity of a gene of interest by modifying the regulatory regions (e.g., a promoter, a repressor, and/or an enhancer) by sequence modification, insertion, or deletion using site-directed methods (such as homologous recombination) or methods based on random events (such as transposon mutagenesis or REMI). Nucleic acid sequences which function as transcriptional terminators may also be inserted 3' to the coding region of one or more genes of the invention; such terminators are well-known in the art and are described, for example, in Winnacker, E. L. (1987) From Genes to Clones—Introduction to Gene Technology. VCH: Weinheim.

EXAMPLE 6

Assessment of the Expression of the Mutant Protein

Observations of the activity of a mutated protein in a transformed host cell rely on the fact that the mutant protein is expressed in a similar fashion and in a similar quantity to that of the wild-type protein. A useful method to ascertain the level of transcription of the mutant gene (an indicator of the amount of mRNA available for translation to the gene product) is to perform a Northern blot (for reference see, for example, Ausubel et al. (1988) Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information is evidence of the degree of transcription of the mutant gene. Total cellular RNA can be prepared from *Corynebacterium glutamicum* by several methods, all well-known in the art, such as that described in Bormann, E. R. et al. (1992) *Mol. Microbiol.* 6: 317-326.

To assess the presence or relative quantity of protein translated from this mRNA, standard techniques, such as a Western blot, may be employed (see, for example, Ausubel et al. (1988) Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or colorimetric label which may be readily detected. The presence and quantity of label observed indicates the presence and quantity of the desired mutant protein present in the cell.

EXAMPLE 7

Growth of Genetically Modified *Corynebacterium glutamicum*—Media and Culture Conditions Genetically modified *Corynebacteria* are cultured in synthetic or natural growth media. A number of different growth media for *Corynebacteria* are both well-known and readily available (Lieb et al. (1989) *Appl. Microbiol. Biotechnol.,* 32:205-210; von der Osten et al. (1998) *Biotechnology Letters,* 11:11-16; Patent DE 4,120,867; Liebl (1992) "The Genus *Corynebacterium,* in: The Procaryotes, Volume II, Balows, A. et al., eds. Springer-Verlag). These media consist of one or more carbon sources, nitrogen sources, inorganic salts, vitamins and trace elements. Preferred carbon sources are sugars, such as mono-, di-, or polysaccharides. For example, glucose, fructose, mannose, galactose, ribose, sorbose, ribulose, lactose, maltose, sucrose, raffinose, starch or cellulose serve as very good carbon sources. It is also possible to supply sugar to the media via complex compounds such as molasses or other by-products from sugar refinement. It can also be advantageous to supply mixtures of different carbon sources. Other possible carbon sources are alcohols and organic acids, such as methanol, ethanol, acetic acid or lactic acid. Nitrogen sources are usually organic or inorganic nitrogen compounds, or materials which contain these compounds. Exemplary nitrogen sources include ammonia gas or ammonia salts, such as $NH_4Cl$ or $(NH_4)_2SO_4$, $NH_4OH$, nitrates, urea, amino acids or complex nitrogen sources like corn steep liquor, soy bean flour, soy bean protein, yeast extract, meat extract and others.

Inorganic salt compounds which may be included in the media include the chloride-, phosphorous- or sulfate-salts of calcium, magnesium, sodium, cobalt, molybdenum, potassium, manganese, zinc, copper and iron. Chelating compounds can be added to the medium to keep the metal ions in solution. Particularly useful chelating compounds include dihydroxyphenols, like catechol or protocatechuate, or organic acids, such as citric acid. It is typical for the media to also contain other growth factors, such as vitamins or growth promoters, examples of which include biotin, riboflavin, thiamin, folic acid, nicotinic acid, pantothenate and pyridoxin. Growth factors and salts frequently originate from complex media components such as yeast extract, molasses, corn steep liquor and others. The exact composition of the media compounds depends strongly on the immediate experiment and is individually decided for each specific case. Information about media optimization is available in the textbook "Applied Microbiol. Physiology, A Practical Approach (eds. P. M. Rhodes, P. F. Stanbury, IRL Press (1997) pp. 53-73, ISBN 0 19 963577 3). It is also possible to select growth media from commercial suppliers, like standard 1 (Merck) or BHI (grain heart infusion, DIFCO) or others.

All medium components are sterilized, either by heat (20 minutes at 1.5 bar and 121° C.) or by sterile filtration. The components can either be sterilized together or, if necessary, separately. All media components can be present at the beginning of growth, or they can optionally be added continuously or batchwise.

Culture conditions are defined separately for each experiment. The temperature should be in a range between 15° C. and 45° C. The temperature can be kept constant or can be altered during the experiment. The pH of the medium should be in the range of 5 to 8.5, preferably around 7.0, and can be maintained by the addition of buffers to the media. An exemplary buffer for this purpose is a potassium phosphate buffer. Synthetic buffers such as MOPS, HEPES, ACES and others can alternatively or simultaneously be used. It is also possible to maintain a constant culture pH through the addition of NaOH or $NH_4OH$ during growth. If complex medium components such as yeast extract are utilized, the necessity for additional buffers may be reduced, due to the fact that many complex compounds have high buffer capacities. If a fermentor is utilized for culturing the microorganisms, the pH can also be controlled using gaseous ammonia.

The incubation time is usually in a range from several hours to several days. This time is selected in order to permit the maximal amount of product to accumulate in the broth. The disclosed growth experiments can be carried out in a variety of vessels, such as microtiter plates, glass tubes, glass flasks or glass or metal fermentors of different sizes. For screening a large number of clones, the microorganisms should be cultured in microtiter plates, glass tubes or shake flasks, either with or without baffles. Preferably 100 ml shake flasks are used, filled with 10% (by volume) of the required growth medium. The flasks should be shaken on a rotary shaker (amplitude 25 mm) using a speed-range of 100-300 rpm. Evaporation losses can be diminished by the maintenance of a humid atmosphere; alternatively, a mathematical correction for evaporation losses should be performed.

If genetically modified clones are tested, an unmodified control clone or a control clone containing the basic plasmid without any insert should also be tested. The medium is inoculated to an $OD_{600}$ of 0.5-1.5 using cells grown on agar plates, such as CM plates (10 g/l glucose, 2,5 g/l NaCl, 2 g/l urea, 10 g/l polypeptone, 5 g/l yeast extract, 5 g/l meat extract, 22 g/l NaCl, 2 g/l urea, 10 g/l polypeptone, 5 g/l yeast extract, 5 g/l meat extract, 22 g/l agar, pH 6.8 with 2M NaOH) that had been incubated at 30° C. Inoculation of the media is accomplished by either introduction of a saline suspension of *C. glutamicum* cells from CM plates or addition of a liquid preculture of this bacterium.

EXAMPLE 8

In vitro Analysis of the Function of Mutant Proteins

The determination of activities and kinetic parameters of enzymes is well established in the art. Experiments to determine the activity of any given altered enzyme must be tailored to the specific activity of the wild-type enzyme, which is well within the ability of one of ordinary skill in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβl, M., eds. (1983-1986) Methods of Enzymatic Analysis, $3^{rd}$ ed., vol. I-XII, Verlag Chemie: Weinheim; and Ullmann's Encyclopedia of Industrial Chemistry (1987) vol. A9, "Enzymes". VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) *EMBO J.* 14: 3895-3904 and references cited therein). Reporter gene test systems are well known and established for applications in both pro- and eukaryotic cells, using enzymes such as beta-galactosidase, green fluorescent protein, and several others.

The determination of activity of membrane-transport proteins can be performed according to techniques such as those described in Gennis, R. B. (1989) "Pores, Channels and Transporters", in Biomembranes, Molecular Structure and Function, Springer: Heidelberg, p. 85-137; 199-234; and 270-322.

EXAMPLE 9

Analysis of Impact of Mutant Protein on the Production of the Desired Product

The effect of the genetic modification in *C. glutamicum* on production of a desired compound (such as an amino acid) can be assessed by growing the modified microorganism under suitable conditions (such as those described above) and analyzing the medium and/or the cellular component for increased production of the desired product (i.e., an amino acid). Such analysis techniques are well known to one of ordinary skill in the art, and include spectroscopy, thin layer chromatography, staining methods of various kinds, enzymatic and microbiological methods, and analytical chromatography such as high performance liquid chromatography (see, for example, Ullman, Encyclopedia of Industrial Chemistry, vol. A2, p. 89-90 and p. 443-613, VCH: Weinheim (1985); Fallon, A. et al., (1987) "Applications of HPLC in Biochemistry" in: Laboratory Techniques in Biochemistry and Molecular Biology, vol. 17; Rehm et al. (1993) Biotechnology, vol. 3, Chapter III: "Product recovery and purification", page 469-714, VCH: Weinheim; Belter, P. A. et al. (1988) Bioseparations: downstream processing for biotechnology, John Wiley and Sons; Kennedy, J. F. and Cabral, J. M. S. (1992) Recovery processes for biological materials, John Wiley and Sons; Shaeiwitz, J. A. and Henry, J. D. (1988) Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications.)

In addition to the measurement of the final product of fermentation, it is also possible to analyze other components of the metabolic pathways utilized for the production of the desired compound, such as intermediates and side-products, to determine the overall efficiency of production of the compound. Analysis methods include measurements of nutrient levels in the medium (e.g., sugars, hydrocarbons, nitrogen sources, phosphate, and other ions), measurements of biomass composition and growth, analysis of the production of common metabolites of biosynthetic pathways, and measurement of gasses produced during fermentation. Standard methods for these measurements are outlined in Applied Microbial Physiology, A Practical Approach, P. M. Rhodes and P. F. Stanbury, eds., IRL Press, p. 103-129; 131-163; and 165-192 (ISBN: 0199635773) and references cited therein.

EXAMPLE 10

Purification of the Desired Product from C. glutamicum Culture

Recovery of the desired product from the C. glutamicum cells or supernatant of the above-described culture can be performed by various methods well known in the art. If the desired product is not secreted from the cells, the cells can be harvested from the culture by low-speed centrifugation, the cells can be lysed by standard techniques, such as mechanical force or sonication. The cellular debris is removed by centrifugation, and the supernatant fraction containing the soluble proteins is retained for further purification of the desired compound. If the product is secreted from the C. glutamicum cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One of ordinary skill in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There are a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986).

The identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al. (1994) *Appl. Environ. Microbiol.* 60: 133-140; Malakhova et al. (1996) *Biotekhnologiya* 11: 27-32; and Schmidt et al. (1998) *Bioprocess Engineer.* 19: 67-70. Ulmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

EXAMPLE 11

Analysis of the Gene Sequences of the Invention

The comparison of sequences and determination of percent homology between two sequences are art-known techniques, and can be accomplished using a mathematical algorithm, such as the algorithm of Karlin and Altschul (1990) *Proc. Natl. Acad. Sci.* USA 87:2264-68, modified as in Karlin and Altschul (1993) *Proc. Natl. Acad. Sci.* USA 90:5873-77. Such an algorithm is incorporated into the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to MCT nucleic acid molecules of the invention. BLAST protein searches can be performed with the XBLAST program, score=50, wordlength=3 to obtain amino acid sequences homologous to MCT protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, one of ordinary skill in the art will know how to optimize the parameters of the program (e.g., XBLAST and NBLAST) for the specific sequence being analyzed.

Another example of a mathematical algorithm utilized for the comparison of sequences is the algorithm of Meyers and Miller ((1988) *Comput. Appl. Biosci.* 4: 11-17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art, and include ADVANCE and ADAM. described in Torelli and Robotti (1994) *Comput. Appl. Biosci.* 10:3-5; and FASTA, described in Pearson and Lipman (1988) *P.N.A.S.* 85:2444-8.

The percent homology between two amino acid sequences can also be accomplished using the GAP program in the GCG software package (available at http://www.gcg.com), using either a Blosum 62 matrix or a PAM250 matrix, and a gap weight of 12, 10, 8, 6, or 4 and a length weight of 2, 3, or 4. The percent homology between two nucleic acid sequences can be accomplished using the GAP program in the GCG software package, using standard parameters, such as a gap weight of 50 and a length weight of 3.

A comparative analysis of the gene sequences of the invention with those present in Genbank has been performed using techniques known in the art (see, e.g., Bexevanis and Ouellette, eds. (1998) Bioinformatics: A Practical Guide to the Analysis of Genes and Proteins. John Wiley and Sons: New York). The gene sequences of the invention were compared to genes present in Genbank in a three-step process. In a first step, a BLASTN analysis (e.g., a local alignment analysis) was performed for each of the sequences of the invention against the nucleotide sequences present in Genbank, and the top 500 hits were retained for further analysis. A subsequent FASTA search (e.g., a combined local and global alignment analysis, in which limited regions of the sequences are aligned) was performed on these 500 hits. Each gene sequence of the invention was subsequently globally aligned to each of the top three FASTA hits, using the GAP program in the GCG software package (using standard parameters). In order to obtain correct results, the length of the sequences extracted from Genbank were adjusted to the length of the query sequences by methods well-known in the art. The results of this analysis are set forth in Table 4. The resulting data is identical to that which would have been obtained had a GAP (global) analysis alone been performed on each of the genes of the invention in comparison with each of the references in Genbank, but required significantly reduced computational time as compared to such a database-wide GAP (global) analysis. Sequences of the invention for which no alignments above the cutoff values were obtained are indicated on Table 4 by the absence of alignment information. It will further be understood by one of ordinary skill in the art that the GAP alignment homology percentages set forth in Table 4 under the heading "% homology (GAP)" are listed in the European numerical format, wherein a ',' represents a decimal point. For example, a value of "40,345" in this column represents "40.345%".

EXAMPLE 12

Construction and Operation of DNA Microarrays

The sequences of the invention may additionally be used in the construction and application of DNA microarrays (the design, methodology, and uses of DNA arrays are well known in the art, and are described, for example, in Schena, M. et al. (1995) *Science* 270: 467-470; Wodicka, L. et al. (1997) *Nature Biotechnology* 15: 1359-1367; DeSaizieu, A. et al. (1998) *Nature Biotechnology* 16: 45-48; and DeRisi, J. L. et al. (1997) *Science* 278: 680-686).

DNA microarrays are solid or flexible supports consisting of nitrocellulose, nylon, glass, silicone, or other materials. Nucleic acid molecules may be attached to the surface in an ordered manner. After appropriate labeling, other nucleic acids or nucleic acid mixtures can be hybridized to the immobilized nucleic acid molecules, and the label may be used to monitor and measure the individual signal intensities of the hybridized molecules at defined regions. This methodology allows the simultaneous quantification of the relative or absolute amount of all or selected nucleic acids in the applied nucleic acid sample or mixture. DNA microarrays, therefore, permit an analysis of the expression of multiple (as many as 6800 or more) nucleic acids in parallel (see, e.g., Schena, M. (1996) *BioEssays* 18(5): 427-431).

The sequences of the invention may be used to design oligonucleotide primers which are able to amplify defined regions of one or more *C. glutamicum* genes by a nucleic acid amplification reaction such as the polymerase chain reaction. The choice and design of the 5' or 3' oligonucleotide primers or of appropriate linkers allows the covalent attachment of the resulting PCR products to the surface of a support medium described above (and also described, for example, Schena, M. et al. (1995) *Science* 270: 467-470).

Nucleic acid microarrays may also be constructed by in situ oligonucleotide synthesis as described by Wodicka, L. et al. (1997) *Nature Biotechnology* 15: 1359-1367. By photolithographic methods, precisely defined regions of the matrix are exposed to light. Protective groups which are photolabile are thereby activated and undergo nucleotide addition, whereas regions that are masked from light do not undergo any modification. Subsequent cycles of protection and light activation permit the synthesis of different oligonucleotides at defined positions. Small, defined regions of the genes of the invention may be synthesized on microarrays by solid phase oligonucleotide synthesis.

The nucleic acid molecules of the invention present in a sample or mixture of nucleotides may be hybridized to the microarrays. These nucleic acid molecules can be labeled according to standard methods. In brief, nucleic acid molecules (e.g., mRNA molecules or DNA molecules) are labeled by the incorporation of isotopically or fluorescently labeled nucleotides, e.g., during reverse transcription or DNA synthesis. Hybridization of labeled nucleic acids to microarrays is described (e.g., in Schena, M. et al. (1995) supra; Wodicka, L. et al. (1997), supra; and DeSaizieu A. et al. (1998), supra). The detection and quantification of the hybridized molecule are tailored to the specific incorporated label. Radioactive labels can be detected, for example, as described in Schena, M. et al. (1995) supra) and fluorescent labels may be detected, for example, by the method of Shalon et al. (1996) *Genome Research* 6: 639-645).

The application of the sequences of the invention to DNA microarray technology, as described above, permits comparative analyses of different strains of *C. glutamicum* or other Corynebacteria. For example, studies of inter-strain variations based on individual transcript profiles and the identification of genes that are important for specific and/or desired strain properties such as pathogenicity, productivity and stress tolerance are facilitated by nucleic acid array methodologies. Also, comparisons of the profile of expression of genes of the invention during the course of a fermentation reaction are possible using nucleic acid array technology.

EXAMPLE 13

Analysis of the Dynamics of Cellular Protein Populations (Proteomics)

The genes, compositions, and methods of the invention may be applied to study the interactions and dynamics of populations of proteins, termed 'proteomics'. Protein populations of interest include, but are not limited to, the total protein population of *C. glutamicum* (e.g., in comparison with the protein populations of other organisms), those proteins which are active under specific environmental or metabolic conditions (e.g., during fermentation, at high or low temperature, or at high or low pH), or those proteins which are active during specific phases of growth and development.

Protein populations can be analyzed by various well-known techniques, such as gel electrophoresis. Cellular proteins may be obtained, for example, by lysis or extraction, and may be separated from one another using a variety of electrophoretic techniques. Sodium dodecyl sulfate polyacrylamide gel electrophoresis (SDS-PAGE) separates proteins largely on the basis of their molecular weight. Isoelectric focusing polyacrylamide gel electrophoresis (IEF-PAGE) separates proteins by their isoelectric point (which reflects not only the amino acid sequence but also posttranslational modifications of the protein). Another, more preferred method of protein analysis is the consecutive combination of both IEF-PAGE and SDS-PAGE, known as 2-D-gel electrophoresis (described, for example, in Hermann et al. (1998) *Electrophoresis* 19: 3217-3221; Fountoulakis et al. (1998) *Electrophoresis* 19: 1193-1202; Langen et al. (1997) *Electrophoresis* 18: 1184-1192; Antelmann et al. (1997) *Electrophoresis* 18: 1451-1463). Other separation techniques may also be utilized for protein separation, such as capillary gel electrophoresis; such techniques are well known in the art.

Proteins separated by these methodologies can be visualized by standard techniques, such as by staining or labeling. Suitable stains are known in the art, and include Coomassie Brilliant Blue, silver stain, or fluorescent dyes such as Sypro Ruby (Molecular Probes). The inclusion of radioactively labeled amino acids or other protein precursors (e.g., $^{35}$S-methionine, $^{35}$S-cysteine, $^{14}$C-labelled amino acids, $^{15}$N-amino acids, $^{15}$NO$_3$ or $^{15}$NH$_4^+$ or $^{13}$C-labelled amino acids) in the medium of *C. glutamicum* permits the labeling of proteins from these cells prior to their separation. Similarly, fluorescent labels may be employed. These labeled proteins can be extracted, isolated and separated according to the previously described techniques.

Proteins visualized by these techniques can be further analyzed by measuring the amount of dye or label used. The amount of a given protein can be determined quantitatively using, for example, optical methods and can be compared to the amount of other proteins in the same gel or in other gels. Comparisons of proteins on gels can be made, for example, by optical comparison, by spectroscopy, by image scanning and analysis of gels, or through the use of photographic films and screens. Such techniques are well-known in the art.

To determine the identity of any given protein, direct sequencing or other standard techniques may be employed. For example, N- and/or C-terminal amino acid sequencing (such as Edman degradation) may be used, as may mass spectrometry (in particular MALDI or ESI techniques (see, e.g., Langen et al. (1997) *Electrophoresis* 18: 1184-1192)). The protein sequences provided herein can be used for the identification of *C. glutamicum* proteins by these techniques.

The information obtained by these methods can be used to compare patterns of protein presence, activity, or modification between different samples from various biological conditions (e.g., different organisms, time points of fermentation, media conditions, or different biotopes, among others). Data obtained from such experiments alone, or in combination with other techniques, can be used for various applications, such as to compare the behavior of various organisms in a given (e.g., metabolic) situation, to increase the productivity of strains which produce fine chemicals or to increase the efficiency of the production of fine chemicals.

Equivalents

Those of ordinary skill in the art will recognize, or will be able to ascertain using no more than routine experimentation, many equivalents to the specific embodiments of the invention described herein. Such equivalents are intended to be encompassed by the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07273721B2). An electronic copy of the "Sequence Listing" will also be available from the USPTO upon request and payment of the fee set forth in 37 CFR 1.19(b)(3).

What is claimed is:

1. An isolated nucleic acid molecule comprising the nucleotide sequence set forth in SEQ ID NO:5, or a full complement thereof.

2. A host cell comprising a nucleic acid molecule comprising the nucleotide sequence set forth in SEQ ID NO:5, wherein the nucleotide sequence of SEQ ID NO:5 is disrupted.

3. A host cell comprising a nucleic acid molecule comprising the nucleotide sequence set forth in SEQ ID NO:5, wherein the nucleic acid molecule comprises one or more nucleic acid modifications as compared to the nucleotide sequence as set forth in SEQ ID NO:5, wherein the nucleic acid molecule encodes a polypeptide having a cysQ activity.

4. A host cell comprising a nucleic acid molecule comprising the nucleotide sequence set forth in SEQ ID NO:5, wherein the regulatory region of the nucleic acid molecule is modified relative to the wild-type regulatory region of the molecule and wherein the regulatory region is operably linked to SEQ ID NO:5.

5. An isolated nucleic acid molecule which encodes a polypeptide comprising the amino acid sequence set forth in SEQ ID NO:6, or a full complement thereof.

6. An isolated nucleic acid molecule comprising a nucleotide sequence which is at least 90% identical to the entire nucleotide sequence set forth in SEQ ID NO:5, wherein the nucleic acid molecule encodes a polypeptide having a cysQ activity, or a full complement thereof.

7. The nucleic acid molecule of claim 6, wherein the nucleotide sequence has at least 95% identity to the entire nucleotide sequence of SEQ ID NO:5.

8. An isolated nucleic acid molecule which encodes a polypeptide comprising an amino acid sequence which is at least 90% identical to the entire amino acid sequence of SEQ ID NO:6, wherein the polypeptide has a cysQ activity, or a full complement thereof.

9. The nucleic acid molecule of claim 8 wherein the polypeptide comprises an amino acid sequence which is at least 95% identical to the entire amino acid sequence of SEQ ID NO:6.

10. An isolated nucleic acid molecule comprising a fragment of at least 15 contiguous nucleotides of the nucleotide sequence set forth in SEQ ID NO:5, or a full complement thereof.

11. An isolated nucleic acid molecule comprising the nucleic acid molecule as in any one of claims 1 or 5-10 and a nucleotide sequence encoding a heterologous polypeptide.

12. A vector comprising the nucleic acid molecule as in any one of claims 1 or 5-10.

13. The vector of claim 12, which is an expression vector.

14. A host cell transfected with the expression vector of claim 13.

15. The host cell of claim 14, wherein said cell is a microorganism.

16. The host cell of claim 15, wherein said cell belongs to the genus *Corynebacterium* or *Brevibacterium*.

17. The host cell of claim 14, wherein the expression of said nucleic acid molecule results in the modulation in production of a fine chemical from said cell.

18. The host cell of claim 17, wherein said fine chemical is selected from the group consisting of: organic acids, proteinogenic and nonproteinogenic amino acids, purine and pyrimidine bases, nucleosides, nucleotides, lipids, saturated and unsaturated fatty acids, diols, carbohydrates, aromatic compounds, vitamins, cofactors, polyketides, and enzymes.

19. A method of producing a polypeptide comprising culturing the host cell of claim 14 in an appropriate culture medium to, thereby, produce the polypeptide.

20. A method for producing a fine chemical, comprising culturing the cell of claim 14 such that the fine chemical is produced.

21. The method of claim 20, wherein said method further comprises the step of recovering the fine chemical from said culture.

22. The method of claim 20, wherein said cell belongs to the genus *Corynebacterium* or *Brevibacterium*.

23. The method of claim 20, wherein said cell is selected from the group consisting of: *Corynebacterium glutamicum, Corynebacterium herculis, Corynebacterium lilium, Corynebacterium acetoacidophilum, Corynebacterium acetoglutamicum, Corynebacterium acetophilum, Corynebacterium ammoniagenes, Corynebacterium fujiokense, Corynebacterium nitrilophilus, Brevibacterium ammoniagenes, Brevibacterium butanicum, Brevibacterium divaricatum, Brevibacterium flavum, Brevibacterium healii, Brevibacterium ketoglutamicum, Brevibacterium ketosoreductum, Brevibacterium lactofermentum, Brevibacterium linens, Brevibacterium paraffinolyticum*, and those strains set forth in Table 3.

24. The method of claim 20, wherein expression of the nucleic acid molecule from said vector results in modulation of production of said fine chemical.

25. The method of claim 20, wherein said fine chemical is selected from the group consisting of: organic acids, proteinogenic and nonproteinogenic amino acids, purine and pyrimidine bases, nucleosides, nucleotides, lipids, saturated and unsaturated fatty acids, diols, carbohydrates, aromatic compounds, vitamins, cofactors, polyketides, and enzymes.

26. The method of claim 20, wherein said fine chemical is an amino acid.

27. The method of claim 26, wherein said amino acid is drawn from the group consisting of: lysine, glutamate, glutamine, alanine, aspartate, glycine, serine, threonine, methionine, cysteine, valine, leucine, isoleucine, arginine, proline, histidine, tyrosine, phenylalanine, and tryptophan.

28. A method for producing a fine chemical, comprising culturing a cell whose genomic DNA has been altered by the inclusion of a nucleic acid molecule as in any one of claims 1 or 5-10.

* * * * *